(12) United States Patent
Soe et al.

(10) Patent No.: US 9,493,749 B2
(45) Date of Patent: Nov. 15, 2016

(54) PROCESS MODIFICATIONS TO ENHANCE CHLOROPHYLL DEGRADATION

(75) Inventors: Jorn Borch Soe, Tilst (DK); Tina Lillan Jorgensen, Silkeborg (DE); Lene Lauridsen, Riskov (DK); Rene Mikkelsen, Hovedgard (DK); Janne Brunstedt, Rosklide (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 544 days.

(21) Appl. No.: 14/000,970

(22) PCT Filed: Feb. 16, 2012

(86) PCT No.: PCT/IB2012/050715
§ 371 (c)(1),
(2), (4) Date: Aug. 22, 2013

(87) PCT Pub. No.: WO2012/114234
PCT Pub. Date: Aug. 30, 2012

(65) Prior Publication Data
US 2013/0330804 A1    Dec. 12, 2013
US 2014/0363877 A9    Dec. 11, 2014

Related U.S. Application Data

(60) Provisional application No. 61/445,665, filed on Feb. 23, 2011.

(51) Int. Cl.
*C11B 3/00*    (2006.01)
*C12P 7/64*    (2006.01)
*A23D 9/04*    (2006.01)
*C12N 9/18*    (2006.01)

(52) U.S. Cl.
CPC . *C12N 9/18* (2013.01); *A23D 9/04* (2013.01); *C11B 3/003* (2013.01); *C12P 7/6445* (2013.01); *C12Y 301/01014* (2013.01); *Y02P 20/52* (2015.11)

(58) Field of Classification Search
CPC .......... A23D 9/04; C11B 3/003; C12N 9/18; C12P 7/6445; C12Y 301/01014; Y02P 20/52
See application file for complete search history.

(56) References Cited

U.S. PATENT DOCUMENTS

2008/0070291 A1    3/2008  Lam et al.

FOREIGN PATENT DOCUMENTS

WO    WO 2010/143149 A2    12/2010
WO    WO 2011/158203 A1    12/2011

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Arkus, K.A.J., et al., "Mechanistic analysis of wheat chlorophyllase," *Archives of Biochemistry and Biophysics*, 2005, vol. 438, pp. 146-155.
Chan, A.P., et al., "Draft genome sequence of the oilseed species *Ricinus communis*," *Nature Biotechnology*, 2010, vol. 28, No. 9, pp. 951-956+3.
Sequences Uniprot, Accession B9RTK6, submitted Mar. 24, 2009.
International Search Report, PCT International Appl. No. PCT/IB2012/050715, Mailed Aug. 30, 2012 (3 Pages).
International Preliminary Report on Patentability, Issued Aug. 27, 2013 (9 Pages).

* cited by examiner

*Primary Examiner* — Delia Ramirez

(57) ABSTRACT

In one aspect, there is provided a process for treating a plant oil, comprising a step of contacting the oil with an enzyme, wherein the enzyme is capable of hydrolyzing an a' or b' stereoisomer of chlorophyll or a chlorophyll derivative.

9 Claims, 21 Drawing Sheets

Figure 12 (SEQ ID NO:1)

ARA_CHL

```
  1    MAAIEDSPTF  SSVVTPAAFE  IGSLPTTEIP  VDPVENDSTA  PPKPVRITCP
 51    TVAGTYPVVL  FFHGFYLRNY  FYSDVLNHIA  SHGYILVAPQ  LCKLLPPGGQ
101    VEVDDAGSVI  NWASENLKAH  LPTSVNANGK  YTSLVGHSRG  GKTAFAVALG
151    HAATLDPSIT  FSALIGIDPV  AGTNKYIRTD  PHILTYKPES  FELDIPVAVV
201    GTGLGPKWNN  VMPPCAPTDL  NHEEFYKECK  ATKAHFVAAD  YGHMDMLDDD
251    LPGFVGFMAG  CMCKNGQRKK  SEMRSFVGGI  VVAFLKYSLW  GEKAEIRLIV
301    KDPSVSPAKL  DPSPELEEAS  GIFV
```

Figure 13 (SEQ ID NO:2)

ARA_CHL2

```
  1    MSSSSSRNAF  EDGKYKSNLL  TLDSSSRCCK  ITPSSRASPS  PPKQLLVATP
 51    VEEGDYPVVM  LLHGYLLYNS  FYSQLMLHVS  SHGFILIAPQ  LYSIAGPDTM
101    DEIKSTAEIM  DWLSVGLNHF  LPAQVTPNLS  KFALSGHSRG  GKTAFAVALK
151    KFGYSSNLKI  STLIGIDPVD  GTGKGKQTPP  PVLAYLPNSF  DLDKTPILVI
201    GSGLGETARN  PLFPPCAPPG  VNHREFFREC  QGPAWHFVAK  DYGHLDMLDD
251    DTKGIRGKSS  YCLCKNGEER  RPMRRFVGGL  VVSFLKAYLE  GDDRELVKIK
301    DGCHEDVPVE  IQEFEVIM
```

Figure 14 (SEQ ID NO:3)

CIT_CHL

```
  1    MAAMVDAKPA  ASVQGTPLLA  TATLPVFTRG  IYSTKRITLE  TSSPSSPPPP
 51    KPLIIVTPAG  KGTFNVILFL  HGTSLSNKSY  SKIFDHIASH  GFIVVAPQLY
101    TSIPPPSATN  ELNSAAEVAE  WLPQGLQQNL  PENTEANVSL  VAVMGHSRGG
151    QTAFALSLRY  GFGAVIGLDP  VAGTSKTTGL  DPSILSFDSF  DFSIPVTVIG
201    TGLGGVARCI  TACAPEGANH  EEFFNRCKNS  SRAHFVATDY  GHMDILDDNP
251    SDVKSWALSK  YFCKNGNESR  DPMRRCVSGI  VVAFLKDFFY  GDAEDFRQIL
301    KDPSFAPIKL  DSVEYIDASS  MLTTTHVKV
```

Figure 15 (SEQ ID NO:4)

TRI_CHL

```
  1    MAAAAPAETM  NKSAAGAEVP  EAFTSVFQPG  KLAVEAIQVD  ENAAPTPPIP
 51    VLIVAPKDAG  TYPVAMLLHG  FFLHNHFYEH  LLRHVASHGF  IIVAPQFSIS
101    IIPSGDAEDI  AAAAKVADWL  PDGLPSVLPK  GVEPELSKLA  LAGHSRGGHT
151    AFSLALGHAK  TQLTFSALIG  LDPVAGTGKS  SQLQPKILTY  EPSSFGMAMP
201    VLVIGTGLGE  EKKNIFFPPC  APKDVNHAEF  YRECRPPCYY  FVTKDYGHLD
251    MLDDDAPKFI  TCVCKDGNGC  KGKMRRCVAG  IMVAFLNAAL  GEKDADLEAI
301    LRDPAVAPTT  LDPVEHRVA
```

Figure 16 (SEQ ID NO:5)

```
TRI_CHL2
    1    MAAMATTVFQ AGPMEVDVKH VDKSMIPNLA RPLMVVAPKE TGAYPVIVFL
   51    HGWNMLNSWY EQLLTHVASH GFIAVAPQLY WMVSEPDADD IDATKRITNW
  101    LADHDKGLAH VLKDVLKLEH VEPDLSKLAL AGHSRGGQTA FAVALGLGDA
  151    KTKLELKFSA LIGVDPVAGV SRAQQLEPKV LTFEPDCLDV GMPVLVMGTG
  201    LGPKHIGGFP CAPVGVNHAE FYKECAPPRY HLVVKDYGHL DMLDDNVPYI
  251    INNCMCMRNQ HDTKDLARRT MGGAMVAFLR AKLRIDVRDL IAIYHNPEIA
  301    PAVLDQVDEF LPCFVGRPNP SSV
```

Figure 17 (SEQ ID NO:6)

```
BRA_CHL
    1    MSPSFLFFTL FLIKEMSSSS SANSFEDGKY KTDLLTVGLS SCCWKKPSSS
   51    PTPQSPPKRL LVATPVEEGE YPVVMLLHGY LLYNSFYSQL MLHVSSHGFI
  101    VIAPQLYSIA GPDTMDEIKS TAEIIDWLSV GLNHFLPPQV TPNLSKFALS
  151    GHSRGGKTAF ALALKKFGYS SDLKISALIG IDVGTVFWTN GYGQYSGEFF
  201    EQFDCRNDRI VES
```

Figure 18 (SEQ ID NO:7)

```
BRA_CHL1
    1    MAGKEDSETF FSAATPLAFE LGSLPTTVIP ADPSATDLTA PPKPVIITSP
   51    TVAGTYPVVL FFHGFYLRNY FYSDVINHVA SHGYIVVAPQ LCKILPPGGQ
  101    VEVDDAGKVI NWTSKNLKAH LPSSVNANGN YTALVGHSRG GKTAFAVALG
  151    HAATLDPSIK FSALVGIDPV AGISKCIRTD PEILTYKPES FDLDMPVAVI
  201    GTGLGPKSNM LMPPCAPAEV NHEEFYIECK ATKGHFVAAD YGHMDMLDDN
  251    LPGFVGFMAG CMCKNGKRKK SEMRSFVGGI VVAFLKYSIW GEMSEIRQIL
  301    KDPSVSPARL DPSPELEEAS GYLV
```

Figure 19 (SEQ ID NO:8)

```
Brass_CHL2
    1    MSSSSSRNAF VDGKYKPDLL TVDLASRCRC YKTTPSSSLT PPPPPKSLLV
   51    ATPVEEGEYP VVMLLHGYLL YNSFYSQLML HVSSYGFIVI APQLYNIAGP
  101    DTIDEIKSTA EIIDWLSVGL NHFLPPQVTP NLSKFALTGH SRGGKTAFAV
  151    ALKKFGYSSE LKISAIIGVD PVDGTGKGKQ TPPPVLTYEP NSFNLEKMPV
  201    LVIGSGLGEL ARNPLFPPCA PTGVNHREFF QECQGPAWHF VAKDYGHLDM
  251    LDDDTKGLRG KSSYCLCKNG EERKPMRRFI GGIVVSFLMA YLEDDDCELV
  301    KIKAGCHEGV PVEIQEFEVK K
```

Figure 20 (SEQ ID NO:9)

ZEA_CHL

```
  1    MAASPVAIGT AVFQRGPLRV EARHVDYSQV PSVPKPLMVV APTDAGVYPV
 51    AVFLHGCNTV NSWYESLLSH VASHGFIAVA PQLYCVTLNM NDLKDIDATR
101    QVTAWLADKQ QGLAHVLANI LQLHGVRPDL SRLALAGHSR GGDTAFAVAL
151    GLGPAASDDD DNNADAGTSP AALPLKFSAL IGVDPVAGLS KQAQVEPKVL
201    TFRPRSLDPG MPALVVGTGL GPKHVGGPPC APAGVNHAEF YDECAPPRYH
251    VVLRDYGHMD MLDDDGVPYV INNCMCMRNT KDTKDLARRA IGGAVVAFLR
301    ATLEDDDEDL KVVLENRPGL SPAVLDPVGH DLA
```

Figure 21 (SEQ ID NO:10)

ZEA_CHL

```
  1    MNLASAVRVF LSYCLLLHRW MGSEQAGGVF DQGGHSVSLT RLDEARAPPR
 51    CAVQSSLSSA ASLPPKPLLV AAPRETGEYP VILFLHGYLA VNSFYSQLFE
101    HVASHGFIVV GPQLYTISGA DTTEEINSAA AVIDWLATGL PSTLPLGVRA
151    DLTKVSISGH SRGGKVAFAL ALGHAKAKLA VPLAAVVAVD PVDGMGVGKQ
201    TPPPILTGRH GSLHVGAPTM VIGTGLGELP RGSLLPPCAP RGVSHAAFYD
251    ELDGAAPACH LVARDYGHTD MMDDDTPGAR GMLTRTICRS GGARAPMRRF
301    VAGATVAFLK KWVAGDAAAM DSITARPDQA PIALSVVEFG DEKAIA
```

Figure 22 (SEQ ID NO:11)

BAM_CHL

```
  1    MAATAEIKIP STEALEAVTS VFRPGKLAVE LVPVDHNAVP TPPIPILIVA
 51    PKDAGTYPVA MLLHGFFLQN HFYEHLLKHV ASHGFIMVAP QFHAICTGET
101    EDIAAAAKVT DWLPEGLPSV LLKGVEADLS KLALAGHSRG GHTAFSLALG
151    HGKTNLNFAA LIGLDPVAGT GKSSQLPPKI LTYKPSSFDV AMPVLVIGTG
201    LGEEKKNVLF PPCAPKDVNH REFYYECKPP CYYFVTKDYG HLDMLDDDAP
251    KFITCLCKDG DNCKDKMRRA VAGIMIAFLR AVLDEKDGDI KVILKDPGLA
301    PVTLDPVECR LP
```

Figure 23 (SEQ ID NO:12)

CHE_CHL

```
  1    MAKLLLLIFG VFIFVNSQAQ TFPTILEKHN SEKITDVFHK GNFQVTNNPI
 51    RVKRYEFSAP EPLIIISPKE AGVYPVLLFI HGTMLSNEDY SLFFNYIASH
101    GFIVVAPKLF RLFPPKLPSQ QDEIDMAASV ANWMPLYLQV VLQRYVTGVE
151    GDLEKLAISG HSRGGKSAFA LALGFSNIKL DVTFSALIGV DPVAGRSVDD
201    RTLPHVLTYK PNSFNLSIPV TVIGSGLGNH TISCAPNHVS HQQFYDECKE
251    NSSHFVITKY GHMDMLNEFR LSPIAVTMSL MCAQSFRPKA TMRRTLGGIM
301    VAFLNAYFRD DGRQYYAIIA NRSLAPTNLF AEKKGFNFGF ATTYAQL*
```

Figure 24 (SEQ ID NO:13)

```
CB_CHL
    1   MSSSCATVTN  VYENGKYTTV  VAKIESGSCA  RSSLPLPLPP  KPLLIAMPSE
   51   AGEFPVLIFL  HGYLLYNSFY  SLLIQHVASH  GFIVIAPQLY  TVAGADSADE
  101   IKCTAAITNW  LSKGLHHVLP  PHVQPKLSKL  GLAGHSRGGK  AAFALALQKA
  151   GISTALKFSA  LIGVDPVDGM  DKGKQTPPPV  LTYTPHSFDL  DMAAMVIGSG
  201   LGEVKRNPMF  PPCAPKGVNH  EDFFKECKKP  AYYFVVKDYG  HLDMLDDDTN
  251   GIRGKATYCL  CVNGKSREPM  RRFVGGVLVA  FLKAYLGGDS  SDLMTITDGQ
  301   TGPVELQAAE  CYV
```

Figure 25 (SEQ ID NO:14)

```
GlyMax_CHL
    1   MAQRAQPALA  TTDVFQKGDI  HWKQFNVETS  TASSSPPKPL  LIFTPTVPGL
   51   YPVILFCHGF  CIRTSYYSKL  LAHIVSHGFI  LVAPQLFSIG  VPMFGPEEVK
  101   CEGRVVDWLD  NGLQPLLPES  VEAKLEKLVL  VGHSKGGKTA  FAVALGYCKT
  151   KLKFSALIGI  DPVAGVSKCK  PCRSLPDILT  GVPRSFNLNI  PVAVIGTGLG
  201   PEKANSLFPP  CAPNGVNHKE  FFSECKPPSA  YFVATDYGHM  DMLDDETPGV
  251   IGTMMSKCMC  KNGKKGPRDL  MRRTVGGLVV  AFLRAQLNEQ  WKDFDAILAS
  301   PNLAPAKLDD  VRYLPT
```

Figure 26 (SEQ ID NO:15)

```
Gin_CHL
    1   MVLVKDVFSE  GPLPVQILAI  PQANSSPCSK  LADKNGTATT  PSPCRPPKPL
   51   LIALPSQHGD  YPLILFFHGY  VLLNSFYSQL  LRHVASHGYI  AIAPQMYSVI
  101   GPNTTPEIAD  AAAITDWLRD  GLSDNLPQAL  NNHVRPNFEK  FVLAGHSRGG
  151   KVAFALALGR  VSQPSLKYSA  LVGLDPVDGM  GKDQQTSHPI  LSYREHSFDL
  201   GMPTLVVGSG  LGPCKRNPLF  PPCAPQGVNH  HDFFYECVAP  AYHFVASDYG
  251   HLDFLDDDTK  GIRGKATYCL  CKNGEAREPM  RKFSGGIVVA  FLQAFLGDNR
  301   GALNDIMVYP  SHAPVKIEPP  ESLVTEDVKS  PEVELLRRAV  CR
```

Figure 27 (SEQ ID NO:16)

```
PAC_CHL
    1   MAQLLETKHD  LSTVVPVFVT  GKYHPTSVSV  DPSNSSPSSP  PKPLLIFTPS
   51   EQGTYPVILF  FHGFYLRNNF  YTGLLLHISS  HGFIIVAPQL  SNIIPPSGTE
  101   EVEHAAKVAD  WLPSGLPSVL  PGNVEANLAK  LALVGHSRGG  KTAFALALGR
  151   AKTAQNFSAL  VGIDPVAGNR  FGETSPKILT  YTPGSFDLSI  PVAVVGTGLG
  201   PESKGCMPCP  CAPTQYNHEE  FFNECKPPRV  HFDAKNYGHM  DTLDDNPSGF
  251   IGKLSDTICV  NGEGPRDPMR  RCVGGIVVAF  LNYFFEAEKE  DFMTIMNEPY
  301   VAPVTLDQVQ  FNV
```

Figure 28 (SEQ ID NO:17)

```
POP_CHL
    1   MSSSSAIATV  TTTVFEAGKY  TTVLQKVESR  TTCCTAKTSP  PLPVPPPKPL
   51   LIVMPCEAGE  FPLLVFLHGY  LLYNSFYSQL  LQHIASHGFI  VIAPQLYLVA
  101   GQDSSDEIKS  VAATTNWLSE  GLHHLLPPHV  KPNLSKLGLA  GHSRGGKTAF
  151   ALALEKAAAT  LKFSALIGVD  PVDGMDKGKQ  TPPPVLTYVP  HSFDLDMAIM
  201   VIGSGLGELK  KNPLFPPCAP  EGVNHKDFFK  ECKGPASYFV  VKDYGHLDML
  251   DDDTEGIRGK  TTYCLCKNGK  SREPMRKFIG  GVVVAFMKAY  LGGDSSDLMA
  301   IKGGQTGPVE  LQTVEYIL
```

Figure 29 (SEQ ID NO:18)

```
Sor_CHL
    1   MATTPKVLEE  PPSAVITSVF  QPGKLAVEVI  SVEHDARPTP  PPIPILIAAP
   51   KDAGTYPVAI  LLHGFFLQNR  YYEQLLKHVA  SFGFIMVAPQ  FHTSLISNSD
  101   ADDIAAAAKV  TDWLPEGLPT  VLPTGVEADL  SKLALAGHSR  GGHTAFSLAL
  151   GYAKTNTSSL  LKFSALIGLD  PVAGTGKNSQ  LPPAILTYEP  SSFDIAVPVL
  201   VIGTGLGDER  ENALFPPCAP  VEVNHAEFYR  ECRAPCYHLV  TKDYGHLDML
  251   DDDAPKLVTC  LCKEGNTCKD  VMRRTVAGIM  VAFLKAVMGE  DEDGDLKAIL
  301   QHPGLAPTIL  DPVEYRLA
```

Figure 30 (SEQ ID NO:19)

```
SORG_CHL
    1   MASPVAISTT  AVFKRGRHPV  DTKHVDHSQV  PGVPKPLMVV  TPTDAGVYPV
   51   AVFLHGCSMY  NSWYQTLLSH  VASHGFIAVA  PQLGGILPPL  DMKDLKDIDA
  101   TRKVTAWLAD  NLAHVLTNIL  HLHGVTPDLS  RLALAGHSRG  GDTAFAVALG
  151   LGSSSSSSDT  TPLKFSALIG  VDPVAGLSKE  LQLEPKVLTF  EPRSLDPGMP
  201   ALVVGTGLGP  KGLLPCAPAG  VSHGEFYDEC  APPRYHVVVR  DYGHLDMLDD
  251   DGVPYVISNC  MCKRNTNTTK  DLARRAIGGA  MVAFLRAKLE  DDDEDLRAVL
  301   QNSPGLSPAV  LDPVEYDDDE  AMDGPGCAGN  NGVAGASG
```

Figure 31 (SEQ ID NO:20)

```
Vitis_CHL
    1   MALLGGNPST  QGIKLDLKTT  TSVFEPGNLS  VTCIRVETSN  IASPPKPLLI
   51   VTPTIQGTYP  VLLFLHGFEL  RNTFYTQLLQ  LISSHGYIVV  APQLYGLLPP
  101   SGIQEIKSAA  AVTNWLSSGL  QSVLPENVKP  DLLKLALSGH  SRGGKTAFAL
  151   ALGYADTSLN  FSALLGLDPV  GGLSKCSQTV  PKILTYVPHS  FNLAIPVCVI
  201   GTGLGDEPRN  CLTCPCAPDG  VNHVEFFSEC  KPPCSHFVTT  EYGHLDMLDD
  251   HLSGCIGAIS  GYICKSGKGP  RDPMRRCVGG  LFVAFLKAYL  EGQTGDFKAI
  301   VDEPDLAPVK  LDPVEFIEA
```

Figure 32 (SEQ ID NO:21)

```
PHYS_CHL
    1    MEDPIPNVHG GIYEDGPFKI EIVHVDDASS SSTCLKKSRA AVDRENLSPK
   51    PLVVALPKEE GVYPVIQFHH GFTLQNMFYS QIISHIASYG FIVVAPQMYK
  101    ISGSDATTEI EDAVQILNWM PTGLVAALPE TLSKHRPDFS KVALVGHSRG
  151    AKVVFGLALG VRNSILQYSA VVGLDPVDGM GIGQQTNPPI LQFSEGSLNL
  201    GVPTLIIGTG LGPLRKNFLF PACAPAGVSH EAFYYDSAAP AFHFVASKQG
  251    HMDFLNDDCS GPTGMFSYCL CKNGPTRKPM RRFSGGMVVA FLRAAFFGET
  301    APLVAALATP ELAPIPLDRP EFKGKLGDAF NKPMLAPALT P
```

Figure 33 (SEQ ID NO:22)

```
AQU_CHL
    1    MTTSLPPPKP LLIATPSEEG QFPVLIFLHG FLLFNKFYSQ LIQHIASHGF
   51    IVIAPQLYKV AGPDTTDEIK SAALVIDWLS NGLHSVLPPL VQPNLSKLGI
  101    GGHSRGGKVA FALALGHIKT SLKYSVLLGI DPVDGMGQGN QTPPPVLTYT
  151    PRSFDFNMPV LVIGSGLGET KKNSLFPPCA PKGVNHENFY SECCSPACYF
  201    VVKDYGHMDM LDDDTGGVRG KATYCTCSNG KAREPMRTFV GGIMVAFMKA
  251    YMENDSRDLM AIKETQGMAL IELQSVEFRL
```

Figure 34 (SEQ ID NO:23)

```
BRACH_CHL
    1    MAATAAAAEL KKNSGADVLE AVITSVFQPG KLAVEVIQVD HNAVPTPPIP
   51    VLIVAPKDAG TYPVAMLLHG FFLQNHYYKQ LLRHVASHGF IMVAPQFHLS
  101    MIPTGDTKDI EAAAKVSDWL PEGLPSVLPK GVEPELSKLA LAGHSRGGHT
  151    AFSLALGHAK SNLSFSALIG IDPVAGTGKS SQLAPKILTY EPSSFNMSAA
  201    MPVLVIGTGL GEEKKNIFTP PCAPKDVNHR EFYLECKPPC YYFVTKDYGH
  251    LDMLDDDAPM VITCLCKDGG SCKDKMRRCV AGIMVAFLNS ALGGKDNAAH
  301    DLEVIVKDPA LAPTTLDPVE CRLE
```

Figure 35 (SEQ ID NO:24)

```
MED_CHL
    1    MCSSVSNVFE TGNYTTKLLR VDSCSHAQNV PPPKSLLIAT PIEGGEFPLL
   51    LFLHGYLLLN SFYSQLIQHV ASHGFIVIAP QLYTVAGPDI TEEIYSVAAI
  101    TNWLSKGLSK ILPLNIKPNF HKLALGGHSR GGKTSFAVAL RKLNMTTDLK
  151    FSAIIGVDPV DGMDKGKQTS PPIFTYVPHS FDYDMATLVI GFGLGDVKKN
  201    PLFPPCAPKG VNHEDFFSEC EKPSWYFVAK DYGHVDMLDD DTKGVRGKVS
  251    YCLCKNGESR KPMRMFVGGV MVAFLKAYLH GDNVDLLAIR DKNLSVPIEM
  301    KFDYFV
```

Figure 36 (SEQ ID NO:25)

```
PIP_CHL
     1    MAASSVFEMG KLEVHVKSVN QSNSSSPPKS LLISYPSQKG DYGVVLFLHG
    51    FLISNSFYKE LISHISSHGY IVVAPRIIYP CLQDEINSAA QVANWLPEGL
   101    QAALPPNVQP NTSKLTLAGH SRGGKAAFCM LLGLAGSPLT VQFSGLIGVD
   151    PVAGFQIPGI NYKMEIPPKI ITNNSKPFDI NVPTLIIGTE LGEEAKGCLA
   201    PPYAPAGLNY EQFYEKSKEP SYQFVAKGYG HVDMLDDISK NDLMGKLTYC
   251    VCKNGKEREP MRRTAGGLMV AFLKAFSDGQ RDDLDAILND PELAPIQLDA
   301    GAKLSS
```

Figure 37 (SEQ ID NO:26)

```
LOTUS_CHL
     1    MSLSISSVTH PSSVMGSDAS TALTNVFDSG KYTTKFQRIE SNSCNGTHPD
    51    PPPPKSLLIA TPLEGGEFPV LLFLHGYLLY NSFYSQLIQH IASHGFIVIA
   101    PQLYAVAGPD VSGEIHSTAA IKNWLSEGLS KFLPPNVTPN SSKLALAGHS
   151    RGGKTAFAVA LRKLNITTDL KFSALVGVDP VDGLDRGKQT PPPVLTYVPH
   201    SFDFDMPAMV IGSGLGDVKR NPLFPPCAPK TVNHEDFFNE CNKPAWYFVA
   251    KDYGHVDMLD DDTNGIIGKA TYCLCKNGES RKPMRTFVGG LVVAFLKAYL
   301    QGDNRDSLAI KDKHLSAPVE LKFDYFV
```

Figure 38 (SEQ ID NO:27)

```
ORYI_CHL
     1    MIAFAAQILA FCLLLLLLLL LQLQTTMAGD SSFSGVFDHG SHGVTLVKVD
    51    EAPRKCSSAA AAKKTDDDTA PAGGAPPKPL LVAAPCDAGV YPVVVFLHGY
   101    LAYNSFYSQL FEHVASHGFV VVGPQVNQSI LIYYFSYIRC LDRIPPTRST
   151    RRAAVINWLA AGGLTSKLPP NVRADATKIS ISGHSRGGKV AFALALGHAN
   201    VSLRGGAGGA TIAALVAVDP VDGFATGKQT PPPILTYGGA NSLRVPAPVM
   251    VIGTGLGGLA RAAPLLPACA PPGVSHGEFY GECAAPACHL VARDYGHTDM
   301    VVDVTPGSWA SLRVPCAGAS APGRPCVGSS SAPWSRS
```

Figure 39 (SEQ ID NO:28)

```
ORYJ1_CHL
     1    MIAFAAQILA FCLLLLLLLL LQLQTTMAGD SSFSGVFDHG SHGVTLVKVD
    51    EAPRKCSSAA AAKKTDDDTA PAGGAPPKPL LVAAPCDAGV YPVVVFLHGY
   101    LAYNSFYSQL FEHVASHGFV VVGPQLYTMS GPDTTDEINS AAAVINWLAA
   151    GGLTSKLPPN VRADATKISI SGHSRGGKVA FALALGHANV SLRGGAGGAT
   201    IAALVAVDPV DGFAAGKQTP PPILTYGGAN SLRVPAPVMV IGTGLGGLAR
   251    AAPLLPACAP PGVSHGEFYG ECAAPACHLV ARDYGHTDMM DDVTPGARGL
   301    ATRAVCRSGG ARAPMRRFFG GAMVAFVKRW VEGEPELLDC VRARPETAPV
   351    VLSAVEFRDE AIANHSY
```

Figure 40 (SEQ ID NO:29)

```
ORYJ2_CHL
    1    MIAFAAQILA  FCLLLLLLLL  LQLQTTMAGD  SSFSGVFDHG  SHGVTLVKVD
   51    EAPRKCSSAA  AAKKTDDDTA  PAGGAPPKPL  LVAAPCDAGV  YPVVVFLHGY
  101    LAYNSFYSQL  FEHVASHGFV  VVGPQLFLGC  ELILSNNFDA  KMLYTMSGPD
  151    TTDEINSAAA  VINWLAAGGL  TSKLPPNVRA  DATKISISGH  SRGGKVAFAL
  201    ALGHANQTPR  PILTYGGANS  LRLPAPVMVI  GTGLGGLARA  APLLPACAPP
  251    GVSHGEFYGE  CAAPACHLVA  RDYGHTDMMD  DVTPGARGLA  TRAVCRSGGA
  301    RAPMRRFFGG  AMVAFVKRWV  EGEPELLDCV  RARPETAPVV  LSAVEFRDEA
  351    IANHSY
```

Figure 41 (SEQ ID NO:30)

```
PICEA_CHL
    1    MGQQGEEPWE  DVFKPGRFPV  RILKIPQRTT  HGSTTAAAPK  PLLLALPAQP
   51    GEYPVLLFFH  GYLLLNSFYT  QLLQHIASHG  YIAIAPQMYC  VTGADATPEI
  101    ADAAAICNWL  LQGLSSYLPD  DVRPDFQNVA  MAGHSRGGKV  AFGLALDRTS
  151    QTTELKFSAL  VGVDPVDGMA  RGRQTQPRIL  TYKPHSFDSV  IPTLIVGSGL
  201    GAVKRNPLFP  PCAPEGVSHR  EFFSECSAPA  YHFVASDYGH  MDFLDDETGG
  251    VKGQSSYCLC  KNGVAREPMR  RFCGGIIVAF  LNVCLQNDSG  AFNDLLVHPS
  301    HAPVKLEPPE  SFVSEVEHQA  VESLLPQTV
```

Figure 42 (SEQ ID NO:31)

```
CHL_CHL
    1    MPSTQFLGAS  TLLLFGLRAV  MSSDDYIKRG  DLPTSKWSGR  VTLRVDSAMA
   51    VPLDVVITYP  SSGAAAYPVL  VMYNGFQAKA  PWYRGIVDHV  SSWGYTVVQY
  101    TNGGLFPIVV  DRVELTYLEP  LLTWLETQSA  DAKSPLYGRA  DVSRLGTMGH
  151    SRGGKLAALQ  FAGRTDVSGC  VLFDPVDGSP  MTPESADYPS  ATKALAAAGR
  201    SAGLVGAAIT  GSCNPVGQNY  PKFWGALAPG  SWQMVLSQAG  HMQFARTGNP
  251    FLDWSLDRLC  GRGTMMSSDV  ITYSAAFTVA  WFEGIFRPAQ  SQMGISNFKT
  301    WANTQVAARS  ITFDIKPMQS  PQ
```

PROCESS MODIFICATIONS TO ENHANCE CHLOROPHYLL DEGRADATION

CROSS-REFERENCE TO RELATED APPLICATIONS

This application is the U.S. National Stage of International Application PCT/IB2012/050715 filed Feb. 16, 2012, which designates the U.S. and was published by the International Bureau in English on Aug. 30, 2012, and which claims the benefit of U.S. Provisional Application No. 61/445,665, filed Feb. 23, 2011, both of which are hereby incorporated by reference in their entirety.

FIELD

The present invention relates to the industrial processing of plant-derived food and feed products, especially vegetable oils. The invention may be employed to reduce or eliminate contamination by chlorophyll and chlorophyll derivatives.

BACKGROUND

Chlorophyll is a green-coloured pigment widely found throughout the plant kingdom. Chlorophyll is essential for photosynthesis and is one of the most abundant organic metal compounds found on earth. Thus many products derived from plants, including foods and feeds, contain significant amounts of chlorophyll.

For example, vegetable oils derived from oilseeds such as soybean, palm or rape seed (canola), cotton seed and peanut oil typically contain some chlorophyll. However the presence of high levels of chlorophyll pigments in vegetable oils is generally undesirable. This is because chlorophyll imparts an undesirable green colour and can induce oxidation of oil during storage, leading to a deterioration of the oil.

Various methods have been employed in order to remove chlorophyll from vegetable oils. Chlorophyll may be removed during many stages of the oil production process, including the seed crushing, oil extraction, degumming, caustic treatment and bleaching steps. However the bleaching step is usually the most significant for reducing chlorophyll residues to an acceptable level. During bleaching the oil is heated and passed through an adsorbent to remove chlorophyll and other colour-bearing compounds that impact the appearance and/or stability of the finished oil. The adsorbent used in the bleaching step is typically clay.

In the edible oil processing industry, the use of such steps typically reduces chlorophyll levels in processed oil to between 0.02 to 0.05 ppm. However the bleaching step increases processing cost and reduces oil yield due to entrainment in the bleaching clay. The use of clay may remove many desirable compounds such as carotenoids and tocopherol from the oil. Also the use of clay is expensive, this is particularly due to the treatment of the used clay (i.e. the waste) which can be difficult, dangerous (prone to self-ignition) and thus costly to handle. Thus attempts have been made to remove chlorophyll from oil by other means, for instance using the enzyme chlorophyllase.

In plants, chlorophyllase (chlase) is thought to be involved in chlorophyll degradation and catalyzes the hydrolysis of an ester bond in chlorophyll to yield chlorophyllide and phytol. WO 2006009676 describes an industrial process in which chlorophyll contamination can be reduced in a composition such as a plant oil by treatment with chlorophyllase. The water-soluble chlorophyllide which is produced in this process is also green in colour but can be removed by an aqueous extraction or silica treatment.

Chlorophyll is often partly degraded in the seeds used for oil production as well as during extraction of the oil from the seeds. One common modification is the loss of the magnesium ion from the porphyrin (chlorin) ring to form the derivative known as pheophytin (see FIG. 1). The loss of the highly polar magnesium ion from the porphyrin ring results in significantly different physico-chemical properties of pheophytin compared to chlorophyll. Typically pheophytin is more abundant in the oil during processing than chlorophyll. Pheophytin has a greenish colour and may be removed from the oil by an analogous process to that used for chlorophyll, for instance as described in WO 2006009676 by an esterase reaction catalyzed by an enzyme having a pheophytinase activity. Under certain conditions, some chlorophyllases are capable of hydrolyzing pheophytin as well as chlorophyll, and so are suitable for removing both of these contaminants. The products of pheophytin hydrolysis are the red/brown-colored pheophorbide and phytol. Pheophorbide can also be produced by the loss of a magnesium ion from chlorophyllide, i.e. following hydrolysis of chlorophyll (see FIG. 1). WO 2006009676 teaches removal of pheophorbide by an analogous method to chlorophyllide, e.g. by aqueous extraction or silica adsorption.

Pheophytin may be further degraded to pyropheophytin, both by the activity of plant enzymes during harvest and storage of oil seeds or by processing conditions (e.g. heat) during oil refining (see "Behaviour of Chlorophyll Derivatives in Canola Oil Processing", JAOCS, Vol, no. 9 (September 1993) pages 837-841). One possible mechanism is the enzymatic hydrolysis of the methyl ester bond of the isocyclic ring of pheophytin followed by the non-enzymatic conversion of the unstable intermediate to pyropheophytin. A 28-29 kDa enzyme from *Chenopodium album* named pheophorbidase is reportedly capable of catalyzing an analogous reaction on pheophorbide, to produce the phytol-free derivative of pyropheophytin known as pyropheophorbide (see FIG. 1). Pyropheophorbide is less polar than pheophorbide resulting in the pyropheophoribe having a decreased water solubility and an increased oil solubility compared with pheophorbide.

Depending on the processing conditions, pyropheophytin can be more abundant than both pheophytin and chlorophyll in vegetable oils during processing (see Table 9 in volume 2.2. of Bailey's Industrial Oil and Fat Products (2005), $6^{th}$ edition, Ed. by Fereidoon Shahidi, John Wiley & Sons). This is partly because of the loss of magnesium from chlorophyll during harvest and storage of the plant material. If an extended heat treatment at 90° C. or above is used, the amount of pyropheophytin in the oil is likely to increase and could be higher than the amount of pheophytin. Chlorophyll levels are also reduced by heating of oil seeds before pressing and extraction as well as the oil degumming and alkali treatment during the refining process. It has also been observed that phospholipids in the oil can complex with magnesium and thus reduce the amount of chlorophyll. Thus chlorophyll is a relatively minor contaminant compared to pyropheophytin (and pheophytin) in many plant oils.

Each of the four chlorophyll derivatives, chlorophyll a and b and pheophytin a and b, exist as a pair of epimers determined by the stereochemistry of H and $COOCH_3$ around the carbon number $13^2$ (numbering according to the IUPAC system, marked with asterisk in FIG. 2). Thus chlorophyll a exists as the pair of epimers chlorophyll a and chlorophyll a', and chlorophyll b comprises b and b' forms. Likewise pheophytin a comprises the epimer a and a' pair and pheophytin b comprises b and b' forms. The prime (')
forms have S-stereochemistry and non-prime forms have
R-stereochemistry about the carbon $13^2$ atom. Epimerization
of, for example, the a form to a' form and vice versa can take
place under certain conditions via a common enol, as
described in "Epimerization in the pheophytin a/a' system",
Chemistry letters (1984), 1411-1414. In solution there is
typically an equilibrium which dictates the distribution of
prime and non-prime chlorophyll compounds and this is
often determined by physical parameters such as temperature, pH, solvent and so on.

In general enzymes typically act as stereospecific catalysts by having activity on only one stereoisomer. Previous
analyses suggested that chlorophyllases possess a high
degree of stereospecificity only catalyzing the hydrolysis of
non-prime forms of chlorophyll compounds (see "The stereospecific interaction between chlorophylls and chlorophyllase" J. Biol. Chem. 267(31):22043-22047 (1992)).

In methods for the removal of chlorophyll and chlorophyll
derivatives from plant oil which employ chlorophyllases or
related enzymes, the stereospecificity of the enzyme may be
problematic. In particular, depending on the distribution and
equilibrium of the chlorophyll stereoisomers in the oil, a
complete degradation of chlorophyll components can be
very difficult. For instance, if a significant proportion of the
chlorophyll or chlorophyll derivative exists in the prime
form, this fraction of the chlorophyll derivatives present in
the oil may be resistant to enzymatic degradation. Moreover,
a number of enzymes show much lower activity on pyropheophytin than on, for example, pheophytin.

This problem with existing methods is illustrated in FIG.
3. FIG. 3 shows the epimerization of pheophytin a and the
conversion to pyropheophytin. The pH of a water/crude
plant oil mixture (e.g. comprising about 1-2% water) is
typically around 5.0 at about 60° C. Under such conditions,
in crude soy bean or rape seed oil the pheophytin a epimer
distribution is typically around 70% pheophytin a (R-stereoisomer) and 30% pheophytin a' (S-stereoisomer) and
isomerization between the two epimers is slow. Moreover,
variable amounts of pyropheophytin may be formed depending on reaction conditions. If the enzyme used in the reaction
is predominantly active only on pheophytin a, a significant
proportion of the chlorophyll derivatives present in the oil
cannot be hydrolyzed directly by the enzyme at unmodified
pH.

There is a therefore a need for an improved process for
removing chlorophyll and chlorophyll derivatives such as
pheophytin and pyropheophytin from plant oils. In particular, there is a need for a process which enhances the removal
of various forms of chlorophyll and chlorophyll derivatives
from the oil.

SUMMARY

In one aspect, the present invention provides a process for
treating a plant oil, comprising a step of contacting the oil
with an enzyme, wherein the enzyme is capable of hydrolysing an a' or b' stereoisomer of chlorophyll or a chlorophyll
derivative.

In one embodiment, the a' or b' stereoisomer comprises
chlorophyll a', pheophytin a', chlorophyll b' or pheophytin
b'. Preferably the stereoisomer is an a' stereoisomer of
chlorophyll or the chlorophyll derivative, e.g. chlorophyll a'
or pheophytin a'.

In one embodiment, the enzyme has an activity ratio on an
a stereoisomer of chlorophyll or a chlorophyll derivative,
compared to an a' stereoisomer of chlorophyll or the chlorophyll derivative, of less than 10, less than 5, or less than
2. In an alternative embodiment, the enzyme has an activity
ratio on a b stereoisomer of chlorophyll or a chlorophyll
derivative, compared to an b' stereoisomer of chlorophyll or
the chlorophyll derivative, of less than 10, less than 5, or less
than 2.

In one embodiment, following treatment with the enzyme
the oil comprises at least 50% a stereoisomers of chlorophyll
or the chlorophyll derivative, based on the total amount of
a and a' stereoisomers of chlorophyll or the chlorophyll
derivative in the oil. In an alternative embodiment, following treatment with the enzyme the oil comprises at least 50%
b stereoisomers of chlorophyll or the chlorophyll derivative,
based on the total amount of b and b' stereoisomers of
chlorophyll or the chlorophyll derivative in the oil.

In further embodiments, the enzyme has an activity ratio
on pheophytin compared to pyropheophytin of less than 10,
less than 8 or less than 5.

In further embodiments, the enzyme comprises chlorophyllase, pheophytinase and/or pyropheophytinase activity,
i.e. hydrolytic activity on chlorophyll, pheophytin and/or
pyropheophytin.

In further embodiments, the enzyme is derived from
*Arabidopsis thaliana* or *Ricinus communis*. For instance, the
enzyme may comprise a polypeptide sequence as defined in
SEQ ID NO:2 or SEQ ID NO:13, or a functional fragment
or variant thereof.

Preferably the enzyme comprises a polypeptide sequence
having at least 75% sequence identity to SEQ ID NO:2 or
SEQ ID NO:13 over at least 50 amino acid residues. In one
embodiment, the enzyme comprises a polypeptide having at
least 90% sequence identity to SEQ ID NO:2. In another
embodiment, the enzyme comprises a polypeptide having at
least 90% sequence identity to SEQ ID NO:13.

In a further aspect, the present invention provides a plant
oil obtainable by a method according to any preceding
claim.

In a further aspect, the present invention provides use of
an enzyme which is capable of hydrolysing chlorophyll or a
chlorophyll derivative, for removing an a' or b' stereoisomer
of chlorophyll or the chlorophyll derivative from a plant oil.

As described herein, enzymes have been identified which
surprisingly show hydrolytic activity on prime as well as
non-prime forms of chlorophyll derivatives. Moreover such
enzymes may also show increased hydrolytic activity on
pyropheophytin compared to enzymes used in known methods. Such enzymes can be advantageously used to enhance
the removal of various forms of chlorophyll derivatives from
plant oils.

BRIEF DESCRIPTION OF DRAWINGS

FIG. 3 shows epimerization of pheophytin a molecules
and conversion to pyropheophytin a.

FIG. 12 shows the amino acid sequence of an *Arabidopsis thaliana* chlorophyllase (SEQ ID NO:1).

FIG. 13 shows the amino acid sequence of an *Arabidopsis thaliana* chlorophyllase (SEQ ID NO:2).

FIG. 14 shows the amino acid sequence of *Citrus sinensis* chlorophyllase (SEQ ID NO:3).

FIG. 15 shows the amino acid sequence of a *Triticum aestivum* chlorophyllase (SEQ ID NO:4).

FIG. 16 shows the amino acid sequence of a *Triticum aestivum* chlorophyllase (SEQ ID NO:5).

FIG. 17 shows the amino acid sequence of a *Brassica oleracea* chlorophyllase (SEQ ID NO:6).

FIG. 18 shows the amino acid sequence of a *Brassica oleracea* chlorophyllase (SEQ ID NO:7).

FIG. 19 shows the amino acid sequence of a *Brassica oleracea* chlorophyllase (SEQ ID NO:8).

FIG. 20 shows the amino acid sequence of a *Zea Mays* chlorophyllase (SEQ ID NO:9).

FIG. 21 shows the amino acid sequence of a *Zea Mays* chlorophyllase (SEQ ID NO:10).

FIG. 22 shows the amino acid sequence of a *Phyllostachys edulis* chlorophyllase (SEQ ID NO:11).

FIG. 23 shows the amino acid sequence of a *Chenopodium album* chlorophyllase (SEQ ID NO:12).

FIG. 24 shows the amino acid sequence of a *Ricinus communis* chlorophyllase (SEQ ID NO:13).

FIG. 25 shows the amino acid sequence of a *Glycine max* chlorophyllase (SEQ ID NO:14).

FIG. 26 shows the amino acid sequence of a *Ginkgo biloba* chlorophyllase (SEQ ID NO:15).

FIG. 27 shows the amino acid sequence of a *Pachira macrocarpa* chlorophyllase (SEQ ID NO:16).

FIG. 28 shows the amino acid sequence of a *Populus trichocarpa* chlorophyllase (SEQ ID NO:17).

FIG. 29 shows the amino acid sequence of a *Sorghum bicolor* chlorophyllase (SEQ ID NO:18).

FIG. 30 shows the amino acid sequence of a *Sorghum bicolor* chlorophyllase (SEQ ID NO:19).

FIG. 31 shows the amino acid sequence of a *Vitis vinifera* chlorophyllase (SEQ ID NO:20).

FIG. 32 shows the amino acid sequence of a *Physcomitrella patens* chlorophyllase (SEQ ID NO:21).

FIG. 33 shows the amino acid sequence of a *Aquilegia* chlorophyllase (SEQ ID NO:22).

FIG. 34 shows the amino acid sequence of a *Brachypodium distachyon* chlorophyllase (SEQ ID NO:23).

FIG. 35 shows the amino acid sequence of a *Medicago truncatula* chlorophyllase (SEQ ID NO:24).

FIG. 36 shows the amino acid sequence of a *Piper betle* chlorophyllase (SEQ ID NO:25).

FIG. 37 shows the amino acid sequence of a *Lotus japonicus* chlorophyllase (SEQ ID NO:26).

FIG. 38 shows the amino acid sequence of a *Oryza sativa* Indica chlorophyllase (SEQ ID NO:27).

FIG. 39 shows the amino acid sequence of a *Oryza sativa* Japonica chlorophyllase (SEQ ID NO:28).

FIG. 40 shows the amino acid sequence of a *Oryza sativa* Japonica chlorophyllase (SEQ ID NO:29).

FIG. 41 shows the amino acid sequence of a *Picea sitchensis* chlorophyllase (SEQ ID NO:30).

FIG. 42 shows the amino acid sequence of a *Chlamydomonas* chlorophyllase (SEQ ID NO:31).

FIG. 49 shows an HPLC chromatogram using absorbance detection (430 nm) indicating numbered peaks associated with: 1=chlorophyllide b; 2=chlorophyllide a; 3=neoxanthin; 3'=neoxanthin isomer; 4=neochrome; 5=violaxanthin; 6=luteoxanthin; 7=auroxanthin; 8=anteraxanthin; 8'=anteraxanthin isomer; 9=mutatoxanthin; 10=lutein; 10'=lutein isomer; 10"=lutein isomer; 11=pheophorbide b; 12=pheophorbide a; 13=chlorophyll b; 13'=chlorophyll b'; 14=chlorophyll a; 14'=chlorophyll a'; 15=pheopytin b; 15'=pheophytin b'; 16=13-carotene; 17=pheophytin a; 17'=pheophytin a'; 18=pyropheophytin b; 19=pyropheophytin a.

DETAILED DESCRIPTION

In one aspect the present invention relates to a process for treating a plant oil. Typically the process is used to remove chlorophyll and/or chlorophyll derivatives from the oil, or to reduce the level of chlorophyll and/or chlorophyll derivatives in the oil, for instance where the chlorophyll and/or chlorophyll derivatives are present as a contaminant.

Chlorophyll and Chlorophyll Derivatives

By "chlorophyll derivative" it is typically meant compounds which comprise both a porphyrin (chlorin) ring and a phytol group (tail), including magnesium-free phytol-containing derivatives such as pheophytin and pyropheophytin. Chlorophyll and (phytol-containing) chlorophyll derivatives are typically greenish is colour, as a result of the porphyrin (chlorin) ring present in the molecule. Loss of magnesium from the porphyrin ring means that pheophytin and pyropheophytin are more brownish in colour than chlorophyll. Thus the presence of chlorophyll and chlorophyll derivatives in an oil, can give such an oil an undesirable green, greenish or brownish colour. In one embodiment, the present process may be performed in order to remove or reduce the green or brown colouring present in the oil. Accordingly the present process may be referred to as a bleaching or de-colorizing process.

Enzymes used in the process may hydrolyse chlorophyll and phytol-containing chlorophyll derivatives to cleave the phytol tail from the chlorin ring. Hydrolysis of chlorophyll and chlorophyll derivatives typically results in compounds such as chlorophyllide, pheophorbide and pyropheophorbide which are phytol-free derivatives of chlorophyll. These compounds still contain the colour-bearing porphyrin ring, with chlorophyllide being green and pheophorbide and pyropheophorbide a reddish brown colour. In some embodiments, it may also be desirable to remove these phytol-free derivatives and to reduce the green/red/brown colouring in the oil. Thus in one embodiment of the invention, the process may further comprise a step of removing or reducing the level of phytol-free chlorophyll derivatives in the oil. The process may involve bleaching or de-colorizing to remove the green and/or red/brown colouring of the oil.

The chlorophyll or chlorophyll derivative may be either a or b forms. Thus as used herein, the term "chlorophyll" includes chlorophyll a and chlorophyll b. In a similar way both a and b forms are covered when referring to pheophytin, pyropheophytin, chlorophyllide, pheophorbide and pyropheophorbide.

Figure 2:
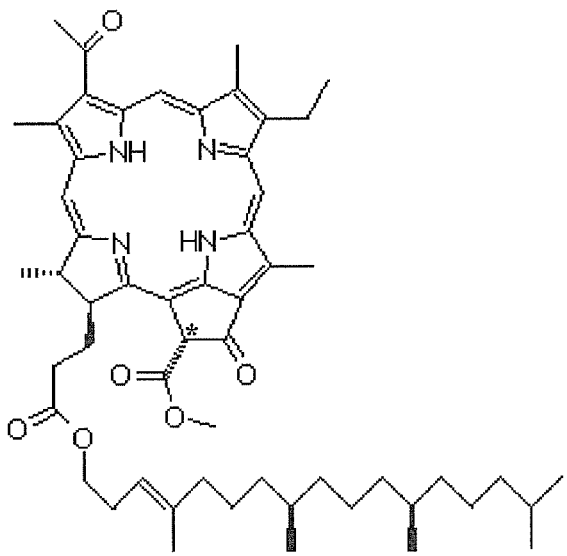
FIG. 2 shows pheophytin a, where the C-$13^2$ according to
the IUPAC numbering system is marked with an asterisk.
Figure 3:
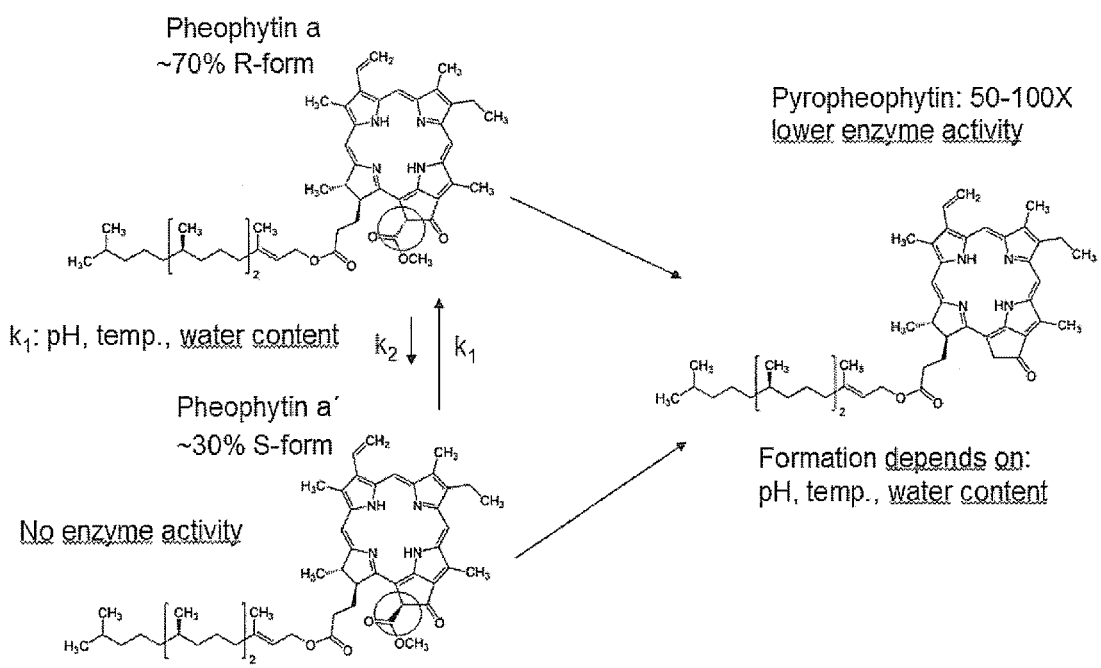

As described herein, chlorophyll and chlorophyll derivatives may exist as a pair of epimers determined by the stereochemistry around the carbon number $13^2$ (numbering according to the IUPAC system, marked with asterisk in FIG. 2). Thus chlorophyll a exists as the pair of epimers chlorophyll a and chlorophyll a', and chlorophyll b comprises b and b' forms. Pheophytin a comprises the epimers a and a' and pheophytin b comprises b and b' forms. The prime (') forms have S-stereochemistry and non-prime forms have R-stereochemistry about the carbon $13^2$ atom. When used generally herein, the term "chlorophyll and chlorophyll derivatives" includes both prime and non-prime forms.

Plant Oils

Any plant oil may be treated according to the present process, in order to remove undesirable contamination by chlorophyll and/or chlorophyll derivatives. The oil may be derived from any type of plant, and from any part of a plant, including whole plants, leaves, stems, flowers, roots, plant protoplasts, seeds and plant cells and progeny of same. The class of plants from which products can be treated in the method of the invention includes higher plants, including angiosperms (monocotyledonous and dicotyledonous plants), as well as gymnosperms. It includes plants of a variety of ploidy levels, including polyploid, diploid, haploid and hemizygous states.

In preferred embodiments, the oil may comprise a vegetable oil, including oils processed from oil seeds or oil fruits (e.g. seed oils such as canola (rapeseed) oil and fruit oils such as palm). Examples of suitable oils include rice bran, soy, canola (rape seed), palm, olive, cottonseed, corn, palm kernel, coconut, peanut, sesame, Moringa or sunflower. The process of the invention can be used in conjunction with methods for processing essential oils, e.g., those from fruit seed oils, e.g. grapeseed, apricot, borage, etc. The process of the invention can be used in conjunction with methods for processing high phosphorus oils (e.g. a soy bean oil). Preferably the oil is a crude plant oil.

Chlorophyll and Chlorophyll Derivatives in Oil

The chlorophyll and/or chlorophyll derivatives (e.g. chlorophyll, pheophytin and/or pyropheophytin) may be present in the oil naturally, as a contaminant, or as an undesired component in a processed product. The chlorophyll and/or chlorophyll derivatives (e.g. chlorophyll, pheophytin and/or pyropheophytin) may be present at any level in the oil. Typically chlorophyll, pheophytin and/or pyropheophytin may be present as a natural contaminant in the oil at a concentration of 0.001 to 1000 mg/kg (0.001 to 1000 ppm, $10^{-7}$ to $10^{-1}$ wt %), based on the total weight of the oil. In further embodiments, the chlorophyll and/or chlorophyll derivatives may be present in the oil at a concentration of 0.1 to 100, 0.5 to 50, 1 to 50, 1 to 30 or 1 to 10 mg/kg, based on the total weight of the oil.

Phytol-free chlorophyll derivatives may also be present in the oil. For instance, chlorophyllide, pyropheophorbide and/or pyropheophorbide may be present at any level in the oil. Typically chlorophyllide, pyropheophorbide and/or pyropheophorbide may be present in the oil, either before or after treatment with an enzyme according to the method of the present invention, at a concentration of 0.001 to 1000 mg/kg (0.001 to 1000 ppm, $10^{-7}$ to $10^{-1}$ wt %), based on the total weight of the oil. In further embodiments, the chlorophyllide, pyropheophorbide and/or pyropheophorbide may be present in the composition at a concentration of 0.1 to 100, 0.5 to 50, 1 to 50, 1 to 30 or 1 to 10 mg/kg, based on the total weight of the composition.

Enzymes Hydrolysing Chlorophyll or a Chlorophyll Derivative

The process of the present invention comprises a step of contacting the oil with an enzyme which is capable of hydrolysing chlorophyll or a chlorophyll derivative, particularly prime stereoisomers (e.g. a' or b') thereof. Typically "hydrolyzing chlorophyll or a chlorophyll derivative" means hydrolysing an ester bond in chlorophyll or a (phytol-containing) chlorophyll derivative, e.g. to cleave a phytol group from the chlorin ring in the chlorophyll or chlorophyll derivative. Thus the enzyme typically has an esterase or hydrolase activity. Preferably the enzyme has esterase or hydrolase activity in an oil phase, and optionally also in an aqueous phase.

Thus the enzyme may, for example, be a chlorophyllase, pheophytinase or pyropheophytinase. Preferably, the enzyme is capable of hydrolysing at least one, at least two or all three of chlorophyll, pheophytin and pyropheophytin. In a particularly preferred embodiment, the enzyme has chlorophyllase, pheophytinase and pyropheophytinase activity. In further embodiments, two or more enzymes may be used in the method, each enzyme having a different substrate specificity. For instance, the method may comprise the combined use of two or three enzymes selected from a chlorophyllase, a pheophytinase and a pyropheophytinase.

Any polypeptide having an activity that can hydrolyse chlorophyll or a chlorophyll derivative, and in particular prime stereoisomers thereof, can be used as the enzyme in the process of the invention. By "enzyme" it is intended to encompass any polypeptide having hydrolytic activity on prime stereoisomers (e.g. a' or b∝) of chlorophyll or a chlorophyll derivative, including e.g. enzyme fragments, etc. Any isolated, recombinant or synthetic or chimeric (or a combination of synthetic and recombinant) polypeptide can be used.

In embodiments of the present invention, the enzyme is capable of hydrolysing an a' or b' stereoisomer of chlorophyll or a chlorophyll derivative. By this it is meant that the enzyme has hydrolytic activity on a prime (') form of chlorophyll or a chlorophyll derivative. The prime (') designation refers to the stereochemistry around the carbon number $13^2$ in chlorophyll or the chlorophyll derivative.

Thus prime forms of chlorophyll or chlorophyll derivatives which may be hydrolysed in embodiments of the present invention include chlorophyll a', chlorophyll b', pheophytin a' and pheophytin b'. Preferably the enzyme is capable of hydrolyzing at least a prime form of an a type chlorophyll derivative, i.e. chlorophyll a' or pheophytin a'.

Typically the enzyme also has hydrolytic activity on non-prime forms of chlorophyll or chlorophyll derivatives. The enzymes used in the present invention may have reduced stereospecificity, i.e. the enzymes used herein are less specific for non-prime forms of chlorophyll or chlorophyll derivatives than other known chlorophyllases (such as *Triticum aestivum* chlorophyllase, see SEQ ID NO:4).

In one embodiment, the enzyme has an activity ratio on a non-prime (e.g. a or b) stereoisomer of chlorophyll or a chlorophyll derivative, compared to a prime (e.g. a' or b') stereoisomer of chlorophyll or the chlorophyll derivative, of less than 100. Preferably the activity ratio is less than 50, less than 10, less than 5, less than 3, less than 2, less than 1.5, less than 1 or less than 0.5. By "activity ratio" it is meant to refer to the relative activity of the enzyme on the prime form compared to the non-prime form under the same conditions. Thus the activity ratio may be determined by determining (a) hydrolytic activity of the enzyme on a non-prime stereoisomer, and (b) hydrolytic activity of the enzyme on a corresponding prime stereoisomer, and dividing (a) by (b). A low activity ratio is thus indicative of a relatively high activity on prime forms.

Hydrolytic activity may be determined, for example, using methods described below. Typically the activity ratio may be determined under conditions which do not favour epimerization (i.e. transition between prime and non-prime isomers). For instance, the activity ratio may be determined by measuring hydrolytic activity on prime and non-prime isomers in a crude oil with greater than 0.5 ppm pheophytin, about 2% water and at pH 5.0 to 5.5. In one embodiment, the hydrolytic activity of the enzyme on pheophytin a or pheophytin a' is calculated at half of the original substrate concentration (see e.g. Example 4)

In another embodiment, the enzyme has an activity ratio on pheophytin compared to pyropheophytin of less than 80, less than 50, less than 10, less than 8, less than 7 or less than 5. For example, the enzyme may have a pheophytinase to pyropheophytinase activity ratio of 0.1 to 10, 1 to 10 or 1 to 5. The pheophytinase to pyropheophytinase activity ratio may be calculated by determining pheophytinase activity and pyropheophytinase activity under the same conditions using methods described below, and dividing the pheophytinase activity by the pyropheophytinase activity. Activity ratios within the above ratios may be determined in respect of corresponding species of pheophytin and pyropheophytin, e.g. pheophytin a (comprising both a and a' forms) to pyropheopytin a.

Enzyme (Chlorophyllase, Pheophytinase or Pyropheophytinase) Activity Assay

Hydrolytic activity on chlorophyll or a chlorophyll derivative, including on prime and non-prime forms thereof, may be detected using any suitable assay technique, for example based on an assay described herein. For example, hydrolytic activity may be detected using fluorescence-based techniques. In one suitable assay, a polypeptide to be tested for hydrolytic activity on chlorophyll or a chlorophyll derivative is incubated in the presence of a substrate, and product or substrate levels are monitored by fluorescence measurement. Suitable substrates include e.g. chlorophyll, pheophytin and/or pyropheophytin, including a and b and prime and non-prime forms thereof. Products which may be detected include chlorophyllide, pheophorbide, pyropheophorbide and/or phytol.

Assay methods for detecting hydrolysis of chlorophyll or a chlorophyll derivative are disclosed in, for example, Ali Khamessan et al. (1994), Journal of Chemical Technology & Biotechnology, 60(1), pages 73-81; Klein and Vishniac (1961), J. Biol. Chem. 236: 2544-2547; and Kiani et al. (2006), Analytical Biochemistry 353: 93-98.

Figure 49:
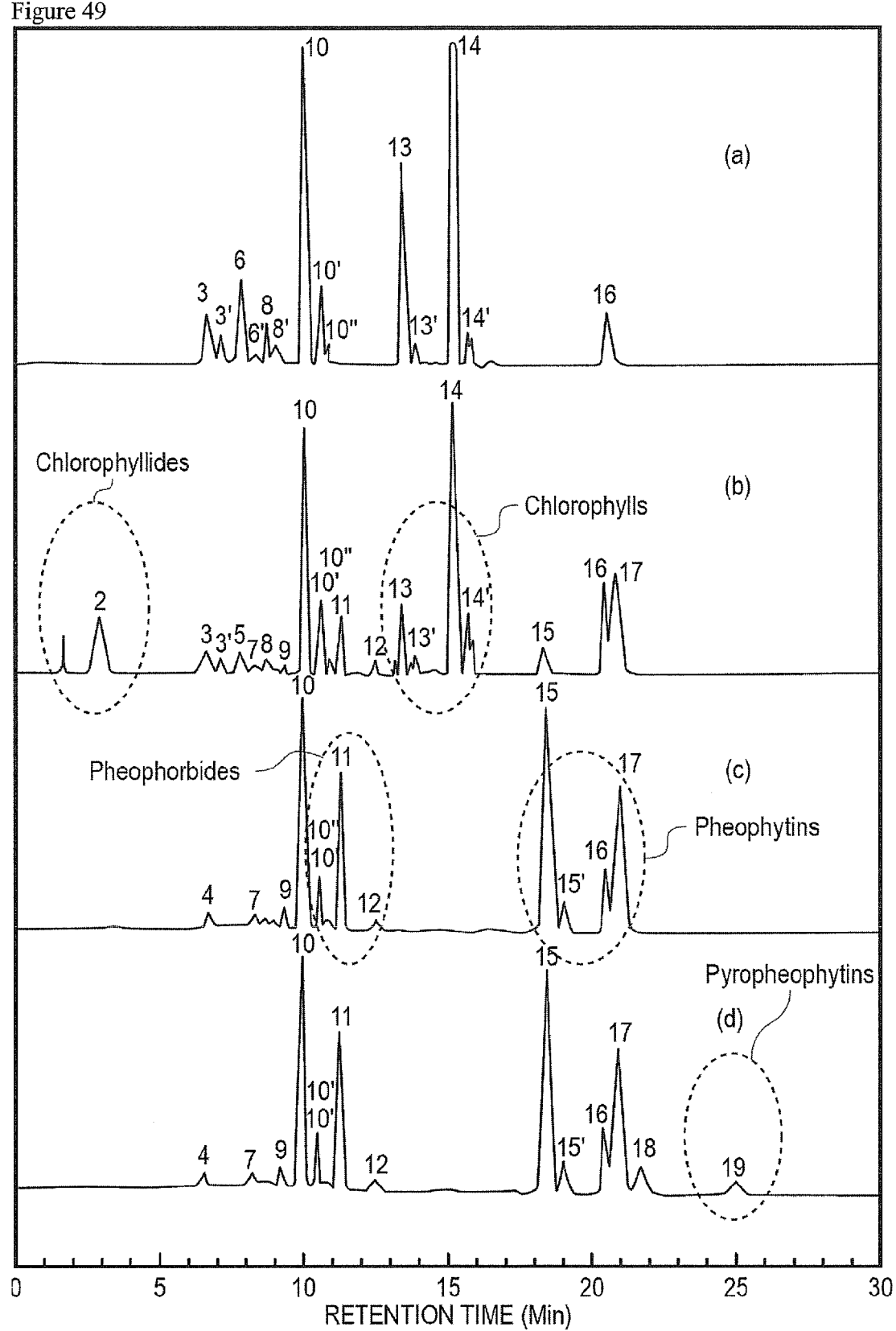

Alternatively, a suitable assay may be based on HPLC detection and quantitation of substrate or product levels following addition of a putative enzyme, e.g. based on the techniques described below. In one embodiment, the assay may be performed as described in Hornero-Mendez et al. (2005), Food Research International 38(8-9): 1067-1072. In another embodiment, the following assay may be used:

170 µl mM HEPES, pH 7.0 is added 20 µl 0.3 mM chlorophyll, pheophytin or pyropheophytin dissolved in acetone. The enzyme is dissolved in 50 mM HEPES, pH 7.0. 10 µl enzyme solution is added to 190 µl substrate solution to initiate the reaction and incubated at 40° C. for various time periods. The reaction was stopped by addition of 350 µl acetone. Following centrifugation (2 min at 18,000 g) the supernatant was analyzed by HPLC, and the amounts of (i) chlorophyll and chlorophyllide (ii) pheophytin and pheophorbide or (iii) pyropheophytin and pyropheophorbide determined. Prime and non-prime forms of chlorophyll and chlorophyll derivatives may be distinguished by HPLC analysis, as shown in FIG. 49.

One unit of enzyme activity is defined as the amount of enzyme which hydrolyzes one micromole of substrate (e.g. chlorophyll, pheophytin or pyropheophytin) per minute at 40° C., e.g. in an assay method as described herein.

In preferred embodiments, the enzyme used in the present method has chlorophyllase, pheophytinase and/or pyropheophytinase activity of at least 1000 U/g, at least 5000 U/g, at least 10000 U/g, or at least 50000 U/g, based on the units of activity per gram of the purified enzyme, e.g. as determined by an assay method described herein. Preferably the enzyme has a hydrolytic activity of at least 1000 U/g, at least 5000 U/g, at least 10000 U/g, or at least 50000 U/g, based on the units of activity per gram of the purified enzyme, on a prime (e.g. a' or b') stereoisomer of chlorophyll or a chlorophyll derivative (e.g. chlorophyll a', chlorophyll b', pheophytin a' or pheophytin b').

In a further embodiment, hydrolytic activity on chlorophyll or a chlorophyll derivative may be determined using a method as described in EP10159327.5.

Chlorophyllases

In one embodiment, the enzyme is capable of hydrolyzing at least a prime (e.g. a' or b') stereoisomer of chlorophyll. A polypeptide that catalyses the hydrolysis of a chlorophyll a' or b' ester bond to yield chlorophyllide a' or b' and phytol can be used in the process. In one embodiment the enzyme is a chlorophyllase classified under the Enzyme Nomenclature classification (E.C. 3.1.1.14). An isolated, recombinant or synthetic or chimeric (a combination of synthetic and recombinant) polypeptide (e.g., enzyme or catalytic antibody) can be used, see e.g. Marchler-Bauer (2003) Nucleic Acids Res. 31: 383-387.

In one embodiment, the enzyme may be derived from *Arabidopsis thaliana*. For instance, the enzyme may be a polypeptide comprising the sequence of SEQ ID NO:2 (see FIG. 13).

In another embodiment, the chlorophyllase is derived from castor bean, e.g. from *Ricinus communis*. For example, the chlorophyllase may be polypeptide comprising the sequence of SEQ ID NO:13 (see FIG. 24).

Further provided herein are enzymes comprising a polypeptide sequence as defined in any one of SEQ ID NO:s 1 to 31, as well as functional fragments and variants thereof, as described below.

Variants and Fragments

Functional variants and fragments of known sequences which hydrolyse prime forms is of chlorophyll or a chlorophyll derivative may also be employed in the present invention. By "functional" it is meant that the fragment or variant retains a detectable hydrolytic activity on a prime (e.g. a' or b') stereoisomer of chlorophyll or a chlorophyll derivative. Typically such variants and fragments show homology to a source chlorophyllase, pheophytinase or pyropheophytinase sequence, e.g. at least about 50%, 60%, 70%, 75%, 80%, 85%, 90%, 95%, 96%, 97%, 98%, 99%, or more sequence identity to a source chlorophyllase, pheophytinase or pyropheophytinase amino acid sequence, e.g. to SEQ ID NO:2 or SEQ ID NO: 13, e.g. over a region of at least about 10, 20, 30, 50, 100, 200, 300, 500, or 1000 or more residues, or over the entire length of the sequence.

The percentage of sequence identity may be determined by analysis with a sequence comparison algorithm or by a visual inspection. In one aspect, the sequence comparison algorithm is a BLAST algorithm, e.g., a BLAST version 2.2.2 algorithm.

Other enzymes having activity on prime forms of chlorophyll or a chlorophyll derivative suitable for use in the process may be identified by determining the presence of conserved sequence motifs present e.g. in known chlorophyllase, pheophytinase or pyropheophytinase sequences. For example, the motif GHSRG (SEQ ID NO: 32) containing the Ser active site is highly conserved in chlorophyllase sequences. In some embodiments, an enzyme for use in the present invention may comprise such a sequence. Polypeptide sequences having suitable activity may be identified by searching genome databases, e.g. the microbiome metagenome database (JGI-DOE, USA), for the presence of these motifs.

Isolation and Production of Enzymes

Enzymes for use in the present invention may be isolated from their natural sources or may be, for example, produced using recombinant DNA techniques. Nucleotide sequences encoding polypeptides having chlorophyllase, pheophytinase and/or pyropheophytinase activity may be isolated or constructed and used to produce the corresponding polypeptides.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

Typically, the nucleotide sequence encoding a polypeptide having chlorophyllase, pheophytinase and/or pyropheophytinase activity is prepared using recombinant DNA techniques. However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Modification of Enzyme Sequences

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites. A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of enzymes which hydrolyse chlorophyll and/or chlorophyll derivatives with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of enzymes with preferred characteristics. Suitable methods for performing 'shuffling' can be found in EP0752008, EP1138763, EP1103606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known chlorophyllase, pheophytinase or pyropheophytinase enzymes, but have very low amino acid sequence homology.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate.

As will be apparent to a person skilled in the art, using molecular evolution tools an enzyme may be altered to improve the functionality of the enzyme. Suitably, a nucleotide sequence encoding an enzyme (e.g. a chlorophyllase, pheophytinase and/or pyropheophytinase) used in the invention may encode a variant enzyme, i.e. the variant enzyme may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, or 99% identity with the parent enzyme. Suitable parent enzymes may include any enzyme with hydrolytic activity on prime forms of chlorophyll and/or a chlorophyll derivative.

Polypeptide Sequences

The present invention also encompasses the use of amino acid sequences encoded by a nucleotide sequence which encodes an enzyme for use in any one of the methods and/or uses of the present invention.

As used herein, the term "amino acid sequence" is synonymous with the term "polypeptide" and/or the term "protein". In some instances, the term "amino acid sequence" is synonymous with the term "peptide". The amino acid sequence may be prepared/isolated from a suitable source, or it may be made synthetically or it may be prepared by use of recombinant DNA techniques. Suitably, the amino acid sequences may be obtained from the isolated polypeptides taught herein by standard techniques.

One suitable method for determining amino acid sequences from isolated polypeptides is as follows. Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours. The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Comparison

Here, the term "homologue" means an entity having a certain homology with the subject amino acid sequences and the subject nucleotide sequences. Here, the term "homology" can be equated with "identity". The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences. % homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI Advance™ 11 (Invitrogen Corp.). Examples of other software that can perform sequence comparisons include, but are not limited to, the BLAST package (see Ausubel et al 1999 Short Protocols in Molecular Biology, 4th Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI Advance™ 11 program. A new tool, called BLAST 2 Sequences is also available for comparing protein and nucleotide sequence (see FEMS Microbiol Lett 1999 174(2): 247-50; and FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI Advance™ 11 package.

Alternatively, percentage homologies may be calculated using the multiple alignment feature in Vector NTI Advance™ 11 (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should Gap Penalties be used when determining sequence identity, then preferably the default parameters for the programme are used for pairwise alignment. For example, the following parameters are the current default parameters for pairwise alignment for BLAST 2:

| FOR BLAST2 | DNA | PROTEIN |
|---|---|---|
| EXPECT THRESHOLD | 10 | 10 |
| WORD SIZE | 11 | 3 |
| SCORING PARAMETERS | | |
| Match/Mismatch Scores | 2, −3 | n/a |
| Matrix | n/a | BLOSUM62 |
| Gap Costs | Existence: 5 Extension: 2 | Existence: 11 Extension: 1 |

In one embodiment, preferably the sequence identity for the nucleotide sequences and/or amino acid sequences may be determined using BLAST2 (blastn) with the scoring parameters set as defined above.

For the purposes of the present invention, the degree of identity is based on the number of sequence elements which are the same. The degree of identity in accordance with the present invention for amino acid sequences may be suitably determined by means of computer programs known in the art such as Vector NTI Advance™ 11 (Invitrogen Corp.). For pairwise alignment the scoring parameters used are preferably BLOSUM62 with Gap existence penalty of 11 and Gap extension penalty of 1.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Suitably, the degree of identity with regard to a nucleotide sequence may be determined over the whole sequence.

Amino Acid Mutations

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
|  |  | I L V |
|  | Polar - uncharged | C S T M |
|  |  | N Q |
|  | Polar - charged | D E |
|  |  | K R |
| AROMATIC |  | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide Sequences

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in plant cells, may be obtained and such homologues and fragments thereof in general will be capable of selectively hybridising to the sequences shown in the sequence listing herein. Such sequences may be obtained by probing cDNA libraries made from or genomic DNA libraries from other plant species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the enzyme sequence which it is desired to clone, bringing the primers into contact with mRNA or cDNA obtained from a plant cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Enzyme Formulation and Dosage

Enzymes used in the methods of the invention can be formulated or modified, e.g., chemically modified, to enhance oil solubility, stability, activity or for immobilization. For example, enzymes used in the methods of the invention can be formulated to be amphipathic or more lipophilic. For example, enzymes used in the methods of the invention can be encapsulated, e.g., in liposomes or gels, e.g., alginate hydrogels or alginate beads or equivalents. Enzymes used in the methods of the invention can be formulated in micellar systems, e.g., a ternary micellar (TMS) or reverse micellar system (RMS) medium. Enzymes used in the methods of the invention can be formulated as described in Yi (2002) J. of Molecular Catalysis B: Enzymatic, Vol. 19, pgs 319-325.

The enzymatic reactions of the methods of the invention, e.g. the step of contacting the oil with an enzyme which hydrolyses a prime (e.g. a' or b) stereoisomer of chlorophyll or a chlorophyll derivative, can be done in one reaction vessel or multiple vessels. In one aspect, the enzymatic reactions of the methods of the invention are done in a vegetable oil refining unit or plant.

The method of the invention can be practiced with immobilized enzymes, e.g. an immobilized chlorophyllase, pheophytinase and/or pyropheophytinase. The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents. In various aspects of the invention, immobilization of the enzyme can be optimized by physical adsorption on to the inorganic support. Enzymes used to practice the invention can be immobilized in different media, including water, Tris-HCl buffer solution and a ternary micellar system containing Tris-HCl buffer solution, hexane and surfactant. The enzyme can be immobilized to any type of substrate, e.g. filters, fibers, columns, beads, colloids, gels, hydrogels, meshes and the like.

The enzyme may be dosed into the oil in any suitable amount. For example, the enzyme may be dosed in a range of about 0.001 to 10 U/g of the composition, preferably 0.01 to 1 U/g, e.g. 0.01 to 0.1 U/g of the oil. One unit is defined as the amount of enzyme which hydrolyses 1 μmol of substrate (e.g. chlorophyll a or b, pheophytin a or b and/or pyropheophytin a or b, or a prime (e.g. a' or b') stereoisomer thereof) per minute at 40° C., e.g. under assay conditions as described in J. Biol. Chem. (1961) 236: 2544-2547.

Enzyme Reaction Conditions

In general the oil may be incubated (or admixed) with the enzyme between about 5° C. to and about 100° C., more preferably between 10° C. to about 90° C., more preferably between about 15° C. to about 80° C., more preferably between about 20° C. to about 75° C.

At higher temperatures pheophytin is decomposed to pyropheophytin, which is generally less preferred because some chlorophyllases are less active on pyropheophytin compared to pheophytin. In addition, the chlorophyllase degradation product of pyropheophytin, pyropheophorbide, is less water soluble compared to pheophorbide and thus more difficult to remove from the oil afterwards. The enzymatic reaction rate is increased at higher temperatures but it is favourable to keep the conversion of pheophytin to pyropheophytin to a minimum.

In view of the above, in particularly preferred embodiments the oil is incubated with the enzyme at below about 80° C., preferably below about 70° C., preferably at about 68° C. or below, preferably at about 65° C. or below, in order to reduce the amount of conversion to pyropheophytin. However, in order to keep a good reaction rate it is preferred to keep the temperature of the oil above 50° C. during incubation with the enzyme. Accordingly preferred temperature ranges for the incubation of the enzyme with the oil include about 50° C. to below about 70° C., about 50° C. to about 65° C. and about 55° C. to about 65° C.

Preferably the temperature of the oil may be at the desired reaction temperature when the enzyme is admixed therewith. The oil may be heated and/or cooled to the desired temperature before and/or during enzyme addition. Therefore in one embodiment it is envisaged that a further step of the process according to the present invention may be the cooling and/or heating of the oil.

Suitably the reaction time (i.e. the time period in which the enzyme is incubated with the oil), preferably with agitation, is for a sufficient period of time to allow hydrolysis of chlorophyll and chlorophyll derivatives, especially prime (e.g. a' or b) stereoisomers thereof, to form e.g. phytol and chlorophyllide, pheophorbide and/or pyropheophorbide. For example, the reaction time may be at least about 1 minute, more preferable at least about 5 minutes, more preferably at least about 10 minutes. In some embodiments the reaction time may be between about 15 minutes to about 6 hours, preferably between about 15 minutes to about 60 minutes, preferably about 30 to about 120 minutes. In some embodiments, the reaction time may up to 6 hours.

Preferably the process is carried out between about pH 4.0 and about pH 10.0, more preferably between about pH 5.0 and about pH 10.0, more preferably between about pH 6.0 and about pH 10.0, more preferably between about pH 5.0 and about pH 7.0, more preferably between about pH 5.0 and about pH 7.0, more preferably between about pH 6.5 and about pH 7.0, e.g. at about pH 7.0 (i.e. neutral pH). In one embodiment preferably the process is carried out between about pH 5.5 and pH 6.0.

Suitably the water content of the oil when incubated (or admixed) with the enzyme is between about 0.5 to about 5% water, more preferably between about 1 to about 3% and more preferably between about 1.5 and about 2%.

When an immobilised enzyme is used, suitably the water activity of the immobilised enzyme may be in the range of about 0.2 to about 0.98, preferably between about 0.4 to about 0.9, more preferably between about 0.6 to about 0.8.

Oil Separation

Following an enzymatic treatment step using an enzyme according to the present invention, in one embodiment the treated liquid (e.g. oil) is separated with an appropriate means such as a centrifugal separator and the processed oil is obtained. Upon completion of the enzyme treatment, if necessary, the processed oil can be additionally washed with water or organic or inorganic acid such as, e.g., acetic acid, citric acid, phosphoric acid, succinic acid, and the like, or with salt solutions.

Chlorophyll and/or Chlorophyll Derivative Removal

The process of the present invention involving an enzyme treatment typically reduces the level of chlorophyll and/or chlorophyll derivatives in the oil, especially prime (e.g. a' or b') stereoisomers thereof. For example, the process may reduce the concentration of chlorophyll a or b, pheophytin a or b and/or pyropheophytin a or b, or prime (e.g. a' or b') stereoisomers thereof by at least 5%, at least 10%, at least 20%, at least 30%, at least 40%, at least 50%, at least 60%, at least 70%, at least 80%, at least 90%, at least 95% or at least 99%, compared to the concentration of chlorophyll, pheophytin and/or pyropheophytin (by weight) present in the oil before treatment. Thus in particular embodiments, the concentration of chlorophyll and/or chlorophyll derivatives, or prime (e.g. a' or b') stereoisomers thereof, in the oil after treatment may be less than 100, less than 50, less than 30, less than 10, less than 5, less than 1, less than 0.5, less than 0.1 mg/kg or less than 0.02 mg/kg, based on the total weight of the oil.

Figure 48:
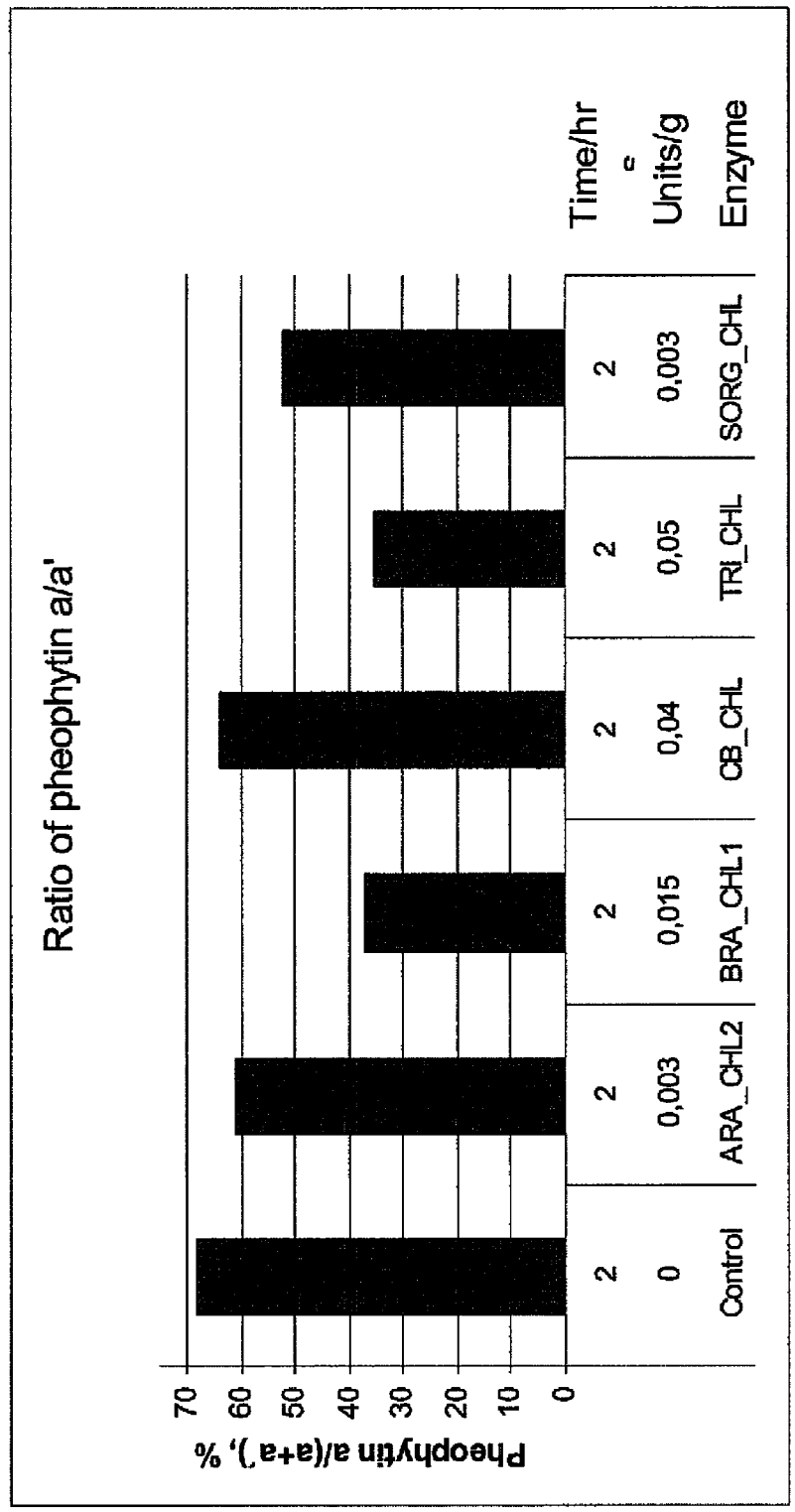
FIG. 48 shows the percentage of a stereoisomers of pheophytin in an oil sample after treatment with recombinant enzymes derived from various species, based on the total amount of pheophytin a and pheophytin a' stereoisomers in the oil sample after treatment.

If an enzyme which is stereospecific for non-prime forms of chlorophyll or chlorophyll derivatives is used, following treatment with the enzyme the oil typically comprises a reduced proportion of non-prime stereoisomers, compared to the total amount of non-prime and prime stereoisomers remaining in the oil (see Example 3 and FIG. 48 below). In contrast, in embodiments of the present invention, the enzymes used in the present method typically have reduced stereospecificity for non-prime forms of chlorophyll and chlorophyll derivatives, i.e. the enzymes are typically capable of hydrolyzing both prime and non-prime forms. Consequently following a treatment step of the present invention, the proportion of non-prime stereoisomers remaining in the oil typically falls less than when a stereospecific enzyme is used.

It has been found that under typical conditions, crude oils (e.g. crude soy bean oil or rape seed oil) may comprise around 70% non-prime (e.g. pheophytin a) and 30% prime (e.g. pheophytin a') stereoisomers. In one embodiment, following treatment with the enzyme the oil comprises at least 50% non-prime (e.g. a and/or b) stereoisomers of chlorophyll or the chlorophyll derivative, based on the total amount of non-prime (e.g. a and/or b) and prime (e.g. a' and/or a') stereoisomers of chlorophyll or the chlorophyll derivative in the oil. More preferably, the oil comprises at least 55%, at least 60% or at least 65% non-prime stereoisomers of chlorophyll or the chlorophyll derivative after treatment.

In one embodiment, following treatment with the enzyme the oil comprises at least 50%, at least 60% or at least 65% pheophytin a, based on the total amount of pheophytin a and pheophytin a' in the oil. In one embodiment, following treatment with the enzyme the oil comprises at least 50%, at least 60% or at least 65% pheophytin b, based on the total amount of pheophytin b and pheophytin b' in the oil.

In these embodiments, typical conditions may be, for example, about 20° C. to about 70° C. (e.g. about 40° C. or about 60° C.), pH 5 to 8 (e.g. about pH 6.0 or about pH 7.0) and water content of 1 to 3% (e.g. about 2%). The treatment time may comprise, for example, at least 1 hour, preferably 2 hours or more, more preferably 4 hours or more.

Further Processing Steps

Figure 50:
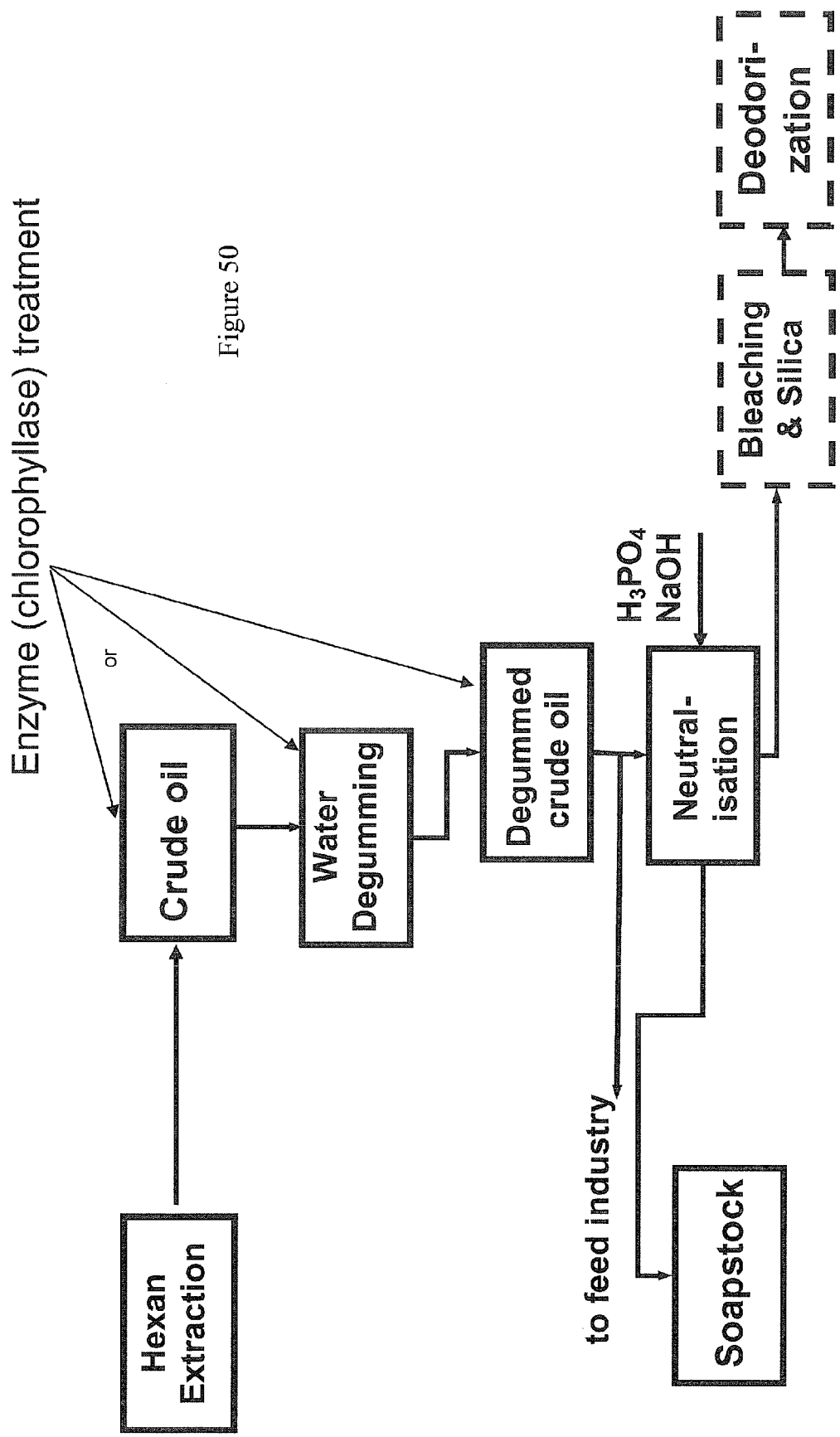
FIG. 50 shows a diagrammatic representation of an oil refining process according to an embodiment of the present invention.

In a typical plant oil processing method, oil is extracted in hexane, the crude vegetable oil is degummed, optionally caustic neutralized, bleached using, e.g. clay adsorption with subsequent clay disposal, and deodorized to produce refined, bleached and deodorized or RBD oil (see FIG. 50). The need for the degumming step depends on phosphorus content and other factors. The process of the present invention can be used in conjunction with processes based on extraction with hexane and/or enzyme assisted oil extraction (see Journal of Americal Oil Chemists' Society (2006), 83 (11), 973-979). In general, the process of the invention may be performed using oil processing steps as described in Bailey's Industrial Oil and Fat Products (2005), $6^{th}$ edition, Ed. by Fereidoon Shahidi, John Wiley & Sons.

In embodiments of the present invention, an enzymatic reaction involving application of the enzyme capable of hydrolyzing chlorophyll or a chlorophyll derivative may be performed at various stages in this process, are shown in FIG. 50. In particular embodiments, the enzyme is contacted with the oil before the degumming step. In another embodiment, the enzyme may be contacted with the oil during a water degumming step. In another embodiment, the enzyme is contacted with water degummed oil, but before degumming is complete (e.g. before a total degumming or caustic neutralization step).

Further processing steps, after treatment with the enzyme, may assist in removal of the products of enzymatic hydrolysis of chlorophyll and/or chlorophyll derivatives. For instance, further processing steps may remove chlorophyllide, pheophorbide, pyropheophorbide and/or phytol.

Degumming

The degumming step in oil refining serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, primarily phospholipids such as phosphatidylcholine with a minor component of triglycerides. Thus as used herein, the tem "degumming" means the refining of oil by removing phospholipids from the oil. In some embodiments, degumming may comprise a step of converting phosphatides (such as lecithin and phospholipids) into hydratable phosphatides.

The process of the invention can be used with any degumming procedure, particularly in embodiments where the chlorophyll- or chlorophyll derivative-hydrolyzing enzyme is contacted with the oil before the degumming step. Thus suitable degumming methods include water degumming, ALCON oil degumming (e.g., for soybeans), safinco degumming, "super degumming," UF degumming, TOP degumming, uni-degumming, dry degumming and ENZYMAX™ degumming. See e.g. U.S. Pat. Nos. 6,355,693; 6,162,623; 6,103,505; 6,001,640; 5,558,781; 5,264,367, 5,558,781; 5,288,619; 5,264,367; 6,001,640; 6,376,689; WO 0229022; WO 98118912; and the like. Various degumming procedures incorporated by the methods of the invention are described in Bockisch, M. (1998), Fats and Oils Handbook, The extraction of Vegetable Oils (Chapter 5), 345-445, AOCS Press, Champaign, Ill.

Water degumming typically refers to a step in which the oil is incubated with water (e.g. 1 to 5% by weight) in order to remove phosphatides. Typically water degumming may be performed at elevated temperature, e.g. at 50 to 90° C. The oil/water mixture may be agitated for e.g. 5 to 60 minutes to allow separation of the phosphatides into the water phase, which is then removed from the oil.

Acid degumming may also be performed. For example, oil may be contacted with acid (e.g. 0.1 to 0.5% of a 50% solution of citric or malic acid) at 60 to 70° C., mixed, contacted with 1 to 5% water and cooled to 25 to 45° C.

Further suitable degumming procedures for use with the process of the present invention are described in WO 2006/008508. In one embodiment the process comprises contacting the chlorophyll- or chlorophyll derivative-hydrolyzing enzyme with the oil and subsequently performing an enzymatic degumming step using an acyltransferase as described in WO 2006/008508. Acyltransferases suitable for use in the process are also described in WO 2004/064537, WO 2004/064987 and WO 2009/024736. Any enzyme having acyltransferase activity (generally classified as E.C.2.3.1) may be used, particularly enzymes comprising the amino acid sequence motif GDSX, wherein X is one or more of the following amino acid residues: L, A, V, I, F, Y, H, Q, T, N, M or S. In one embodiment, acyltransferase is a mutant *Aeromonas salmonicida* mature lipid acyltransferase (GCAT) with a mutation of Asn80Asp.

In another embodiment, the process comprises a degumming step using a phospholipase. Any enzyme having e.g. a phospholipase A1 (E.C.3.1.1.32) or a phospholipase A2 (E.C.3.1.1.4) activity may be used, for example Lecitase Ultra® or pancreatic phospholipase A2 (Novozymes, Denmark). In one embodiment the process comprises contacting the chlorophyll- or chlorophyll derivative-hydrolyzing enzyme with the oil before an enzymatic degumming step using a phospholipase, for example using a degumming step as described in U.S. Pat. No. 5,264,367, EP 0622446, WO 00/32758 or Clausen (2001) "Enzymatic oil degumming by a novel microbial phospholipase," Eur. J. Lipid Sci. Technol. 103:333-340.

In another embodiment, the degumming step may be a water degumming step. In a further embodiment, an enzymatic degumming step using an enzyme such as phospholipase C (IUB 3.1.4.1) may be used. Polypeptides having phospholipase C activity which are may be used in a degumming step are disclosed, for example, in WO2008143679, WO2007092314, WO2007055735, WO2006009676 and WO03089620. A suitable phospholipase C for use in the present invention is Purifine®, available from Verenium Corporation, Cambridge, Mass.

Acid Treatment/Caustic Neutralization

In some embodiments, an acid treatment/caustic neutralization step may be performed in order to further reduce phospholipid levels in the oil after water degumming. In another embodiment, a single degumming step comprising acid treatment/caustic neutralization may be performed. Such methods are typically referred to as total degumming or alkali refining.

It has been found that an acid treatment/caustic neutralization step is particularly effective in removing products of the enzymatic hydrolysis of chlorophyll, e.g. chlorophyllide, pheophorbide and pyropheophorbide. Thus this step may be performed at any stage in the process after the enzyme treatment step. For example, such a step may comprise addition of an acid such as phosphoric acid followed by neutralization with an alkali such as sodium hydroxide. Following an acid/caustic neutralization treatment compounds such as chlorophyllide, pheophorbide and pyropheophorbide are extracted from the oil in an aqueous phase.

In such methods, the oil is typically first contacted with 0.05 to 0.5% by weight of concentrated phosphoric acid, e.g. at a temperature of 50 to 90° C., and mixed to help precipitate phosphatides. The contact time may be, e.g. 10 seconds to 30 minutes. Subsequently an aqueous solution of an alkali (e.g. 1 to 20% aqueous sodium hydroxide) is added, e.g. at a temperature of 50 to 90° C., followed by incubation and mixing for 10 seconds to 30 minutes. The oil may then be heated to about 90° C. and the aqueous soap phase separated from the oil by centrifugation.

Optionally, further wash steps with e.g. sodium hydroxide or water may also be performed.

Chlorophyllide, Pheophorbide and Pyropheophorbide Removal

Figure 1:
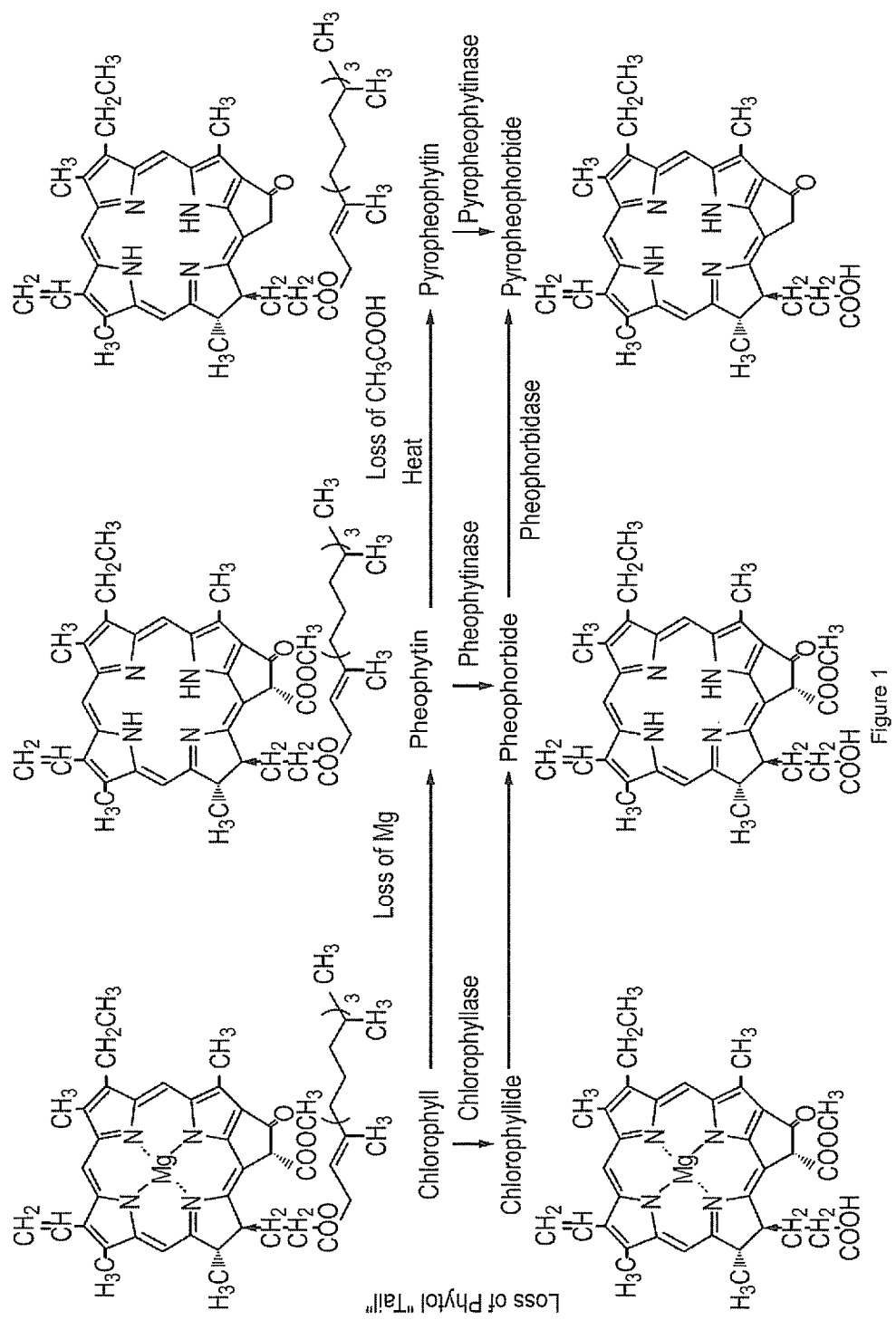
FIG. 1 shows the reactions involving chlorophyll and
derivatives and enzymes used in the present invention.

The method of the present invention may optionally involve a step of removing phytol-free derivatives of chlorophyll such as chlorophyllide, pheophorbide and pyropheophorbide, including prime and non-prime forms thereof. Such products may be present in the composition due to the hydrolysis of chlorophyll or a chlorophyll derivative by the enzyme of the invention, or may be present naturally, as a contaminant, or as an undesired component in a processed product. Pyropheophorbide may also be present in the composition due to the breakdown of pheophorbide, which may itself be produced by the activity of an enzyme having pheophytinase activity on pheophytin, or pheophorbide may be formed from chlorophyllide following the action of chlorophyllase on chlorophyll (see FIG. 1). Processing conditions used in oil refining, in particular heat, may favour the formation of pyropheophorbide as a dominant component, for instance by favouring the conversion of pheophytin to pyropheophytin, which is subsequently hydrolysed to pyropheophorbide.

In one embodiment the process of the present invention reduces the level of chlorophyllide, pheophorbide and/or pyropheophorbide in the oil, compared to either or both of the levels before and after enzyme treatment. Thus in some embodiments the chlorophyllide, pheophorbide and/or pyropheophorbide concentration may increase after enzyme treatment. Typically the process involves a step of removing chlorophyllide, pheophorbide and/or pyropheophorbide such that the concentration of such products is lower than after enzyme treatment. Preferably the chlorophyllide, pheophorbide and/or pyropheophorbide produced by this enzymatic step is removed from the oil, such that the final level of these products in the oil is lower than before enzyme treatment.

For example, the process may reduce the concentration of chlorophyllide, pheophorbide and/or pyropheophorbide, including prime and non-prime forms thereof, by at least 5%, at least 10%, at least 20%, at least 30%, at least 40%, at least 50%, at least 60%, at least 70%, at least 80%, at least 90%, at least 95% or at least 99%, compared to the concentration of chlorophyllide, pheophorbide and/or pyropheophorbide (by weight) present in the oil before the chlorophyllide, pheophorbide and/or pyropheophorbide removal step, i.e. before or after enzyme treatment. Thus in particular embodiments, the chlorophyllide, pheophorbide and/or pyropheophorbide concentration in the oil after the removal step may be less than 100, less than 50, less than 30, less than 10, less than 5, less than 1, less than 0.5, less than 0.1 mg/kg, or less than 0.02 mg/kg, based on the total weight of the composition (e.g a vegetable oil).

It is an advantage of the present process that reaction products such as chlorophyllide, pheophorbide and/or pyropheophorbide may be simply and easily removed from the oil by a step such as acid treatment/caustic neutralization. Thus in preferred embodiments chlorophyll and chlorophyll derivatives may be substantially removed from the oil without the need for further processing steps such as clay and/or silica treatment and deodorization (as indicated by the dashed boxes shown in FIG. 50).

Clay Treatment

It is particularly preferred that the process does not comprise a clay treatment step. Avoiding the use of clay is advantageous for the reasons described earlier, in particular the reduction in cost, the reduced losses of oil through adherence to the clay and the increased retention of useful compounds such as carotenoids and tocopherol.

In some embodiments, the process may be performed with no clay treatment step and no deodorization step, which results in an increased concentration of such useful compounds in the refined oil, compared to a process involving clay treatment.

Silica Treatment

Although not always required, in some embodiments the process may comprise a step of silica treatment, preferably subsequent to the enzyme treatment. For example, the method may comprise use of an adsorbent-free or reduced adsorbent silica refining devices and processes, which are known in the art, e.g., using TriSyl Silica Refining Processes (Grace Davison, Columbia, Md.), or, SORBSIL R™ silicas (INEOS Silicas, Joliet, Ill.).

The silica treatment step may be used to remove any remaining chlorophyllide, pheophorbide and/or pyropheophorbide or other polar components in the oil. For example, in some embodiments a silica treatment step may be used as an alternative to an acid treatment/caustic neutralization (total degumming or alkali refining) step.

In one embodiment the process comprises a two-stage silica treatment, e.g. comprising two silica treatment steps separated by a separation step in which the silica is removed, e.g. a filtration step. The silica treatment may be performed at elevated temperature, e.g. at above about 30° C., more preferably about 50 to 150° C., about 70 to 110° C., about 80 to 100° C. or about 85 to 95° C., most preferably about 90° C.

Deodorization

In some embodiments, the process may comprise a deodorization step, typically as the final refining step in the process. In one embodiment, deodorization refers to steam distillation of the oil, which typically removes volatile odor and flavor compounds, tocopherol, sterols, stanols, carotenoids and other nutrients. Typically the oil is heated to 220 to 260° C. under low pressure (e.g. 0.1 to 1 kPa) to exclude air. Steam (e.g. 1-3% by weight) is blown through the oil to remove volatile compounds, for example for 15 to 120 minutes. The aqueous distillate may be collected.

In another embodiment, deodorization may be performed using an inert gas (e.g. nitrogen) instead of steam. Thus the deodoriztion step may comprise bubble refining or sparging with an inert gas (e.g. nitrogen), for example as described by A. V. Tsiadi et al. in "Nitrogen bubble refining of sunflower oil in shallow pools", Journal of the American Oil Chemists' Society (2001), Volume 78 (4), pages 381-385. The gaseous phase which has passed through the oil may be collected and optionally condensed, and/or volatile compounds extracted therefrom into an aqueous phase.

In some embodiments, the process of the present invention is performed with no clay treatment but comprising a deodorization step. Useful compounds (e.g. carotenoids, sterols, stanols and tocopherol) may be at least partially extracted from the oil in a distillate (e.g. an aqueous or nitrogenous distillate) obtained from the deodorization step. This distillate provides a valuable source of compounds such as carotenoids and tocopherol, which may be at least partially lost by entrainment in a process comprising clay treatment.

The loss of tocopherol during bleaching depends on bleaching conditions and the type of clay applied, but 20-40% removal of tocopherol in the bleaching step has been reported (K. Bold, M, Kubo, T. Wada, and T. Tamura, ibid., 69, 323 (1992)). During processing of soy bean oil a loss of 13% tocopherol in the bleaching step has been reported (S. Ramamurthi, A. R. McCurdy, and R. T. Tyler, in S. S. Koseoglu, K. C. Rhee, and R. F. Wilson, eds., Proc. World Conf. Oilseed Edible Oils Process, vol. 1, AOCS Press, Champaign, Ill., 1998, pp. 130-134).

Carotenoids may be removed from the oil during deodorization in both clay-treated and non-clay-treated oil. Typically the removal of coloured carotenoids is controlled in order to produce an oil having a predetermined colour within a specified range of values. The level of carotenoids and other volatile compounds in the refined oil can be varied by modifying the deodorization step. For instance, in an embodiment where it is desired to retain a higher concentration of carotenoids in the oil, the deodorization step may be performed at a lower temperature (e.g. using steam at 200° C. or below). In such embodiments it is particularly preferable to avoid a clay treatment step, since this will result in a higher concentration of carotenoids in the refined oil.

Further Enzyme Treatments

In further aspects, the processes of the invention further comprise use of lipid acyltransferases, phospholipases, proteases, phosphatases, phytases, xylanases, amylases (e.g. α-amylases), glucanases, polygalacturonases, galactolipases, cellulases, hemicellulases, pectinases and other plant cell wall degrading enzymes, as well as mixed enzyme preparations and cell lysates. In alternative aspects, the processes of the invention can be practiced in conjunction with other processes, e.g., enzymatic treatments, e.g., with carbohydrases, including cellulase, hemicellulase and other side degrading activities, or, chemical processes, e.g., hexane extraction of soybean oil. In one embodiment the method of the present invention can be practiced in combination with a method as defined in WO 2006031699.

The invention will now be further illustrated with reference to the following non-limiting examples.

EXAMPLE 1

Identification and Cloning of Chlorophyllases

Using different approaches (including BLAST) to search the NCBI databases, several sequences were identified as chlorophyllases or sequences having homology to chlorophyllases. The names of the sequences, their origin and NCBI database accession numbers are listed in Table 1.

TABLE 1

Chlorophyllases with accession numbers and names used herein.

| Organism | Database acc. no. | CHL name |
|---|---|---|
| Arabidopsis thaliana | AAG12547 | ARA_CHL |
| Arabidopsis thaliana | NP_199199 | ARA_CHL2 |
| Citrus sinensis | AAF59834 | CIT_CHL |
| Triticum aestivum | BT009214 | TRI_CHL |
| Triticum aestivum | BT008923 | TRI_CHL2 |
| Brassica oleracea | AAN51935 | BRA_CHL |
| Brassica oleracea | AAN51933 | BRA_CHL1 |
| Brassica oleracea | AAN51934 | Brass_CHL2 |
| Zea Mays | ACN32030 | ZEA_CHL |
| Zea Mays | ACG44273 | ZEA_CHL2 |
| Phyllostachys edulis | FP092915 | BAM_CHL |

TABLE 1-continued

Chlorophyllases with accession numbers and names used herein.

| Organism | Database acc. no. | CHL name |
|---|---|---|
| Chenopodium album | Q9LE89 | CHE_CHL |
| Ricinus communis | XP_002517075 | CB_CHL |
| Glycine max | BAF43704 | GlyMax_CHL |
| Ginkgo biloba | AAP44978 | Gin_CHL |
| Pachira macrocarpa | ACO50429 | PAC_CHL2 |
| Populus trichocarpa | XP_002315752 | POP_CHL |
| Sorghum bicolor | XP_002459848 | Sor_CHL |
| Sorghum bicolor | XP_002445588 | SORG_CHL |
| Vitis vinifera | XP_002273926 | Vitis_CHL |
| Physcomitrella patens | EDQ81786 | PHYS_CHL |
| Aquilegia | | AQU_CHL |
| Brachypodium distachyon | ADDN01001446 | BRACH_CHL |
| Medicago truncatula | ACJ85964 | MED_CHL |
| Piper betle | ABI96085 | PIP_CHL |
| Lotus japonicus | AK338339 | LOTUS_CHL |
| Oryza sativa Indica | EEC66959 | ORYI_CHL |
| Oryza sativa Japonica | NP_001064620 | ORYJ1_CHL |
| Oryza sativa Japonica | EEE50970 | ORYJ2_CHL |
| Picea sitchensis | ACN40275 | PICEA_CHL |
| Chlamydomonas | XP_001695577 | CHL_CHL |

Chlorophyllase Sequences

Figure 43:
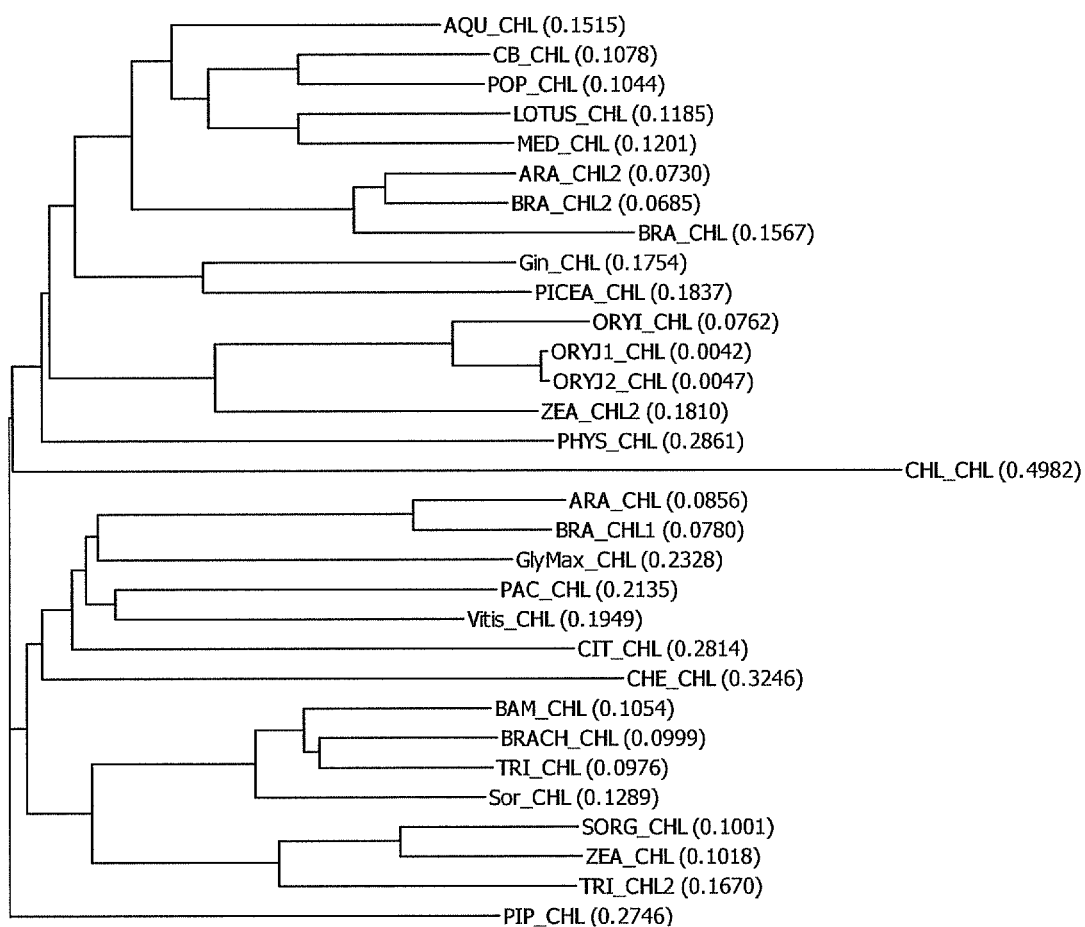
FIG. 43 shows a phylogenetic tree of the plant chlorophyllases and the *Chlamydomonas* chlorophyllase (CHL_CHL) described herein.

The chlorophyllase sequences identified from the search in NCBI databases are listed in Table 1 and the amino acid sequences are shown in FIGS. 12 to 42 (SEQ ID NO:s 1 to 31). Multiple sequence alignment of the selected chlorophyllase amino acid sequences showed several conserved residues distributed throughout the sequences. The motif GHSRG (SEQ ID NO: 32) containing the Ser active site is highly conserved. The alignment resulted in a phylogenetic tree as shown in FIG. 43.

Cloning in E. Coli

Synthetic genes encoding the chlorophyllases shown in Table 1 were prepared. Each gene was codon optimized for expression in E. coli. For cloning purposes the genes were extended in the 5'-end to contain a restriction site for NheI and in the 3'-end to contain a restriction site for XhoI.

Figure 4:
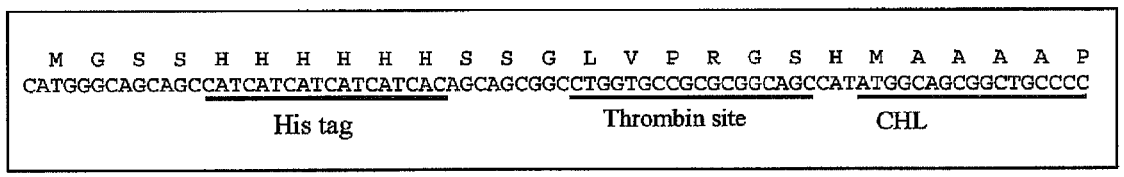
FIG. 4 shows amino acid and nucleotide sequences showing the fusion of a chlorophyllase gene to a His tag and
thrombin site. The nucleotide sequence is provided as SEQ
ID NO: 34 encoding the polypeptide provided as SEQ ID
NO: 35.
Figure 5:
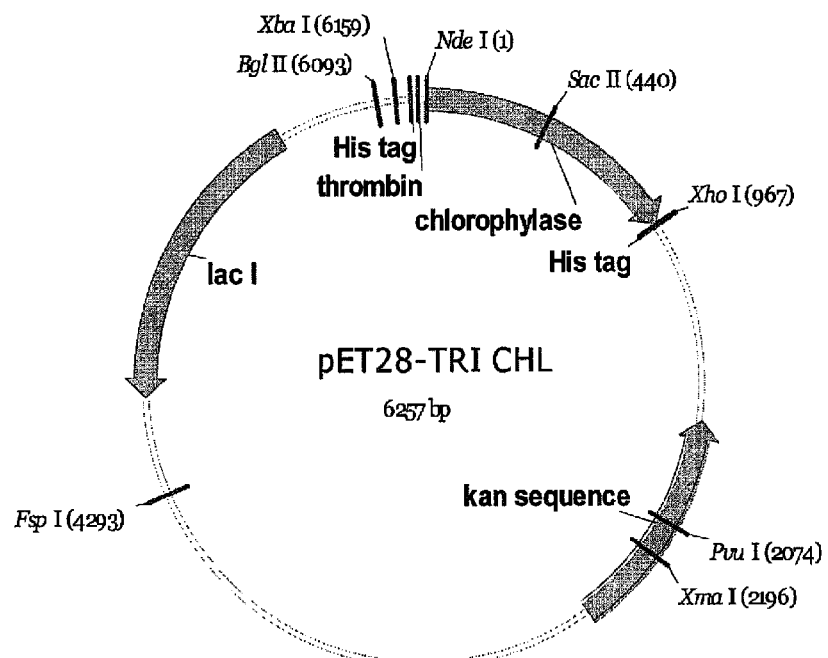
FIG. 5 shows a schematic presentation of an *E. coli*.
expression vector pET28-TRI_CHL containing the
TRI_CHL gene encoding a chlorophyllase from *Triticum
aestivum* (database acc. no. BT009214).

Following digestion with NheI and XhoI restriction enzymes the synthetic DNA was ligated into the E. coli expression vector pET-28a(+) (Novagen) digested with the same restriction enzymes. This vector includes a T7 promoter with a Lac operator for controlling expression of inserted genes. The chlorophyllase genes were fused in frame to a His tag and a thrombin cleavage site for purification (example shown in FIG. 4). The resulting constructs (an example pET28-TRI_CHL is shown in FIG. 5), were transformed into competent E. coli TOP10 cells (Invitrogen), and plasmids were isolated from transformed colonies and subjected to nucleotide sequencing to verify the correct sequence and that all fusions were as expected.

Expression in E. Coli

For expression the plasmids were transformed into the expression host E. coli BL21(DE3) (Novagen). The cells were cultured at 37° C. in LB containing carbenicillin (50 mg/ml) until $OD_{600}$ 0.6-0.8. For induction the culture was added 1 mM IPTG and incubated at 25° C. for another 20-24 h before harvesting the cells by centrifugation. The recombinant chlorophyllases were released from the cell pellet by sonication and cellular debris removed by centrifugation.

Cloning in B. Subtilis

For cloning and expression in B. subtilis the synthetic genes encoding the chlorophyllases (Table 1) were codon optimized for B. subtilis. The genes were cloned in two different plasmids, one for intracellular expression and one for secretion into the culture medium (extracellular expression).

Extracellular Expression

Figure 6:
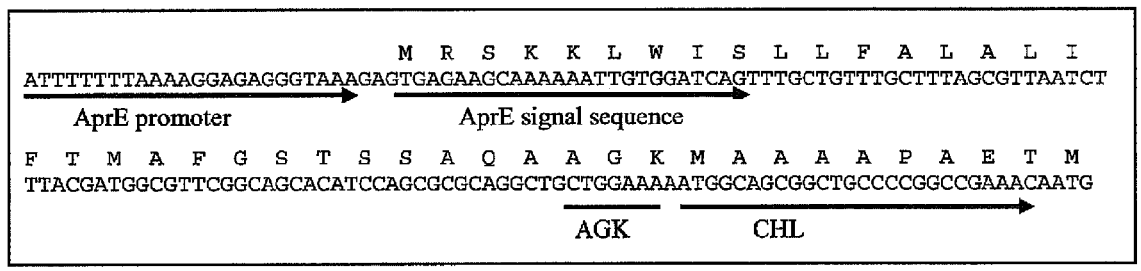
FIG. 6 shows amino acid and nucleotide sequences showing the fusion of a chlorophyllase gene to an AprE signal sequence and an AGK sequence. The nucleotide sequence is provided as SEQ ID NO: 36 encoding the polypeptide provided as SEQ ID NO: 37.
Figure 7:
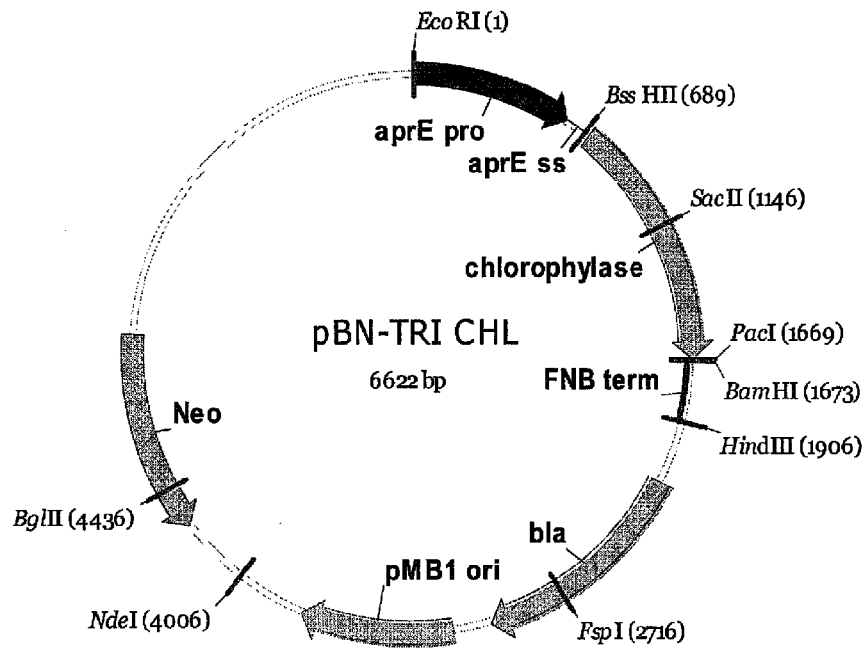
FIG. 7 shows a schematic presentation of a *B. subtilis* expression vector pBN-TRI_CHL containing the TRI_CHL gene encoding a chlorophyllase from *Triticum aestivum* (database acc. no. BT009214).

The genes were extended in the 5'-end to contain a restriction site for BssHII and part of an AprE signal sequence for in frame fusion to the AprE signal sequence as well as a sequence encoding the amino acids A G K to facilitate signal sequence cleavage. In the 3' end the genes were extended with a restriction site for PacI. The BssHII and PacI digested genes were ligated into B. subtilis expression vector pBN digested with the same restriction enzymes. The pBN vector contains an AprE promoter and an AprE signal sequence. An example of the resulting fusion of the chlorophyllase genes with the AprE signal sequence is shown in FIG. 6. The final constructs (an example pBN-TRI_CHL is shown in FIG. 7), were transformed into competent E. coli TOP10 cells (Invitrogen), and plasmids were isolated from transformed colonies and subjected to nucleotide sequencing to verify the correct sequence and that all fusions were as expected.

For expression the plasmids were transformed into the expression host B. subtilis BG6002. The cells were cultured at 33° C. in Grant's II medium for 68 h. The recombinant chlorophyllases were isolated from the culture medium after precipitation of the cells by centrifugation.

Intracellular Expression

Figure 8:
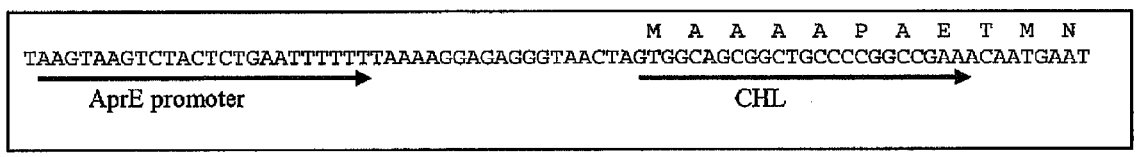
FIG. 8 shows amino acid and nucleotide sequences showing the fusion of a chlorophyllase gene directly to an AprE promoter. The nucleotide sequence is provided as SEQ ID NO: 38 encoding the polypeptide provided as SEQ ID NO: 39.
Figure 9:
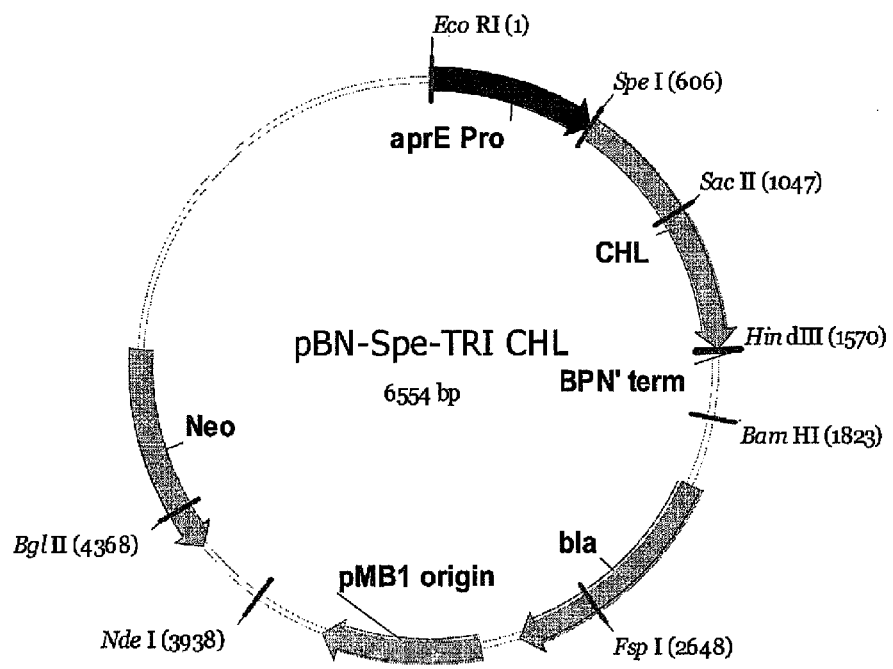
FIG. 9 shows a schematic presentation of a *B. subtilis* expression vector pBN-Spe-TRI_CHL containing the TRI_CHL gene encoding a chlorophyllase from *Triticum aestivum* (database acc. no. BT009214).

The genes were extended in the 5'-end to contain a restriction site for SpeI to allow fusion of the genes directly to the AprE promoter in a B. subtilis expression vector pBN without the AprE signal sequence. In the 3' end the genes were extended with a restriction site for HindIII. The fusion of a chlorophyllase gene to the AprE promoter is shown in FIG. 8. The resulting constructs (an example pBN-Spe-TRI_CHL is shown in FIG. 9), were transformed into competent E. coli TOP 10 cells (Invitrogen), and plasmids were isolated from transformed colonies and subjected to nucleotide sequencing to verify the correct sequence and that all fusions were as expected.

For expression the plasmids were transformed into the expression host B. subtilis BG6002. The cells were cultured at 33° C. in Grant's II medium for 68 h. The recombinant chlorophyllases were released from the cultures by treatment with 1 mg/ml Lysozyme for 1 h at 30° C. Cellular debris was removed by centrifugation and the chlorophyllases were recovered from the supernatant.

Cloning in S. Lividans

Figure 10:
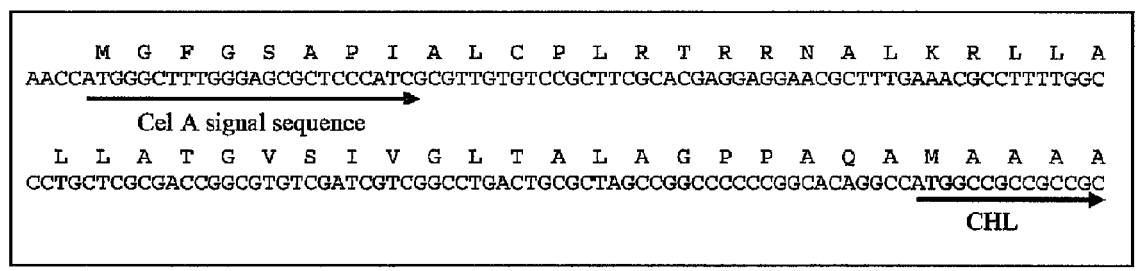
FIG. 10 shows amino acid and nucleotide sequence showing the fusion of a chlorophyllase gene to the Cel A signal sequence. The nucleotide sequence is provided as SEQ ID NO: 40 encoding the polypeptide provided as SEQ ID NO: 41.
Figure 11:
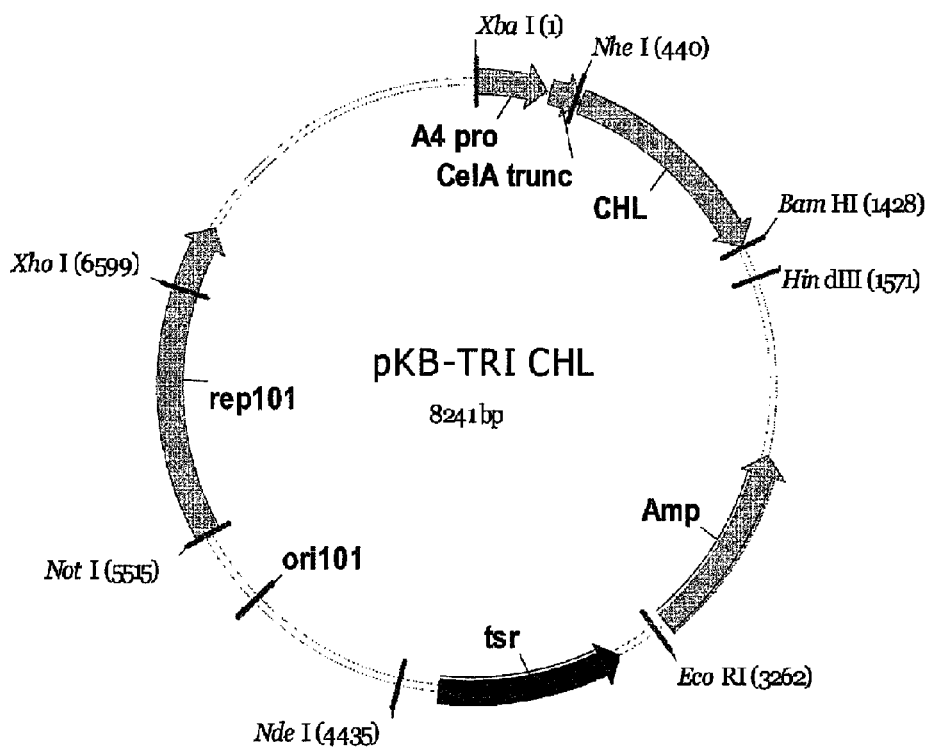
FIG. 11 shows a schematic presentation of an *S. lividans* expression vector pKB-TRI_CHL containing the TRI_CHL gene encoding a chlorophyllase from *Triticum aestivum* (database acc. no. BT009214).

For cloning and expression in S. lividans the synthetic genes encoding the chlorophyllases (Table 1) were codon optimized for S. lividans. For cloning purposes the genes were extended in the 5'-end to contain a restriction site for NheI and part of a Cel A signal sequence for in frame fusion to the Cel A signal sequence. The 3'-end was extended to contain a restriction site for BamHI. The fusion of a chlorophyllase gene (TRI_CHL) to the Cel A signal sequence is shown in FIG. 10. The resulting constructs (an example pKB-TRI_CHL is shown in FIG. 11), were transformed into competent E. coli TOP10 cells (Invitrogen), and plasmids were isolated from transformed colonies and subjected to nucleotide sequencing to verify the correct sequence and that all fusions were as expected.

Expression in S. Lividans

For expression plasmids were transformed into protoplasts of the expression host S. lividans strain g3s3. The cells were pre-cultured for 48 h at 30° C. in TSG medium supplemented with thiostrepton. The pre-cultures were diluted 10× in Strept Pdxn2 modified medium and incubated at 30° C. for 96 h. The recombinant chlorophyllases were isolated from the culture medium after precipitation of the cells by centrifugation.

EXAMPLE 2

Activity of Chlorophyllases

A number of chlorophyllases were identified by genome mining as described above and expressed in E. coli. The extracts from E. coli harboring plasmids containing the chlorophyllase gene were analyzed for pheophytinase activity. The assay may be performed as described in EP10159327.5. Alternatively pheophytinase activity may be determined by a method as described above, e.g. HPLC-based methods. The results are shown in Table 2.

Pheophytinase activity may be determined based on hydrolysis of pheophytin a in a reaction buffer followed by fluorescent measurement of the generated pheophorbide a. The assay can also be adapted to employ pyropheophytin as a substrate. 1 U of enzyme activity is defined as hydrolysis of 1 μmole of pheophytin a or pyropheophytin per minute at 40° C.

TABLE 2

Pheophytinase activity of enzymes

| Enzyme | Ferment | Activity U/ml |
| --- | --- | --- |
| BAM_CHL | CoRe 112 | 0.32 |
| CIT_CHL | CoRe 113-A | 0.25 |
| ARA_CHL | CoRe 114-A | 5.19 |
| CB_CHL | CoRe 127 | 0.10 |
| GlyMax_CHL | Core133 | 0.010 |
| Sor_CHL | Core134 | 6.14 |
| ARA_CHL2 | Core135 | 0.94 |
| BRA_CHL1 | Core136 | 1.21 |
| SORG_CHL | CoRe 137-A | 0.78 |
| TRI_CHL2 | Core138-A | 0.19 |
| ZEA_CHL2 | Core139 | 0.03 |
| TRI_CHL | CoRe 20 | 0.18 |
| BRACH_CHL | CoRe 156 | 1.50 |
| PIP_CHL | CoRe 158 | 0.01 |
| PICEA_CHL | CoRe 163 | 0.05 |
| Control | Empty vector | 0.000 |

Figure 44:
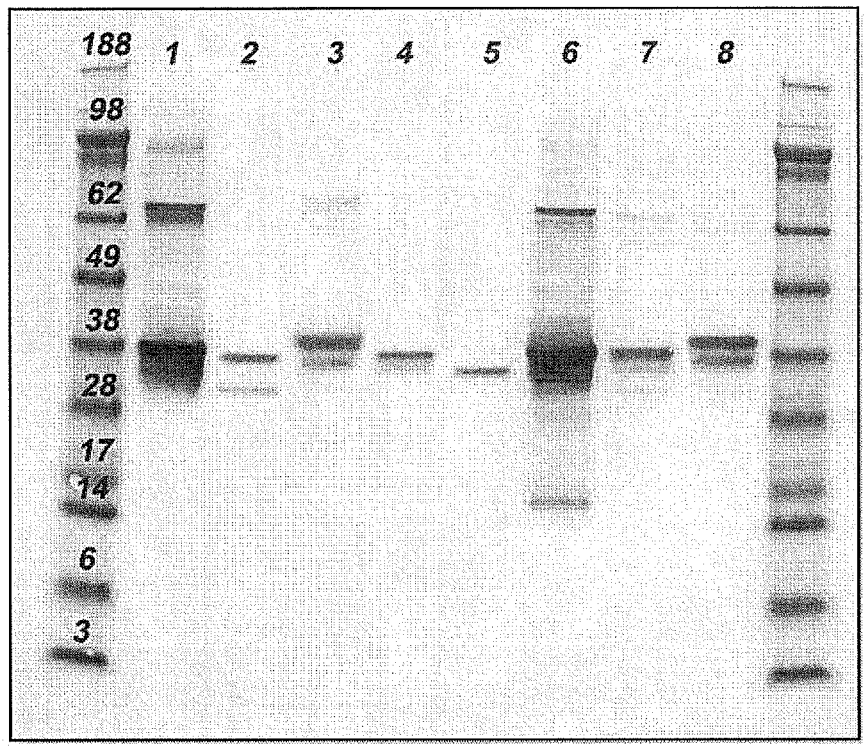
FIG. 44 shows a Western blot analysis of *E. coli* extracts containing recombinant chlorophyllases derived from various species. Lane 1: BAM_CHL CoRe 112. Lane 2: CIT_CHL CoRe 113A. Lane 3: ARA_CHL CoRe 114A. Lane 4: CB_CHL CoRe 127. Lane 5: GlyMax_CHL CoRe 133. Lane 6: Sor_CFIL CoRe 134. Lane 7: ARA_CHL2 CoRe 135. Lane 8: BRA_CHL1 CoRe 136. See Tables 1 and 2 below for definitions of source species of the enzymes corresponding to the above abbreviations.
Figure 45:
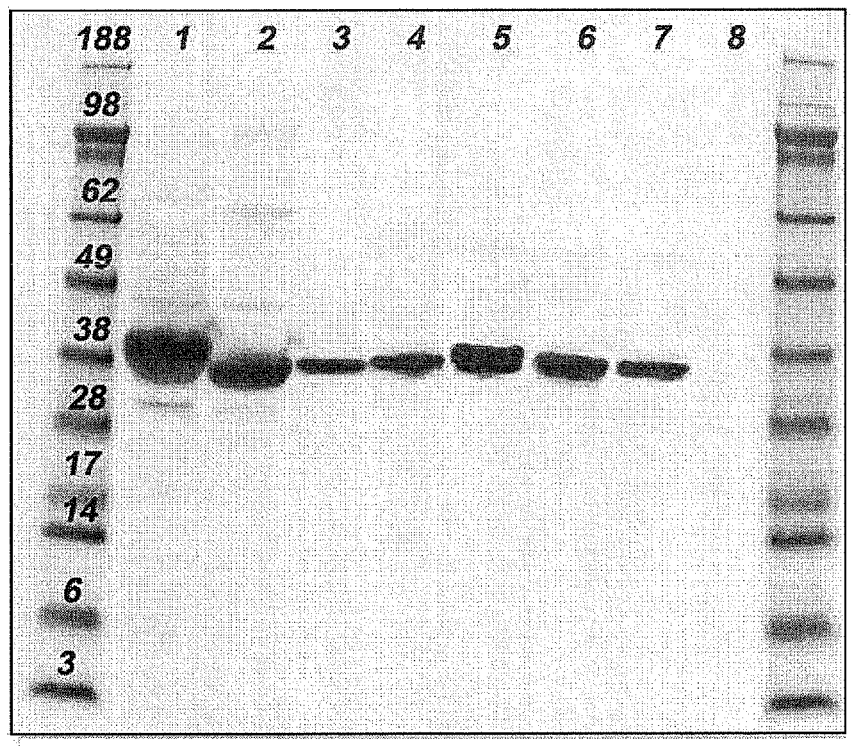
FIG. 45 shows a Western blot analysis of *E. coli* extracts containing recombinant chlorophyllases derived from various species. Lane 1: SORG_CHL CoRe 137A. Lane 2: TRI_CHL2 CoRe 138A. Lane 3: ZEA_CRL2 CoRe 139. Lane 4: TRI_CHL CoRe 20. Lane 5: BRACH_CHL CoRe 156. Lane 6: PIP_CHL CoRe 158. Lane 7: PICEA_CHL CoRe 163. Lane 8: Vector control. See Tables 1 and 2 below for definitions of source species of the enzymes corresponding to the above abbreviations.

The enzymes described in Table 2 were analyzed by western blot analysis using a primary antibody raised in rabbit against purified TRI_CHI. FIGS. 44 and 45 show that all enzymes from Table 2 react with the raised antibody.

EXAMPLE 3

Hydrolysis of Chlorophyll Derivatives in Plant Oils

Some of the enzymes were tested for the ability to degrade chlorophyll components in an oil system. The recipe is shown in Table 3. Crude rapeseed oil is scaled in a Wheaton glass and heated with magnetic stirring to 60° C. Water and enzyme are added. The sample is treated with high shear mixing for 20 seconds and incubated at 60° C. with magnetic stirring. Samples are taken out after 0.5, 2 and 4 hours reaction time. The samples are centrifuged and analysed by HPLC-MS.

TABLE 3

Recipe for testing chlorophyllases in oil system

| | Units/ml | | 1 | 2 | 3 | 4 | 5 | 6 |
| --- | --- | --- | --- | --- | --- | --- | --- | --- |
| Crude rape seed AKK extracted no 11 | | | 10 | 10 | 10 | 10 | 10 | 10 |
| water | | ml | 0.200 | 0.152 | 0.159 | 0.011 | 0.191 | 0.162 |
| ARA_CHL2 | 0.62 | ml | | 0.0484 | | | | |
| BRA_CHL1 | 3.62 | ml | | | 0.0414 | | | |
| CB_CHL | 2.11 | ml | | | | 0.189 | | |
| TRI_CHL | 54.19 | ml | | | | | 0.009 | |
| SORG_CHL | 0.78 | ml | | | | | | 0.0385 |
| Units/g oil | | | 0.000 | 0.0030 | 0.0150 | 0.0400 | 0.0500 | 0.003 |
| % Water | | | 2.000 | 2.000 | 2.000 | 2.000 | 2.000 | 2.000 |
| Temperature | | ° C. | 60 | 60 | 60 | 60 | 60 | 60 |

Figure 46:
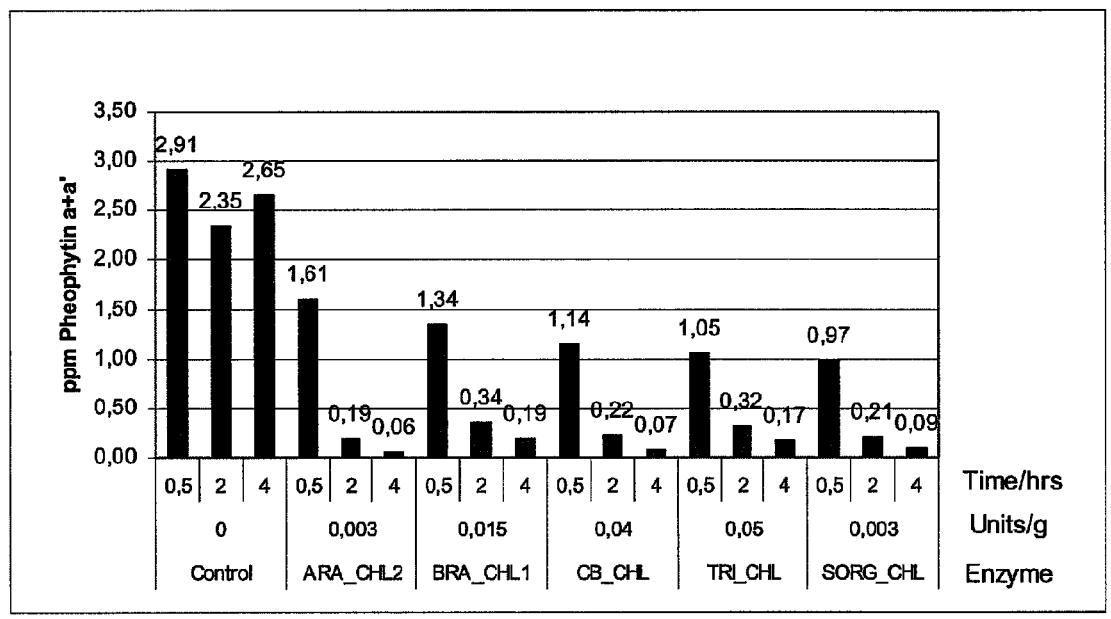
FIG. 46 shows activity of recombinant enzymes derived from various species on pheophytin a, as demonstrated by total pheophytin a (pheophytin a+a') levels in ppm remaining at various times after treatment with each enzyme.
Figure 47:
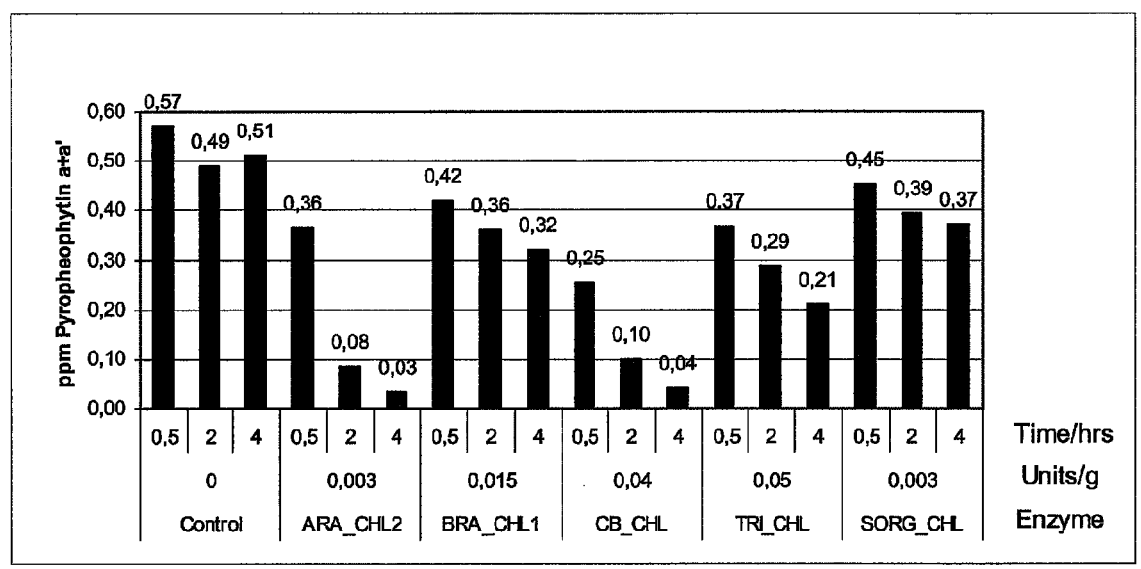
FIG. 47 shows activity of recombinant enzymes derived from various species on pheophytin a, as demonstrated by pyropheophytin a levels in ppm remaining at various times after treatment with each enzyme.

The total levels of pheophytin a (pheophytin a+a') as determined by HPLC-MS are shown in FIG. 46. The degradation of pyropheophytin a is shown in FIG. 47. All 5 enzyme candidates can degrade pheophytin and pheophytin but especially the activity on pyropheophytin varies significantly among the 5 tested enzymes.

In the oil samples treated with chlorophyllase we also analyzed the distribution of pheophytin stereoisomers a and a'. Surprisingly we found large differences in the distribution depending on the enzyme applied (see FIG. 48). For the BRA_CHL1 and TRI_CHL, the percentage of pheophytin a drops to around half of the initial level whereas ARA_CHL2 and CB_CHL show a distribution which is comparable to the control and initial level. Retaining the initial distribution of stereoisomers throughout the reaction is a clear advantage as this means that the overall reaction rate is not dependent on the epimerization of pheophytin a' to a. These findings also indicate that ARA_CHL2 and CB_CHL are not very sensitive to the groups at C-$13^2$. These two enzymes also show much better activity on pyropheophytin, which has 2 hydrogen atoms at C-$13^2$ (see FIG. 47).

Substrate Specificity in an In Vitro Assay

The relative activities of the above enzymes on pheophytin and pyropheophytin in an in vitro assay system, e.g. as described in EP10159327.5, were measured. Table 4 gives the ratio of pheophytin to pyropheophytin activity.

TABLE 4

Ratio of pheophytin to pyropheophytin activity

| Enzyme | Ratio of activity on pheophytin to pyropheophytin |
| --- | --- |
| SORG_CHL | 173 |
| ARA_CHL2 | 4 |

TABLE 4-continued

Ratio of pheophytin to pyropheophytin activity

| Enzyme | Ratio of activity on pheophytin to pyropheophytin |
|---|---|
| CB_CHL | 4 |
| TRI_CHL | 45 |

It is clear that SORG_CHL has a relatively lower activity on pyropheophytin compared to TRI_CHL. The CB_CHL and ARA2_CHL show a different substrate specificity which is much improved towards pyropheophytin. These findings correlate with what is shown in FIGS. 46 to 48.

EXAMPLE 4

Relative Activity of Chlorophyllases on Pheophytin a and a'

Dosage response of chlorophyllases in crude rapeseed oil was tested according to the recipe in Table 5

TABLE 5

|  | Units/g |  | 1 | 2 | 3 | 4 | 5 | 6 | 7 |
|---|---|---|---|---|---|---|---|---|---|
| Crude rape seed no 11, AAK |  |  | 10 | 10 | 10 | 10 | 10 | 10 | 10 |
| water |  | ml | 0.200 | 0.176 | 0.153 | 0.106 | 0.011 | 0.184 | 0.173 |
| CB_CHL, CoRe 127-A. 2.12 U/ml | 2.12 | ml |  | 0.0236 | 0.0472 | 0.0943 | 0.1887 |  |  |
| ARA_CHL CoRe 135 | 0.94 | ml |  |  |  |  |  | 0.0160 | 0.0266 |
| CoRe 137-A SORG_CHL | 0.78 |  |  |  |  |  |  |  |  |
| Units/g oil |  |  | 0.000 | 0.005 | 0.010 | 0.020 | 0.040 | 0.0015 | 0.003 |
| Water |  | % | 2.000 | 2.000 | 2.000 | 2.000 | 2.000 | 2.000 | 2.000 |
| Temperature |  | ° C. | 60 | 60 | 60 | 60 | 60 | 60 | 60 |
| pH |  |  | 4.85 | 5.52 | 5.29 | 5.56 | 5.55 | 5.40 | 5.36 |
|  | Units/g |  | 8 | 9 | 10 | 11 | 12 | 13 | 14 |
| Crude rape seed no 11, AAK |  |  | 10 | 10 | 10 | 10 | 10 | 10 | 10 |
| water |  | ml | 0.147 | 0.047 | 0.006 | 0.091 | 0.187 | 0.162 | 0.072 |
| CB_CHL, CoRe 127-A. 2.12 U/ml | 2.12 | ml |  |  | 0.0943 |  |  |  |  |
| ARA_CHL CoRe 135 | 0.94 | ml | 0.0532 | 0.0532 |  |  | 0.0128 | 0.0385 | 0.1282 |
| CoRe 137-A SORG_CHL | 0.78 |  |  |  |  |  |  |  |  |
| Units/g oil |  |  | 0.005 | 0.005 | 0.020 | 0.050 | 0.001 | 0.003 | 0.010 |
| Water |  | % | 2.000 | 1.000 | 1.000 | 1.000 | 2.000 | 2.000 | 2.000 |
| Temperature |  | ° C. | 60 | 60 | 60 | 60 | 60 | 60 | 60 |
| pH |  |  | 5.28 | 4.99 | 5.06 | 4.82 | 5.01 | 5.49 | 5.55 |

Samples were taken out after ½, 2 and 4 hours reaction time and analysed by HPLC-MS. In order to compare the activity of different chlorophyllases on the two isomers, the enzyme activity on both isomers was calculated at a substrate concentration which is half of the original concentration. The natural logarithm of the substrate concentration is plotted as a function of enzyme dosage (Units/g), as shown in FIG. 51 for *Arabidopsis* chlorophyllase (ARA_CHL2).

Figure 51:
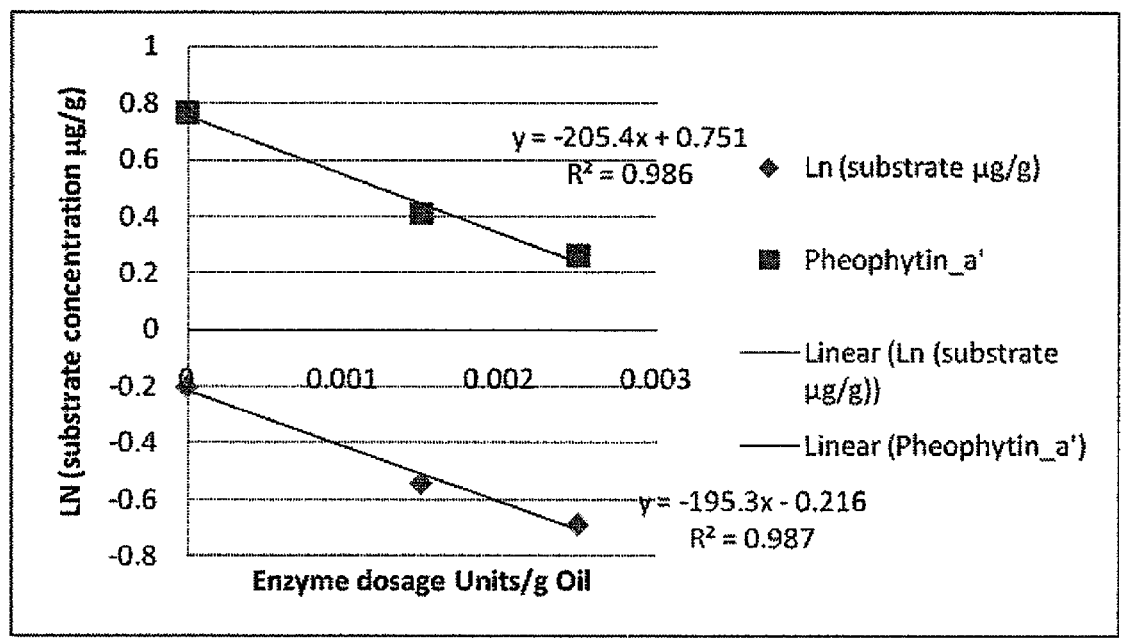
FIG. 51 shows the logarithm of substrate concentration for pheophytin a and a' after ½ hr as a function of ARA_CRL2 (*Arabidopsis chlorophyllase*) dosage.

Based on the graph in FIG. 51, the activity of the enzyme on pheophytin a and a' is calculated for the substrate concentration which is half the original concentration, as shown in Table 6.

TABLE 6

Calculation of ARA-CHL2 activity on pheophytin a and pheophytin a'

|  | Pheophytin a' Units/g oil | Pheophytin_a' Ln (substrate µg/g) |  | Pheophytin_a Units/g oil | Pheophytin_a Ln (substrate µg/g) |
|---|---|---|---|---|---|
|  | 0 | −0.203 |  | 0 | 0.766 |
|  | 0.0015 | −0.541 |  | 0.0015 | 0.409 |
|  | 0.0025 | −0.685 |  | 0.0025 | 0.259 |
| Conc ½ |  | −0.896 | Conc ½ |  | 0.073 |
| Slope |  | −195.3 | Slope |  | −205.5 |
| Intercept |  | −0.216 | Intercept |  | 0.752 |
| Units for conc½ |  | 0.003 | Units for conc½ |  | 0.003 |
| Reciproc µg/u |  | 287.1 | Reciproc µg/u |  | 302.5 |
| Reciproc µg/u/hr |  | 574.2 | Reciproc µg/u/hr |  | 605.0 |

Based on the enzyme activity at half the original substrate concentration, it is possible to compare different enzymes under the same conditions. In Table 7 the results from two different chlorophyllases are compared.

TABLE 7

Chlorophyllase activity on pheophytin a and a' isomers in crude rape seed oil

| Enzyme | Pheophytin_a' µg/Unit/hr | Pheophytin_a µg/Unit/hr | Relative activity a'/a |
|---|---|---|---|
| ARA_CHL2, CoRe135 | 574 | 605 | 0.95 |
| CB_CHL, CoRe 127-A | 141 | 343 | 0.41 |

The results in Table 7 indicate that ARA_CHL2 has almost the same activity on pheophytin a and a' isomers. This is in agreement with the observations that the ratio between the two isomers does not change during enzymatic degradation with ARA_CRL2 (see FIG. 48). In contrast CB_CHL also shows significant hydrolytic activity on pheophytin a'. Expressed in terms of an activity ratios on pheophytin a compared to pheophytin a' (i.e. the inverse of that shown in Table 7), ARA_CRL2 has an activity ratio of 1.05 and CB_CHL has an activity ratio of 2.44.

CONCLUSION

We have identified 31 chlorophyllase sequences and furthermore cloned and expressed these in E. coli, B. subtilis or S. lividans. Based on expression in E. coli we have detected pheophytinase activity (Table 2) in nearly half of the identified chlorophyllases and all of these reacted with antibody raised against TRI_CHL (FIGS. 44 and 45). In the protein extracts without detectable pheophytinase activity we could not detect any expressed chlorophyllase enzyme based on western blots with antibody raised against TRI_CHL.

When testing the chlorophyllase candidates in oil applications we found major differences in specificity for the pheophytin and pyropheophytin substrates. The ARA_CHL2 and CB_CHL show much better activity on pyropheophytin compared to the other candidates tested (FIG. 47). For these two candidates we also observed that the ratio of pheophytin a to a' did not change significantly during incubation in oil trials. For the other candidates tested we saw a clear decrease in this ratio during incubation. The improved activity towards pyropheophytin for ARA_CHL2 and CB_CHL in oil assay was also measured in the in vitro assay using pheophytin and pyropheophytin as substrates (Table 4).

HPLC Analysis

In the examples herein, chlorophyll derivatives may in general be quantified by HPLC analysis according to the following method. HPLC analysis is performed using a method in general terms as described in "Determination of chlorophylls and carotenoids by high-performance liquid chromatography during olive lactic fermentation", Journal of Chromatography, 585, 1991, 259-266.

The determination of pheophytin, pheophorbide, pyropheophytin and pyropheophorbide is performed by HPLC coupled to a diode array detector. The column employed in the method is packed with C18 material and the chlorophylls were separated by gradient elution. Peaks are assigned using standards of chlorophyll A and B from SigmaAldrich, e.g. based on the representative HPLC chromatogram from Journal of Chromatography, 585, 1991, 259-266 shown in FIG. 49.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A process for treating a plant oil comprising a step of contacting the oil with an enzyme, wherein the enzyme is capable of hydrolysing an a' or b' stereoisomer of chlorophyll or a chlorophyll derivative and wherein the enzyme comprises a polypeptide having at least 90% sequence identity with the polypeptide of SEQ ID NO: 13.

2. The process according to claim 1, wherein the a' or b' stereoisomer is chlorophyll a', pheophytin a', chlorophyll b' or pheophytin b'.

3. The process according to claim 1, wherein the enzyme is capable of hydrolysing an a' stereoisomer of chlorophyll or the chlorophyll derivative.

4. The process according to claim 1, wherein the enzyme has an activity ratio of less than 10, where said activity ratio is (a) the ratio of the activity of the enzyme on the a stereoisomer of chlorophyll or the chlorophyll derivative to the activity of the enzyme on the a' stereoisomer of chlorophyll or chlorophyll derivative, or (b) the ratio of the activity of the enzyme on the b stereoisomer of chlorophyll or chlorophyll derivative to the activity of the enzyme on the b' stereoisomer of chlorophyll or the chlorophyll derivative.

5. The process according to claim 1, wherein following treatment with the enzyme the oil comprises (a) at least 50% a stereoisomers of chlorophyll or the chlorophyll derivative, based on the total amount of a and a' stereoisomers of chlorophyll or the chlorophyll derivative in the oil; or (b) at least 50% b stereoisomers of chlorophyll or the chlorophyll derivative, based on the total amount of b and b' stereoisomers of chlorophyll or the chlorophyll derivative in the oil.

6. The process according to claim 1, wherein the enzyme has an activity ratio of less than 10, wherein said activity ratio is the ratio of the activity of the enzyme on pheophytin to the activity of the enzyme on pyropheophytin.

7. The process according to claim 1, wherein the enzyme comprises a chlorophyllase, pheophytinase and/or pyropheophytinase activity.

8. The process according to claim 1, wherein the enzyme comprises the amino acid sequence GHSRG (SEQ ID NO: 32).

9. The process according to claim 1, wherein the enzyme is derived from *Ricinus communis*.

* * * * *

SEQUENCE LISTING

```
<160> NUMBER OF SEQ ID NOS: 41

<210> SEQ ID NO 1
<211> LENGTH: 324
<212> TYPE: PRT
<213> ORGANISM: Arabidopsis thaliana

<400> SEQUENCE: 1

Met Ala Ala Ile Glu Asp Ser Pro Thr Phe Ser Ser Val Val Thr Pro
1               5                   10                  15

Ala Ala Phe Glu Ile Gly Ser Leu Pro Thr Thr Glu Ile Pro Val Asp
                20                  25                  30

Pro Val Glu Asn Asp Ser Thr Ala Pro Pro Lys Pro Val Arg Ile Thr
            35                  40                  45

Cys Pro Thr Val Ala Gly Thr Tyr Pro Val Val Leu Phe Phe His Gly
        50                  55                  60

Phe Tyr Leu Arg Asn Tyr Phe Tyr Ser Asp Val Leu Asn His Ile Ala
65                  70                  75                  80

Ser His Gly Tyr Ile Leu Val Ala Pro Gln Leu Cys Lys Leu Leu Pro
                85                  90                  95
```

```
Pro Gly Gly Gln Val Glu Val Asp Asp Ala Gly Ser Val Ile Asn Trp
            100                 105                 110

Ala Ser Glu Asn Leu Lys Ala His Leu Pro Thr Ser Val Asn Ala Asn
        115                 120                 125

Gly Lys Tyr Thr Ser Leu Val Gly His Ser Arg Gly Gly Lys Thr Ala
    130                 135                 140

Phe Ala Val Ala Leu Gly His Ala Ala Thr Leu Asp Pro Ser Ile Thr
145                 150                 155                 160

Phe Ser Ala Leu Ile Gly Ile Asp Pro Val Ala Gly Thr Asn Lys Tyr
                165                 170                 175

Ile Arg Thr Asp Pro His Ile Leu Thr Tyr Lys Pro Glu Ser Phe Glu
            180                 185                 190

Leu Asp Ile Pro Val Ala Val Val Gly Thr Gly Leu Gly Pro Lys Trp
        195                 200                 205

Asn Asn Val Met Pro Pro Cys Ala Pro Thr Asp Leu Asn His Glu Glu
    210                 215                 220

Phe Tyr Lys Glu Cys Lys Ala Thr Lys Ala His Phe Val Ala Ala Asp
225                 230                 235                 240

Tyr Gly His Met Asp Met Leu Asp Asp Asp Leu Pro Gly Phe Val Gly
                245                 250                 255

Phe Met Ala Gly Cys Met Cys Lys Asn Gly Gln Arg Lys Lys Ser Glu
            260                 265                 270

Met Arg Ser Phe Val Gly Gly Ile Val Ala Phe Leu Lys Tyr Ser
        275                 280                 285

Leu Trp Gly Glu Lys Ala Glu Ile Arg Leu Ile Val Lys Asp Pro Ser
    290                 295                 300

Val Ser Pro Ala Lys Leu Asp Pro Ser Pro Glu Leu Glu Glu Ala Ser
305                 310                 315                 320

Gly Ile Phe Val

<210> SEQ ID NO 2
<211> LENGTH: 318
<212> TYPE: PRT
<213> ORGANISM: Arabidopsis thaliana

<400> SEQUENCE: 2

Met Ser Ser Ser Ser Arg Asn Ala Phe Glu Asp Gly Lys Tyr Lys
1               5                   10                  15

Ser Asn Leu Leu Thr Leu Asp Ser Ser Arg Cys Cys Lys Ile Thr
            20                  25                  30

Pro Ser Ser Arg Ala Ser Pro Ser Pro Lys Gln Leu Leu Val Ala
        35                  40                  45

Thr Pro Val Glu Glu Gly Asp Tyr Pro Val Val Met Leu Leu His Gly
    50                  55                  60

Tyr Leu Leu Tyr Asn Ser Phe Tyr Ser Gln Leu Met Leu His Val Ser
65                  70                  75                  80

Ser His Gly Phe Ile Leu Ile Ala Pro Gln Leu Tyr Ser Ile Ala Gly
                85                  90                  95

Pro Asp Thr Met Asp Glu Ile Lys Ser Thr Ala Glu Ile Met Asp Trp
            100                 105                 110

Leu Ser Val Gly Leu Asn His Phe Leu Pro Ala Gln Val Thr Pro Asn
        115                 120                 125

Leu Ser Lys Phe Ala Leu Ser Gly His Ser Arg Gly Gly Lys Thr Ala
    130                 135                 140
```

```
Phe Ala Val Ala Leu Lys Lys Phe Gly Tyr Ser Ser Asn Leu Lys Ile
145                 150                 155                 160

Ser Thr Leu Ile Gly Ile Asp Pro Val Asp Gly Thr Gly Lys Gly Lys
                165                 170                 175

Gln Thr Pro Pro Val Leu Ala Tyr Leu Pro Asn Ser Phe Asp Leu
            180                 185                 190

Asp Lys Thr Pro Ile Leu Val Ile Gly Ser Gly Leu Gly Glu Thr Ala
        195                 200                 205

Arg Asn Pro Leu Phe Pro Cys Ala Pro Pro Gly Val Asn His Arg
    210                 215                 220

Glu Phe Phe Arg Glu Cys Gln Gly Pro Ala Trp His Phe Val Ala Lys
225                 230                 235                 240

Asp Tyr Gly His Leu Asp Met Leu Asp Asp Thr Lys Gly Ile Arg
            245                 250                 255

Gly Lys Ser Ser Tyr Cys Leu Cys Lys Asn Gly Glu Glu Arg Arg Pro
                260                 265                 270

Met Arg Arg Phe Val Gly Gly Leu Val Val Ser Phe Leu Lys Ala Tyr
            275                 280                 285

Leu Glu Gly Asp Asp Arg Glu Leu Val Lys Ile Lys Asp Gly Cys His
    290                 295                 300

Glu Asp Val Pro Val Glu Ile Gln Glu Phe Glu Val Ile Met
305                 310                 315

<210> SEQ ID NO 3
<211> LENGTH: 329
<212> TYPE: PRT
<213> ORGANISM: Citrus sinensis

<400> SEQUENCE: 3

Met Ala Ala Met Val Asp Ala Lys Pro Ala Ala Ser Val Gln Gly Thr
1               5                   10                  15

Pro Leu Leu Ala Thr Ala Thr Leu Pro Val Phe Thr Arg Gly Ile Tyr
            20                  25                  30

Ser Thr Lys Arg Ile Thr Leu Glu Thr Ser Ser Pro Ser Ser Pro Pro
        35                  40                  45

Pro Pro Lys Pro Leu Ile Ile Val Thr Pro Ala Gly Lys Gly Thr Phe
50                  55                  60

Asn Val Ile Leu Phe Leu His Gly Thr Ser Leu Ser Asn Lys Ser Tyr
65                  70                  75                  80

Ser Lys Ile Phe Asp His Ile Ala Ser His Gly Phe Ile Val Val Ala
            85                  90                  95

Pro Gln Leu Tyr Thr Ser Ile Pro Pro Ser Ala Thr Asn Glu Leu
        100                 105                 110

Asn Ser Ala Ala Glu Val Ala Glu Trp Leu Pro Gln Gly Leu Gln Gln
            115                 120                 125

Asn Leu Pro Glu Asn Thr Glu Ala Asn Val Ser Leu Val Ala Val Met
    130                 135                 140

Gly His Ser Arg Gly Gly Gln Thr Ala Phe Ala Leu Ser Leu Arg Tyr
145                 150                 155                 160

Gly Phe Gly Ala Val Ile Gly Leu Asp Pro Val Ala Gly Thr Ser Lys
            165                 170                 175

Thr Thr Gly Leu Asp Pro Ser Ile Leu Ser Phe Asp Ser Phe Asp Phe
        180                 185                 190

Ser Ile Pro Val Thr Val Ile Gly Thr Gly Leu Gly Gly Val Ala Arg
    195                 200                 205
```

```
Cys Ile Thr Ala Cys Ala Pro Glu Gly Ala Asn His Glu Glu Phe Phe
        210                 215                 220

Asn Arg Cys Lys Asn Ser Ser Arg Ala His Phe Val Ala Thr Asp Tyr
225                 230                 235                 240

Gly His Met Asp Ile Leu Asp Asp Asn Pro Ser Asp Val Lys Ser Trp
                245                 250                 255

Ala Leu Ser Lys Tyr Phe Cys Lys Asn Gly Asn Glu Ser Arg Asp Pro
                260                 265                 270

Met Arg Arg Cys Val Ser Gly Ile Val Val Ala Phe Leu Lys Asp Phe
            275                 280                 285

Phe Tyr Gly Asp Ala Glu Asp Phe Arg Gln Ile Leu Lys Asp Pro Ser
290                 295                 300

Phe Ala Pro Ile Lys Leu Asp Ser Val Glu Tyr Ile Asp Ala Ser Ser
305                 310                 315                 320

Met Leu Thr Thr Thr His Val Lys Val
                325

<210> SEQ ID NO 4
<211> LENGTH: 319
<212> TYPE: PRT
<213> ORGANISM: Triticum aestivum

<400> SEQUENCE: 4

Met Ala Ala Ala Ala Pro Ala Glu Thr Met Asn Lys Ser Ala Ala Gly
1                   5                   10                  15

Ala Glu Val Pro Glu Ala Phe Thr Ser Val Phe Gln Pro Gly Lys Leu
                20                  25                  30

Ala Val Glu Ala Ile Gln Val Asp Glu Asn Ala Ala Pro Thr Pro Pro
            35                  40                  45

Ile Pro Val Leu Ile Val Ala Pro Lys Asp Ala Gly Thr Tyr Pro Val
        50                  55                  60

Ala Met Leu Leu His Gly Phe Phe Leu His Asn His Phe Tyr Glu His
65                  70                  75                  80

Leu Leu Arg His Val Ala Ser His Gly Phe Ile Ile Val Ala Pro Gln
                85                  90                  95

Phe Ser Ile Ser Ile Ile Pro Ser Gly Asp Ala Glu Asp Ile Ala Ala
                100                 105                 110

Ala Ala Lys Val Ala Asp Trp Leu Pro Asp Gly Leu Pro Ser Val Leu
            115                 120                 125

Pro Lys Gly Val Glu Pro Glu Leu Ser Lys Leu Ala Leu Ala Gly His
        130                 135                 140

Ser Arg Gly Gly His Thr Ala Phe Ser Leu Ala Leu Gly His Ala Lys
145                 150                 155                 160

Thr Gln Leu Thr Phe Ser Ala Leu Ile Gly Leu Asp Pro Val Ala Gly
                165                 170                 175

Thr Gly Lys Ser Ser Gln Leu Gln Pro Lys Ile Leu Thr Tyr Glu Pro
            180                 185                 190

Ser Ser Phe Gly Met Ala Met Pro Val Leu Val Ile Gly Thr Gly Leu
        195                 200                 205

Gly Glu Glu Lys Lys Asn Ile Phe Phe Pro Cys Ala Pro Lys Asp
    210                 215                 220

Val Asn His Ala Glu Phe Tyr Arg Glu Cys Arg Pro Pro Cys Tyr Tyr
225                 230                 235                 240

Phe Val Thr Lys Asp Tyr Gly His Leu Asp Met Leu Asp Asp Asp Ala
                245                 250                 255
```

```
Pro Lys Phe Ile Thr Cys Val Cys Lys Asp Gly Asn Gly Cys Lys Gly
            260                 265                 270

Lys Met Arg Arg Cys Val Ala Gly Ile Met Val Ala Phe Leu Asn Ala
        275                 280                 285

Ala Leu Gly Glu Lys Asp Ala Asp Leu Glu Ala Ile Leu Arg Asp Pro
    290                 295                 300

Ala Val Ala Pro Thr Thr Leu Asp Pro Val Glu His Arg Val Ala
305                 310                 315

<210> SEQ ID NO 5
<211> LENGTH: 323
<212> TYPE: PRT
<213> ORGANISM: Triticum aestivum

<400> SEQUENCE: 5

Met Ala Ala Met Ala Thr Thr Val Phe Gln Ala Gly Pro Met Glu Val
1               5                   10                  15

Asp Val Lys His Val Asp Lys Ser Met Ile Pro Asn Leu Ala Arg Pro
            20                  25                  30

Leu Met Val Val Ala Pro Lys Glu Thr Gly Ala Tyr Pro Val Ile Val
        35                  40                  45

Phe Leu His Gly Trp Asn Met Leu Asn Ser Trp Tyr Glu Gln Leu Leu
    50                  55                  60

Thr His Val Ala Ser His Gly Phe Ile Ala Val Ala Pro Gln Leu Tyr
65                  70                  75                  80

Trp Met Val Ser Glu Pro Asp Ala Asp Ile Asp Ala Thr Lys Arg
                85                  90                  95

Ile Thr Asn Trp Leu Ala Asp His Asp Lys Gly Leu Ala His Val Leu
            100                 105                 110

Lys Asp Val Leu Lys Leu Glu His Val Glu Pro Asp Leu Ser Lys Leu
        115                 120                 125

Ala Leu Ala Gly His Ser Arg Gly Gly Gln Thr Ala Phe Ala Val Ala
    130                 135                 140

Leu Gly Leu Gly Asp Ala Lys Thr Lys Leu Glu Leu Lys Phe Ser Ala
145                 150                 155                 160

Leu Ile Gly Val Asp Pro Val Ala Gly Val Ser Arg Ala Gln Gln Leu
                165                 170                 175

Glu Pro Lys Val Leu Thr Phe Glu Pro Asp Cys Leu Asp Val Gly Met
            180                 185                 190

Pro Val Leu Val Met Gly Thr Gly Leu Gly Pro Lys His Ile Gly Gly
        195                 200                 205

Phe Pro Cys Ala Pro Val Gly Val Asn His Ala Glu Phe Tyr Lys Glu
    210                 215                 220

Cys Ala Pro Pro Arg Tyr His Leu Val Val Lys Asp Tyr Gly His Leu
225                 230                 235                 240

Asp Met Leu Asp Asp Asn Val Pro Tyr Ile Ile Asn Asn Cys Met Cys
                245                 250                 255

Met Arg Asn Gln His Asp Thr Lys Asp Leu Ala Arg Arg Thr Met Gly
            260                 265                 270

Gly Ala Met Val Ala Phe Leu Arg Ala Lys Leu Arg Ile Asp Val Arg
        275                 280                 285

Asp Leu Ile Ala Ile Tyr His Asn Pro Glu Ile Ala Pro Ala Val Leu
    290                 295                 300
```

```
Asp Gln Val Asp Glu Phe Leu Pro Cys Phe Val Gly Arg Pro Asn Pro
305                 310                 315                 320

Ser Ser Val

<210> SEQ ID NO 6
<211> LENGTH: 213
<212> TYPE: PRT
<213> ORGANISM: Brassica oleracea

<400> SEQUENCE: 6

Met Ser Pro Ser Phe Leu Phe Thr Leu Phe Leu Ile Lys Glu Met
1               5                   10                  15

Ser Ser Ser Ser Ala Asn Ser Phe Glu Asp Gly Lys Tyr Lys Thr
                20                  25                  30

Asp Leu Leu Thr Val Gly Leu Ser Ser Cys Cys Trp Lys Lys Pro Ser
            35                  40                  45

Ser Ser Pro Thr Pro Gln Ser Pro Pro Lys Arg Leu Leu Val Ala Thr
50                  55                  60

Pro Val Glu Glu Gly Glu Tyr Pro Val Val Met Leu Leu His Gly Tyr
65                  70                  75                  80

Leu Leu Tyr Asn Ser Phe Tyr Ser Gln Leu Met Leu His Val Ser Ser
                85                  90                  95

His Gly Phe Ile Val Ile Ala Pro Gln Leu Tyr Ser Ile Ala Gly Pro
            100                 105                 110

Asp Thr Met Asp Glu Ile Lys Ser Thr Ala Glu Ile Ile Asp Trp Leu
        115                 120                 125

Ser Val Gly Leu Asn His Phe Leu Pro Pro Gln Val Thr Pro Asn Leu
    130                 135                 140

Ser Lys Phe Ala Leu Ser Gly His Ser Arg Gly Gly Lys Thr Ala Phe
145                 150                 155                 160

Ala Leu Ala Leu Lys Lys Phe Gly Tyr Ser Ser Asp Leu Lys Ile Ser
                165                 170                 175

Ala Leu Ile Gly Ile Asp Val Gly Thr Val Phe Trp Thr Asn Gly Tyr
            180                 185                 190

Gly Gln Tyr Ser Gly Glu Phe Phe Glu Gln Phe Asp Cys Arg Asn Asp
        195                 200                 205

Arg Ile Val Glu Ser
    210

<210> SEQ ID NO 7
<211> LENGTH: 324
<212> TYPE: PRT
<213> ORGANISM: Brassica oleracea

<400> SEQUENCE: 7

Met Ala Gly Lys Glu Asp Ser Glu Thr Phe Phe Ser Ala Ala Thr Pro
1               5                   10                  15

Leu Ala Phe Glu Leu Gly Ser Leu Pro Thr Thr Val Ile Pro Ala Asp
                20                  25                  30

Pro Ser Ala Thr Asp Leu Thr Ala Pro Pro Lys Pro Val Ile Ile Thr
            35                  40                  45

Ser Pro Thr Val Ala Gly Thr Tyr Pro Val Val Leu Phe Phe His Gly
        50                  55                  60

Phe Tyr Leu Arg Asn Tyr Phe Tyr Ser Asp Val Ile Asn His Val Ala
65                  70                  75                  80

Ser His Gly Tyr Ile Val Val Ala Pro Gln Leu Cys Lys Ile Leu Pro
```

```
                     85                  90                  95
Pro Gly Gly Gln Val Glu Val Asp Asp Ala Gly Lys Val Ile Asn Trp
                100                 105                 110
Thr Ser Lys Asn Leu Lys Ala His Leu Pro Ser Ser Val Asn Ala Asn
            115                 120                 125
Gly Asn Tyr Thr Ala Leu Val Gly His Ser Arg Gly Gly Lys Thr Ala
        130                 135                 140
Phe Ala Val Ala Leu Gly His Ala Ala Thr Leu Asp Pro Ser Ile Lys
145                 150                 155                 160
Phe Ser Ala Leu Val Gly Ile Asp Pro Val Ala Gly Ile Ser Lys Cys
                165                 170                 175
Ile Arg Thr Asp Pro Glu Ile Leu Thr Tyr Lys Pro Glu Ser Phe Asp
                180                 185                 190
Leu Asp Met Pro Val Ala Val Ile Gly Thr Gly Leu Gly Pro Lys Ser
            195                 200                 205
Asn Met Leu Met Pro Pro Cys Ala Pro Ala Glu Val Asn His Glu Glu
        210                 215                 220
Phe Tyr Ile Glu Cys Lys Ala Thr Lys Gly His Phe Val Ala Ala Asp
225                 230                 235                 240
Tyr Gly His Met Asp Met Leu Asp Asp Asn Leu Pro Gly Phe Val Gly
                245                 250                 255
Phe Met Ala Gly Cys Met Cys Lys Asn Gly Lys Arg Lys Lys Ser Glu
                260                 265                 270
Met Arg Ser Phe Val Gly Gly Ile Val Val Ala Phe Leu Lys Tyr Ser
            275                 280                 285
Ile Trp Gly Glu Met Ser Glu Ile Arg Gln Ile Leu Lys Asp Pro Ser
        290                 295                 300
Val Ser Pro Ala Arg Leu Asp Pro Ser Pro Glu Leu Glu Glu Ala Ser
305                 310                 315                 320
Gly Tyr Leu Val

<210> SEQ ID NO 8
<211> LENGTH: 321
<212> TYPE: PRT
<213> ORGANISM: Brassica oleracea

<400> SEQUENCE: 8

Met Ser Ser Ser Ser Arg Asn Ala Phe Val Asp Gly Lys Tyr Lys
1               5                   10                  15
Pro Asp Leu Leu Thr Val Asp Leu Ala Ser Arg Cys Arg Cys Tyr Lys
                20                  25                  30
Thr Thr Pro Ser Ser Ser Leu Thr Pro Pro Pro Pro Lys Ser Leu
            35                  40                  45
Leu Val Ala Thr Pro Val Glu Glu Gly Glu Tyr Pro Val Val Met Leu
50                  55                  60
Leu His Gly Tyr Leu Leu Tyr Asn Ser Phe Tyr Ser Gln Leu Met Leu
65                  70                  75                  80
His Val Ser Ser Tyr Gly Phe Ile Val Ile Ala Pro Gln Leu Tyr Asn
                85                  90                  95
Ile Ala Gly Pro Asp Thr Ile Asp Glu Ile Lys Ser Thr Ala Glu Ile
            100                 105                 110
Ile Asp Trp Leu Ser Val Gly Leu Asn His Phe Leu Pro Pro Gln Val
        115                 120                 125
Thr Pro Asn Leu Ser Lys Phe Ala Leu Thr Gly His Ser Arg Gly Gly
```

```
            130                 135                 140
Lys Thr Ala Phe Ala Val Ala Leu Lys Lys Phe Gly Tyr Ser Ser Glu
145                 150                 155                 160

Leu Lys Ile Ser Ala Ile Ile Gly Val Asp Pro Val Asp Gly Thr Gly
                165                 170                 175

Lys Gly Lys Gln Thr Pro Pro Val Leu Thr Tyr Glu Pro Asn Ser
                180                 185                 190

Phe Asn Leu Glu Lys Met Pro Val Leu Val Ile Gly Ser Gly Leu Gly
                195                 200                 205

Glu Leu Ala Arg Asn Pro Leu Phe Pro Pro Cys Ala Pro Thr Gly Val
                210                 215                 220

Asn His Arg Glu Phe Phe Gln Glu Cys Gln Gly Pro Ala Trp His Phe
225                 230                 235                 240

Val Ala Lys Asp Tyr Gly His Leu Asp Met Leu Asp Asp Thr Lys
                245                 250                 255

Gly Leu Arg Gly Lys Ser Ser Tyr Cys Leu Cys Lys Asn Gly Glu Glu
                260                 265                 270

Arg Lys Pro Met Arg Arg Phe Ile Gly Gly Ile Val Val Ser Phe Leu
                275                 280                 285

Met Ala Tyr Leu Glu Asp Asp Asp Cys Glu Leu Val Lys Ile Lys Ala
                290                 295                 300

Gly Cys His Glu Gly Val Pro Val Glu Ile Gln Glu Phe Glu Val Lys
305                 310                 315                 320

Lys

<210> SEQ ID NO 9
<211> LENGTH: 333
<212> TYPE: PRT
<213> ORGANISM: Zea mays

<400> SEQUENCE: 9

Met Ala Ala Ser Pro Val Ala Ile Gly Thr Ala Val Phe Gln Arg Gly
1               5                   10                  15

Pro Leu Arg Val Glu Ala Arg His Val Asp Tyr Ser Gln Val Pro Ser
                20                  25                  30

Val Pro Lys Pro Leu Met Val Val Ala Pro Thr Asp Ala Gly Val Tyr
                35                  40                  45

Pro Val Ala Val Phe Leu His Gly Cys Asn Thr Val Asn Ser Trp Tyr
                50                  55                  60

Glu Ser Leu Leu Ser His Val Ala Ser His Gly Phe Ile Ala Val Ala
65                  70                  75                  80

Pro Gln Leu Tyr Cys Val Thr Leu Asn Met Asn Asp Leu Lys Asp Ile
                85                  90                  95

Asp Ala Thr Arg Gln Val Thr Ala Trp Leu Ala Asp Lys Gln Gln Gly
                100                 105                 110

Leu Ala His Val Leu Ala Asn Ile Leu Gln Leu His Gly Val Arg Pro
                115                 120                 125

Asp Leu Ser Arg Leu Ala Leu Ala Gly His Ser Arg Gly Gly Asp Thr
                130                 135                 140

Ala Phe Ala Val Ala Leu Gly Leu Gly Pro Ala Ala Ser Asp Asp Asp
145                 150                 155                 160

Asp Asn Asn Ala Asp Ala Gly Thr Ser Pro Ala Ala Leu Pro Leu Lys
                165                 170                 175

Phe Ser Ala Leu Ile Gly Val Asp Pro Val Ala Gly Leu Ser Lys Gln
```

```
                    180                 185                 190
Ala Gln Val Glu Pro Lys Val Leu Thr Phe Arg Pro Arg Ser Leu Asp
                195                 200                 205

Pro Gly Met Pro Ala Leu Val Val Gly Thr Gly Leu Gly Pro Lys His
            210                 215                 220

Val Gly Gly Pro Pro Cys Ala Pro Ala Gly Val Asn His Ala Glu Phe
225                 230                 235                 240

Tyr Asp Glu Cys Ala Pro Pro Arg Tyr His Val Val Leu Arg Asp Tyr
                245                 250                 255

Gly His Met Asp Met Leu Asp Asp Gly Val Pro Tyr Val Ile Asn
            260                 265                 270

Asn Cys Met Cys Met Arg Asn Thr Lys Asp Thr Lys Asp Leu Ala Arg
            275                 280                 285

Arg Ala Ile Gly Gly Ala Val Val Ala Phe Leu Arg Ala Thr Leu Glu
            290                 295                 300

Asp Asp Asp Glu Asp Leu Lys Val Val Leu Glu Asn Arg Pro Gly Leu
305                 310                 315                 320

Ser Pro Ala Val Leu Asp Pro Val Gly His Asp Leu Ala
                325                 330

<210> SEQ ID NO 10
<211> LENGTH: 346
<212> TYPE: PRT
<213> ORGANISM: Zea mays

<400> SEQUENCE: 10

Met Asn Leu Ala Ser Ala Val Arg Val Phe Leu Ser Tyr Cys Leu Leu
1               5                   10                  15

Leu His Arg Trp Met Gly Ser Glu Gln Ala Gly Gly Val Phe Asp Gln
            20                  25                  30

Gly Gly His Ser Val Ser Leu Thr Arg Leu Asp Glu Ala Arg Ala Pro
        35                  40                  45

Pro Arg Cys Ala Val Gln Ser Ser Leu Ser Ser Ala Ala Ser Leu Pro
    50                  55                  60

Pro Lys Pro Leu Leu Val Ala Ala Pro Arg Glu Thr Gly Glu Tyr Pro
65                  70                  75                  80

Val Ile Leu Phe Leu His Gly Tyr Leu Ala Val Asn Ser Phe Tyr Ser
                85                  90                  95

Gln Leu Phe Glu His Val Ala Ser His Gly Phe Ile Val Val Gly Pro
            100                 105                 110

Gln Leu Tyr Thr Ile Ser Gly Ala Asp Thr Thr Glu Ile Asn Ser
        115                 120                 125

Ala Ala Ala Val Ile Asp Trp Leu Ala Thr Gly Leu Pro Ser Thr Leu
    130                 135                 140

Pro Leu Gly Val Arg Ala Asp Leu Thr Lys Val Ser Ile Ser Gly His
145                 150                 155                 160

Ser Arg Gly Gly Lys Val Ala Phe Ala Leu Ala Leu Gly His Ala Lys
                165                 170                 175

Ala Lys Leu Ala Val Pro Leu Ala Ala Val Val Ala Val Asp Pro Val
            180                 185                 190

Asp Gly Met Gly Val Gly Lys Gln Thr Pro Pro Ile Leu Thr Gly
        195                 200                 205

Arg His Gly Ser Leu His Val Gly Ala Pro Thr Met Val Ile Gly Thr
    210                 215                 220
```

```
Gly Leu Gly Glu Leu Pro Arg Gly Ser Leu Leu Pro Pro Cys Ala Pro
225                 230                 235                 240

Arg Gly Val Ser His Ala Ala Phe Tyr Asp Glu Leu Asp Gly Ala Ala
            245                 250                 255

Pro Ala Cys His Leu Val Ala Arg Asp Tyr Gly His Thr Asp Met Met
            260                 265                 270

Asp Asp Asp Thr Pro Gly Ala Arg Gly Met Leu Thr Arg Thr Ile Cys
            275                 280                 285

Arg Ser Gly Gly Ala Arg Ala Pro Met Arg Arg Phe Val Ala Gly Ala
            290                 295                 300

Thr Val Ala Phe Leu Lys Lys Trp Val Ala Gly Asp Ala Ala Ala Met
305                 310                 315                 320

Asp Ser Ile Thr Ala Arg Pro Asp Gln Ala Pro Ile Ala Leu Ser Val
            325                 330                 335

Val Glu Phe Gly Asp Glu Lys Ala Ile Ala
            340                 345

<210> SEQ ID NO 11
<211> LENGTH: 312
<212> TYPE: PRT
<213> ORGANISM: Phyllostachys edulis

<400> SEQUENCE: 11

Met Ala Ala Thr Ala Glu Ile Lys Ile Pro Ser Thr Glu Ala Leu Glu
1               5                   10                  15

Ala Val Thr Ser Val Phe Arg Pro Gly Lys Leu Ala Val Glu Leu Val
            20                  25                  30

Pro Val Asp His Asn Ala Val Pro Thr Pro Ile Pro Ile Leu Ile
            35                  40                  45

Val Ala Pro Lys Asp Ala Gly Thr Tyr Pro Val Ala Met Leu Leu His
50                  55                  60

Gly Phe Phe Leu Gln Asn His Phe Tyr Glu His Leu Leu Lys His Val
65                  70                  75                  80

Ala Ser His Gly Phe Ile Met Val Ala Pro Gln Phe His Ala Ile Cys
            85                  90                  95

Thr Gly Glu Thr Glu Asp Ile Ala Ala Ala Lys Val Thr Asp Trp
            100                 105                 110

Leu Pro Glu Gly Leu Pro Ser Val Leu Lys Gly Val Glu Ala Asp
            115                 120                 125

Leu Ser Lys Leu Ala Leu Ala Gly His Ser Arg Gly Gly His Thr Ala
130                 135                 140

Phe Ser Leu Ala Leu Gly His Gly Lys Thr Asn Leu Asn Phe Ala Ala
145                 150                 155                 160

Leu Ile Gly Leu Asp Pro Val Ala Gly Thr Gly Lys Ser Ser Gln Leu
            165                 170                 175

Pro Pro Lys Ile Leu Thr Tyr Lys Pro Ser Ser Phe Asp Val Ala Met
            180                 185                 190

Pro Val Leu Val Ile Gly Thr Gly Leu Gly Glu Glu Lys Lys Asn Val
            195                 200                 205

Leu Phe Pro Pro Cys Ala Pro Lys Asp Val Asn His Arg Glu Phe Tyr
210                 215                 220

Tyr Glu Cys Lys Pro Pro Cys Tyr Tyr Phe Val Thr Lys Asp Tyr Gly
225                 230                 235                 240

His Leu Asp Met Leu Asp Asp Ala Pro Lys Phe Ile Thr Cys Leu
            245                 250                 255
```

```
Cys Lys Asp Gly Asp Asn Cys Lys Asp Lys Met Arg Arg Ala Val Ala
                260                 265                 270

Gly Ile Met Ile Ala Phe Leu Arg Ala Val Leu Asp Glu Lys Asp Gly
            275                 280                 285

Asp Ile Lys Val Ile Leu Lys Asp Pro Gly Leu Ala Pro Val Thr Leu
        290                 295                 300

Asp Pro Val Glu Cys Arg Leu Pro
305                 310

<210> SEQ ID NO 12
<211> LENGTH: 347
<212> TYPE: PRT
<213> ORGANISM: Chenopodium album

<400> SEQUENCE: 12

Met Ala Lys Leu Leu Leu Ile Phe Gly Val Phe Ile Phe Val Asn
1               5                   10                  15

Ser Gln Ala Gln Thr Phe Pro Thr Ile Leu Glu Lys His Asn Ser Glu
                20                  25                  30

Lys Ile Thr Asp Val Phe His Lys Gly Asn Phe Gln Val Thr Asn Asn
            35                  40                  45

Pro Ile Arg Val Lys Arg Tyr Glu Phe Ser Ala Pro Glu Pro Leu Ile
    50                  55                  60

Ile Ile Ser Pro Lys Glu Ala Gly Val Tyr Pro Val Leu Leu Phe Ile
65                  70                  75                  80

His Gly Thr Met Leu Ser Asn Glu Asp Tyr Ser Leu Phe Phe Asn Tyr
                85                  90                  95

Ile Ala Ser His Gly Phe Ile Val Val Ala Pro Lys Leu Phe Arg Leu
            100                 105                 110

Phe Pro Pro Lys Leu Pro Ser Gln Gln Asp Glu Ile Asp Met Ala Ala
        115                 120                 125

Ser Val Ala Asn Trp Met Pro Leu Tyr Leu Gln Val Val Leu Gln Arg
    130                 135                 140

Tyr Val Thr Gly Val Glu Gly Asp Leu Glu Lys Leu Ala Ile Ser Gly
145                 150                 155                 160

His Ser Arg Gly Gly Lys Ser Ala Phe Ala Leu Ala Leu Gly Phe Ser
                165                 170                 175

Asn Ile Lys Leu Asp Val Thr Phe Ser Ala Leu Ile Gly Val Asp Pro
            180                 185                 190

Val Ala Gly Arg Ser Val Asp Arg Thr Leu Pro His Val Leu Thr
        195                 200                 205

Tyr Lys Pro Asn Ser Phe Asn Leu Ser Ile Pro Val Thr Val Ile Gly
    210                 215                 220

Ser Gly Leu Gly Asn His Thr Ile Ser Cys Ala Pro Asn His Val Ser
225                 230                 235                 240

His Gln Gln Phe Tyr Asp Glu Cys Lys Glu Asn Ser Ser His Phe Val
                245                 250                 255

Ile Thr Lys Tyr Gly His Met Asp Met Leu Asn Glu Phe Arg Leu Ser
            260                 265                 270

Pro Ile Ala Val Thr Met Ser Leu Met Cys Ala Gln Ser Phe Arg Pro
        275                 280                 285

Lys Ala Thr Met Arg Arg Thr Leu Gly Gly Ile Met Val Ala Phe Leu
    290                 295                 300

Asn Ala Tyr Phe Arg Asp Asp Gly Arg Gln Tyr Tyr Ala Ile Ile Ala
```

```
                    305                 310                 315                 320
Asn Arg Ser Leu Ala Pro Thr Asn Leu Phe Ala Glu Lys Lys Gly Phe
                325                 330                 335

Asn Phe Gly Phe Ala Thr Thr Tyr Ala Gln Leu
                340                 345

<210> SEQ ID NO 13
<211> LENGTH: 313
<212> TYPE: PRT
<213> ORGANISM: Ricinus communis

<400> SEQUENCE: 13

Met Ser Ser Ser Cys Ala Thr Val Thr Asn Val Tyr Glu Asn Gly Lys
1               5                   10                  15

Tyr Thr Thr Val Val Ala Lys Ile Glu Ser Gly Ser Cys Ala Arg Ser
                20                  25                  30

Ser Leu Pro Leu Pro Leu Pro Lys Pro Leu Leu Ile Ala Met Pro
            35                  40                  45

Ser Glu Ala Gly Glu Phe Pro Val Leu Ile Phe Leu His Gly Tyr Leu
        50                  55                  60

Leu Tyr Asn Ser Phe Tyr Ser Leu Leu Ile Gln His Val Ala Ser His
65                  70                  75                  80

Gly Phe Ile Val Ile Ala Pro Gln Leu Tyr Thr Val Ala Gly Ala Asp
                85                  90                  95

Ser Ala Asp Glu Ile Lys Cys Thr Ala Ala Ile Thr Asn Trp Leu Ser
            100                 105                 110

Lys Gly Leu His His Val Leu Pro Pro His Val Gln Pro Lys Leu Ser
        115                 120                 125

Lys Leu Gly Leu Ala Gly His Ser Arg Gly Gly Lys Ala Ala Phe Ala
130                 135                 140

Leu Ala Leu Gln Lys Ala Gly Ile Ser Thr Ala Leu Lys Phe Ser Ala
145                 150                 155                 160

Leu Ile Gly Val Asp Pro Val Asp Gly Met Asp Lys Gly Lys Gln Thr
                165                 170                 175

Pro Pro Pro Val Leu Thr Tyr Thr Pro His Ser Phe Asp Leu Asp Met
            180                 185                 190

Ala Ala Met Val Ile Gly Ser Gly Leu Gly Glu Val Lys Arg Asn Pro
        195                 200                 205

Met Phe Pro Pro Cys Ala Pro Lys Gly Val Asn His Glu Asp Phe Phe
210                 215                 220

Lys Glu Cys Lys Lys Pro Ala Tyr Tyr Phe Val Val Lys Asp Tyr Gly
225                 230                 235                 240

His Leu Asp Met Leu Asp Asp Asp Thr Asn Gly Ile Arg Gly Lys Ala
                245                 250                 255

Thr Tyr Cys Leu Cys Val Asn Gly Lys Ser Arg Glu Pro Met Arg Arg
            260                 265                 270

Phe Val Gly Gly Val Leu Val Ala Phe Leu Lys Ala Tyr Leu Gly Gly
        275                 280                 285

Asp Ser Ser Asp Leu Met Thr Ile Thr Asp Gly Gln Thr Gly Pro Val
    290                 295                 300

Glu Leu Gln Ala Ala Glu Cys Tyr Val
305                 310

<210> SEQ ID NO 14
<211> LENGTH: 316
```

```
<212> TYPE: PRT
<213> ORGANISM: Glycine max

<400> SEQUENCE: 14

Met Ala Gln Arg Ala Gln Pro Ala Leu Ala Thr Thr Asp Val Phe Gln
1               5                   10                  15

Lys Gly Asp Ile His Trp Lys Gln Phe Asn Val Glu Thr Ser Thr Ala
            20                  25                  30

Ser Ser Ser Pro Pro Lys Pro Leu Leu Ile Phe Thr Pro Thr Val Pro
        35                  40                  45

Gly Leu Tyr Pro Val Ile Leu Phe Cys His Gly Phe Cys Ile Arg Thr
    50                  55                  60

Ser Tyr Tyr Ser Lys Leu Leu Ala His Ile Val Ser His Gly Phe Ile
65                  70                  75                  80

Leu Val Ala Pro Gln Leu Phe Ser Ile Gly Val Pro Met Phe Gly Pro
                85                  90                  95

Glu Glu Val Lys Cys Glu Gly Arg Val Val Asp Trp Leu Asp Asn Gly
            100                 105                 110

Leu Gln Pro Leu Leu Pro Glu Ser Val Glu Ala Lys Leu Glu Lys Leu
        115                 120                 125

Val Leu Val Gly His Ser Lys Gly Gly Lys Thr Ala Phe Ala Val Ala
    130                 135                 140

Leu Gly Tyr Cys Lys Thr Lys Leu Lys Phe Ser Ala Leu Ile Gly Ile
145                 150                 155                 160

Asp Pro Val Ala Gly Val Ser Lys Cys Lys Pro Cys Arg Ser Leu Pro
                165                 170                 175

Asp Ile Leu Thr Gly Val Pro Arg Ser Phe Asn Leu Asn Ile Pro Val
            180                 185                 190

Ala Val Ile Gly Thr Gly Leu Gly Pro Glu Lys Ala Asn Ser Leu Phe
        195                 200                 205

Pro Pro Cys Ala Pro Asn Gly Val Asn His Lys Glu Phe Phe Ser Glu
    210                 215                 220

Cys Lys Pro Pro Ser Ala Tyr Phe Val Ala Thr Asp Tyr Gly His Met
225                 230                 235                 240

Asp Met Leu Asp Asp Glu Thr Pro Gly Val Ile Gly Thr Met Met Ser
                245                 250                 255

Lys Cys Met Cys Lys Asn Gly Lys Lys Gly Pro Arg Asp Leu Met Arg
            260                 265                 270

Arg Thr Val Gly Gly Leu Val Val Ala Phe Leu Arg Ala Gln Leu Asn
        275                 280                 285

Glu Gln Trp Lys Asp Phe Asp Ala Ile Leu Ala Ser Pro Asn Leu Ala
    290                 295                 300

Pro Ala Lys Leu Asp Asp Val Arg Tyr Leu Pro Thr
305                 310                 315

<210> SEQ ID NO 15
<211> LENGTH: 342
<212> TYPE: PRT
<213> ORGANISM: Ginkgo biloba

<400> SEQUENCE: 15

Met Val Leu Val Lys Asp Val Phe Ser Glu Gly Pro Leu Pro Val Gln
1               5                   10                  15

Ile Leu Ala Ile Pro Gln Ala Asn Ser Ser Pro Cys Ser Lys Leu Ala
            20                  25                  30
```

Asp Lys Asn Gly Thr Ala Thr Thr Pro Ser Pro Cys Arg Pro Pro Lys
            35                  40                  45

Pro Leu Leu Ile Ala Leu Pro Ser Gln His Gly Asp Tyr Pro Leu Ile
 50                  55                  60

Leu Phe Phe His Gly Tyr Val Leu Leu Asn Ser Phe Tyr Ser Gln Leu
 65                  70                  75                  80

Leu Arg His Val Ala Ser His Gly Tyr Ile Ala Ile Ala Pro Gln Met
                85                  90                  95

Tyr Ser Val Ile Gly Pro Asn Thr Thr Pro Glu Ile Ala Asp Ala Ala
            100                 105                 110

Ala Ile Thr Asp Trp Leu Arg Asp Gly Leu Ser Asp Asn Leu Pro Gln
            115                 120                 125

Ala Leu Asn Asn His Val Arg Pro Asn Phe Glu Lys Phe Val Leu Ala
    130                 135                 140

Gly His Ser Arg Gly Gly Lys Val Ala Phe Ala Leu Ala Leu Gly Arg
145                 150                 155                 160

Val Ser Gln Pro Ser Leu Lys Tyr Ser Ala Leu Val Gly Leu Asp Pro
                165                 170                 175

Val Asp Gly Met Gly Lys Asp Gln Gln Thr Ser His Pro Ile Leu Ser
            180                 185                 190

Tyr Arg Glu His Ser Phe Asp Leu Gly Met Pro Thr Leu Val Val Gly
            195                 200                 205

Ser Gly Leu Gly Pro Cys Lys Arg Asn Pro Leu Phe Pro Pro Cys Ala
    210                 215                 220

Pro Gln Gly Val Asn His His Asp Phe Phe Tyr Glu Cys Val Ala Pro
225                 230                 235                 240

Ala Tyr His Phe Val Ala Ser Asp Tyr Gly His Leu Asp Phe Leu Asp
                245                 250                 255

Asp Asp Thr Lys Gly Ile Arg Gly Lys Ala Thr Tyr Cys Leu Cys Lys
            260                 265                 270

Asn Gly Glu Ala Arg Glu Pro Met Arg Lys Phe Ser Gly Gly Ile Val
            275                 280                 285

Val Ala Phe Leu Gln Ala Phe Leu Gly Asp Asn Arg Gly Ala Leu Asn
    290                 295                 300

Asp Ile Met Val Tyr Pro Ser His Ala Pro Val Lys Ile Glu Pro Pro
305                 310                 315                 320

Glu Ser Leu Val Thr Glu Asp Val Lys Ser Pro Glu Val Glu Leu Leu
                325                 330                 335

Arg Arg Ala Val Cys Arg
            340

<210> SEQ ID NO 16
<211> LENGTH: 313
<212> TYPE: PRT
<213> ORGANISM: Pachira macrocarpa

<400> SEQUENCE: 16

Met Ala Gln Leu Leu Glu Thr Lys His Asp Leu Ser Thr Val Val Pro
1               5                   10                  15

Val Phe Val Thr Gly Lys Tyr His Pro Thr Ser Val Ser Val Asp Pro
            20                  25                  30

Ser Asn Ser Ser Pro Ser Ser Pro Lys Pro Leu Leu Ile Phe Thr
            35                  40                  45

Pro Ser Glu Gln Gly Thr Tyr Pro Val Ile Leu Phe Phe His Gly Phe
 50                  55                  60

```
Tyr Leu Arg Asn Asn Phe Tyr Thr Gly Leu Leu His Ile Ser Ser
 65                  70                  75                  80

His Gly Phe Ile Ile Val Ala Pro Gln Leu Ser Asn Ile Ile Pro Pro
                 85                  90                  95

Ser Gly Thr Glu Glu Val Glu His Ala Ala Lys Val Ala Asp Trp Leu
                100                 105                 110

Pro Ser Gly Leu Pro Ser Val Leu Pro Gly Asn Val Glu Ala Asn Leu
                115                 120                 125

Ala Lys Leu Ala Leu Val Gly His Ser Arg Gly Gly Lys Thr Ala Phe
    130                 135                 140

Ala Leu Ala Leu Gly Arg Ala Lys Thr Ala Gln Asn Phe Ser Ala Leu
145                 150                 155                 160

Val Gly Ile Asp Pro Val Ala Gly Asn Arg Phe Gly Glu Thr Ser Pro
                165                 170                 175

Lys Ile Leu Thr Tyr Thr Pro Gly Ser Phe Asp Leu Ser Ile Pro Val
                180                 185                 190

Ala Val Val Gly Thr Gly Leu Gly Pro Glu Ser Lys Gly Cys Met Pro
                195                 200                 205

Cys Pro Cys Ala Pro Thr Gln Tyr Asn His Glu Glu Phe Phe Asn Glu
    210                 215                 220

Cys Lys Pro Pro Arg Val His Phe Asp Ala Lys Asn Tyr Gly His Met
225                 230                 235                 240

Asp Thr Leu Asp Asp Asn Pro Ser Gly Phe Ile Gly Lys Leu Ser Asp
                245                 250                 255

Thr Ile Cys Val Asn Gly Glu Gly Pro Arg Asp Pro Met Arg Arg Cys
                260                 265                 270

Val Gly Gly Ile Val Val Ala Phe Leu Asn Tyr Phe Phe Glu Ala Glu
                275                 280                 285

Lys Glu Asp Phe Met Thr Ile Met Asn Glu Pro Tyr Val Ala Pro Val
    290                 295                 300

Thr Leu Asp Gln Val Gln Phe Asn Val
305                 310

<210> SEQ ID NO 17
<211> LENGTH: 318
<212> TYPE: PRT
<213> ORGANISM: Populus trichocarpa

<400> SEQUENCE: 17

Met Ser Ser Ser Ala Ile Ala Thr Val Thr Thr Val Phe Glu
  1               5                  10                  15

Ala Gly Lys Tyr Thr Thr Val Leu Gln Lys Val Glu Ser Arg Thr Thr
                 20                  25                  30

Cys Cys Thr Ala Lys Thr Ser Pro Pro Leu Pro Val Pro Pro Lys
     35                  40                  45

Pro Leu Leu Ile Val Met Pro Cys Glu Ala Gly Glu Phe Pro Leu Leu
     50                  55                  60

Val Phe Leu His Gly Tyr Leu Leu Tyr Asn Ser Phe Tyr Ser Gln Leu
 65                  70                  75                  80

Leu Gln His Ile Ala Ser His Gly Phe Ile Val Ile Ala Pro Gln Leu
                 85                  90                  95

Tyr Leu Val Ala Gly Gln Asp Ser Ser Asp Glu Ile Lys Ser Val Ala
                100                 105                 110

Ala Thr Thr Asn Trp Leu Ser Glu Gly Leu His His Leu Leu Pro Pro
```

```
            115                 120                 125
His Val Lys Pro Asn Leu Ser Lys Leu Gly Leu Ala Gly His Ser Arg
130                 135                 140

Gly Gly Lys Thr Ala Phe Ala Leu Ala Leu Glu Lys Ala Ala Ala Thr
145                 150                 155                 160

Leu Lys Phe Ser Ala Leu Ile Gly Val Asp Pro Val Asp Gly Met Asp
                165                 170                 175

Lys Gly Lys Gln Thr Pro Pro Val Leu Thr Tyr Val Pro His Ser
            180                 185                 190

Phe Asp Leu Asp Met Ala Ile Met Val Ile Gly Ser Gly Leu Gly Glu
                195                 200                 205

Leu Lys Lys Asn Pro Leu Phe Pro Pro Cys Ala Pro Glu Gly Val Asn
210                 215                 220

His Lys Asp Phe Phe Lys Glu Cys Lys Gly Pro Ala Ser Tyr Phe Val
225                 230                 235                 240

Val Lys Asp Tyr Gly His Leu Asp Met Leu Asp Asp Thr Glu Gly
                245                 250                 255

Ile Arg Gly Lys Thr Thr Tyr Cys Leu Cys Lys Asn Gly Lys Ser Arg
            260                 265                 270

Glu Pro Met Arg Lys Phe Ile Gly Gly Val Val Ala Phe Met Lys
                275                 280                 285

Ala Tyr Leu Gly Gly Asp Ser Ser Asp Leu Met Ala Ile Lys Gly Gly
            290                 295                 300

Gln Thr Gly Pro Val Glu Leu Gln Thr Val Glu Tyr Ile Leu
305                 310                 315

<210> SEQ ID NO 18
<211> LENGTH: 318
<212> TYPE: PRT
<213> ORGANISM: Sorghum bicolor

<400> SEQUENCE: 18

Met Ala Thr Thr Pro Lys Val Leu Glu Glu Pro Ser Ala Val Ile
1               5                   10                  15

Thr Ser Val Phe Gln Pro Gly Lys Leu Ala Val Glu Val Ile Ser Val
                20                  25                  30

Glu His Asp Ala Arg Pro Thr Pro Pro Ile Pro Ile Leu Ile Ala
            35                  40                  45

Ala Pro Lys Asp Ala Gly Thr Tyr Pro Val Ala Ile Leu Leu His Gly
50                  55                  60

Phe Leu Gln Asn Arg Tyr Tyr Glu Gln Leu Leu Lys His Val Ala
65                  70                  75                  80

Ser Phe Gly Phe Ile Met Val Ala Pro Gln Phe His Thr Ser Leu Ile
                85                  90                  95

Ser Asn Ser Asp Ala Asp Ile Ala Ala Ala Lys Val Thr Asp
            100                 105                 110

Trp Leu Pro Glu Gly Leu Pro Thr Val Leu Pro Thr Gly Val Glu Ala
            115                 120                 125

Asp Leu Ser Lys Leu Ala Leu Ala Gly His Ser Arg Gly Gly His Thr
130                 135                 140

Ala Phe Ser Leu Ala Leu Gly Tyr Ala Lys Thr Asn Thr Ser Ser Leu
145                 150                 155                 160

Leu Lys Phe Ser Ala Leu Ile Gly Leu Asp Pro Val Ala Gly Thr Gly
                165                 170                 175
```

```
Lys Asn Ser Gln Leu Pro Pro Ala Ile Leu Thr Tyr Glu Pro Ser Ser
            180                 185                 190

Phe Asp Ile Ala Val Pro Val Leu Val Ile Gly Thr Gly Leu Gly Asp
        195                 200                 205

Glu Arg Glu Asn Ala Leu Phe Pro Pro Cys Ala Pro Val Glu Val Asn
    210                 215                 220

His Ala Glu Phe Tyr Arg Glu Cys Arg Ala Pro Cys Tyr His Leu Val
225                 230                 235                 240

Thr Lys Asp Tyr Gly His Leu Asp Met Leu Asp Asp Ala Pro Lys
                245                 250                 255

Leu Val Thr Cys Leu Cys Lys Glu Gly Asn Thr Cys Lys Asp Val Met
            260                 265                 270

Arg Arg Thr Val Ala Gly Ile Met Val Ala Phe Leu Lys Ala Val Met
        275                 280                 285

Gly Glu Asp Glu Asp Gly Asp Leu Lys Ala Ile Leu Gln His Pro Gly
    290                 295                 300

Leu Ala Pro Thr Ile Leu Asp Pro Val Glu Tyr Arg Leu Ala
305                 310                 315

<210> SEQ ID NO 19
<211> LENGTH: 338
<212> TYPE: PRT
<213> ORGANISM: Sorghum bicolor

<400> SEQUENCE: 19

Met Ala Ser Pro Val Ala Ile Ser Thr Thr Ala Val Phe Lys Arg Gly
1               5                   10                  15

Arg His Pro Val Asp Thr Lys His Val Asp His Ser Gln Val Pro Gly
            20                  25                  30

Val Pro Lys Pro Leu Met Val Val Thr Pro Thr Asp Ala Gly Val Tyr
        35                  40                  45

Pro Val Ala Val Phe Leu His Gly Cys Ser Met Tyr Asn Ser Trp Tyr
    50                  55                  60

Gln Thr Leu Leu Ser His Val Ala Ser His Gly Phe Ile Ala Val Ala
65                  70                  75                  80

Pro Gln Leu Gly Gly Ile Leu Pro Leu Asp Met Lys Asp Leu Lys
                85                  90                  95

Asp Ile Asp Ala Thr Arg Lys Val Thr Ala Trp Leu Ala Asp Asn Leu
            100                 105                 110

Ala His Val Leu Thr Asn Ile Leu His Leu His Gly Val Thr Pro Asp
        115                 120                 125

Leu Ser Arg Leu Ala Leu Ala Gly His Ser Arg Gly Gly Asp Thr Ala
    130                 135                 140

Phe Ala Val Ala Leu Gly Leu Gly Ser Ser Ser Ser Ser Ser Asp Thr
145                 150                 155                 160

Thr Pro Leu Lys Phe Ser Ala Leu Ile Gly Val Asp Pro Val Ala Gly
                165                 170                 175

Leu Ser Lys Glu Leu Gln Leu Glu Pro Lys Val Leu Thr Phe Glu Pro
            180                 185                 190

Arg Ser Leu Asp Pro Gly Met Pro Ala Leu Val Val Gly Thr Gly Leu
        195                 200                 205

Gly Pro Lys Gly Leu Leu Pro Cys Ala Pro Ala Gly Val Ser His Gly
    210                 215                 220

Glu Phe Tyr Asp Glu Cys Ala Pro Pro Arg Tyr His Val Val Val Arg
225                 230                 235                 240
```

```
Asp Tyr Gly His Leu Asp Met Leu Asp Asp Gly Val Pro Tyr Val
                245                 250                 255

Ile Ser Asn Cys Met Cys Lys Arg Asn Thr Asn Thr Lys Asp Leu
            260                 265                 270

Ala Arg Arg Ala Ile Gly Gly Ala Met Val Ala Phe Leu Arg Ala Lys
        275                 280                 285

Leu Glu Asp Asp Glu Asp Leu Arg Ala Val Leu Gln Asn Ser Pro
    290                 295                 300

Gly Leu Ser Pro Ala Val Leu Asp Pro Val Glu Tyr Asp Asp Glu
305                 310                 315                 320

Ala Met Asp Gly Pro Gly Cys Ala Gly Asn Asn Gly Val Ala Gly Ala
                325                 330                 335

Ser Gly
```

<210> SEQ ID NO 20
<211> LENGTH: 319
<212> TYPE: PRT
<213> ORGANISM: Vitis vinifera

<400> SEQUENCE: 20

```
Met Ala Leu Leu Gly Gly Asn Pro Ser Thr Gln Gly Ile Lys Leu Asp
1               5                   10                  15

Leu Lys Thr Thr Thr Ser Val Phe Glu Pro Gly Asn Leu Ser Val Thr
            20                  25                  30

Cys Ile Arg Val Glu Thr Ser Asn Ile Ala Ser Pro Pro Lys Pro Leu
        35                  40                  45

Leu Ile Val Thr Pro Thr Ile Gln Gly Thr Tyr Pro Val Leu Leu Phe
    50                  55                  60

Leu His Gly Phe Glu Leu Arg Asn Thr Phe Tyr Thr Gln Leu Leu Gln
65                  70                  75                  80

Leu Ile Ser Ser His Gly Tyr Ile Val Val Ala Pro Gln Leu Tyr Gly
                85                  90                  95

Leu Leu Pro Pro Ser Gly Ile Gln Glu Ile Lys Ser Ala Ala Ala Val
            100                 105                 110

Thr Asn Trp Leu Ser Ser Gly Leu Gln Ser Val Leu Pro Glu Asn Val
        115                 120                 125

Lys Pro Asp Leu Leu Lys Leu Ala Leu Ser Gly His Ser Arg Gly Gly
    130                 135                 140

Lys Thr Ala Phe Ala Leu Ala Leu Gly Tyr Ala Asp Thr Ser Leu Asn
145                 150                 155                 160

Phe Ser Ala Leu Leu Gly Leu Asp Pro Val Gly Gly Leu Ser Lys Cys
                165                 170                 175

Ser Gln Thr Val Pro Lys Ile Leu Thr Tyr Val Pro His Ser Phe Asn
            180                 185                 190

Leu Ala Ile Pro Val Cys Val Ile Gly Thr Gly Leu Gly Asp Glu Pro
        195                 200                 205

Arg Asn Cys Leu Thr Cys Pro Cys Ala Pro Asp Gly Val Asn His Val
    210                 215                 220

Glu Phe Phe Ser Glu Cys Lys Pro Pro Cys Ser His Phe Val Thr Thr
225                 230                 235                 240

Glu Tyr Gly His Leu Asp Met Leu Asp Asp His Leu Ser Gly Cys Ile
                245                 250                 255

Gly Ala Ile Ser Gly Tyr Ile Cys Lys Ser Gly Lys Gly Pro Arg Asp
            260                 265                 270
```

```
Pro Met Arg Arg Cys Val Gly Gly Leu Phe Val Ala Phe Leu Lys Ala
    275                 280                 285

Tyr Leu Glu Gly Gln Thr Gly Asp Phe Lys Ala Ile Val Asp Glu Pro
    290                 295                 300

Asp Leu Ala Pro Val Lys Leu Asp Pro Val Glu Phe Ile Glu Ala
305                 310                 315

<210> SEQ ID NO 21
<211> LENGTH: 341
<212> TYPE: PRT
<213> ORGANISM: Physcomitrella patens

<400> SEQUENCE: 21

Met Glu Asp Pro Ile Pro Asn Val His Gly Ile Tyr Glu Asp Gly
1               5                   10                  15

Pro Phe Lys Ile Glu Ile Val His Val Asp Asp Ala Ser Ser Ser
                20                  25                  30

Thr Cys Leu Lys Lys Ser Arg Ala Ala Val Asp Arg Glu Asn Leu Ser
    35                  40                  45

Pro Lys Pro Leu Val Val Ala Leu Pro Lys Glu Glu Gly Val Tyr Pro
    50                  55                  60

Val Ile Gln Phe His His Gly Phe Thr Leu Gln Asn Met Phe Tyr Ser
65                  70                  75                  80

Gln Ile Ile Ser His Ile Ala Ser Tyr Gly Phe Ile Val Ala Pro
                85                  90                  95

Gln Met Tyr Lys Ile Ser Gly Ser Asp Ala Thr Thr Glu Ile Glu Asp
                100                 105                 110

Ala Val Gln Ile Leu Asn Trp Met Pro Thr Gly Leu Val Ala Ala Leu
            115                 120                 125

Pro Glu Thr Leu Ser Lys His Arg Pro Asp Phe Ser Lys Val Ala Leu
    130                 135                 140

Val Gly His Ser Arg Gly Ala Lys Val Val Phe Gly Leu Ala Leu Gly
145                 150                 155                 160

Val Arg Asn Ser Ile Leu Gln Tyr Ser Ala Val Val Gly Leu Asp Pro
                165                 170                 175

Val Asp Gly Met Gly Ile Gly Gln Gln Thr Asn Pro Pro Ile Leu Gln
            180                 185                 190

Phe Ser Glu Gly Ser Leu Asn Leu Gly Val Pro Thr Leu Ile Ile Gly
        195                 200                 205

Thr Gly Leu Gly Pro Leu Arg Lys Asn Phe Leu Phe Pro Ala Cys Ala
    210                 215                 220

Pro Ala Gly Val Ser His Glu Ala Phe Tyr Tyr Asp Ser Ala Ala Pro
225                 230                 235                 240

Ala Phe His Phe Val Ala Ser Lys Gln Gly His Met Asp Phe Leu Asn
                245                 250                 255

Asp Asp Cys Ser Gly Pro Thr Gly Met Phe Ser Tyr Cys Leu Cys Lys
            260                 265                 270

Asn Gly Pro Thr Arg Lys Pro Met Arg Arg Phe Ser Gly Gly Met Val
    275                 280                 285

Val Ala Phe Leu Arg Ala Ala Phe Phe Gly Glu Thr Ala Pro Leu Val
    290                 295                 300

Ala Ala Leu Ala Thr Pro Glu Leu Ala Pro Ile Pro Leu Asp Arg Pro
305                 310                 315                 320

Glu Phe Lys Gly Lys Leu Gly Asp Ala Phe Asn Lys Pro Met Leu Ala
```

Pro Ala Leu Thr Pro
          340

<210> SEQ ID NO 22
<211> LENGTH: 280
<212> TYPE: PRT
<213> ORGANISM: Aquilegia sp.

<400> SEQUENCE: 22

Met Thr Thr Ser Leu Pro Pro Lys Pro Leu Ile Ala Thr Pro
1               5                   10                  15

Ser Glu Glu Gly Gln Phe Pro Val Leu Ile Phe Leu His Gly Phe Leu
            20                  25                  30

Leu Phe Asn Lys Phe Tyr Ser Gln Leu Ile Gln His Ile Ala Ser His
        35                  40                  45

Gly Phe Ile Val Ile Ala Pro Gln Leu Tyr Lys Val Ala Gly Pro Asp
    50                  55                  60

Thr Thr Asp Glu Ile Lys Ser Ala Ala Leu Val Ile Asp Trp Leu Ser
65                  70                  75                  80

Asn Gly Leu His Ser Val Leu Pro Pro Leu Val Gln Pro Asn Leu Ser
                85                  90                  95

Lys Leu Gly Ile Gly Gly His Ser Arg Gly Gly Lys Val Ala Phe Ala
            100                 105                 110

Leu Ala Leu Gly His Ile Lys Thr Ser Leu Lys Tyr Ser Val Leu Leu
        115                 120                 125

Gly Ile Asp Pro Val Asp Gly Met Gly Gln Gly Asn Gln Thr Pro Pro
    130                 135                 140

Pro Val Leu Thr Tyr Thr Pro Arg Ser Phe Asp Phe Asn Met Pro Val
145                 150                 155                 160

Leu Val Ile Gly Ser Gly Leu Gly Glu Thr Lys Lys Asn Ser Leu Phe
                165                 170                 175

Pro Pro Cys Ala Pro Lys Gly Val Asn His Glu Asn Phe Tyr Ser Glu
            180                 185                 190

Cys Cys Ser Pro Ala Cys Tyr Phe Val Val Lys Asp Tyr Gly His Met
        195                 200                 205

Asp Met Leu Asp Asp Asp Thr Gly Gly Val Arg Gly Lys Ala Thr Tyr
    210                 215                 220

Cys Thr Cys Ser Asn Gly Lys Ala Arg Glu Pro Met Arg Thr Phe Val
225                 230                 235                 240

Gly Gly Ile Met Val Ala Phe Met Lys Ala Tyr Met Glu Asn Asp Ser
                245                 250                 255

Arg Asp Leu Met Ala Ile Lys Glu Thr Gln Gly Met Ala Leu Ile Glu
            260                 265                 270

Leu Gln Ser Val Glu Phe Arg Leu
        275                 280

<210> SEQ ID NO 23
<211> LENGTH: 324
<212> TYPE: PRT
<213> ORGANISM: Brachypodium distachyon

<400> SEQUENCE: 23

Met Ala Ala Thr Ala Ala Ala Glu Leu Lys Lys Asn Ser Gly Ala
1               5                   10                  15

Asp Val Leu Glu Ala Val Ile Thr Ser Val Phe Gln Pro Gly Lys Leu

```
                20                  25                  30
Ala Val Glu Val Ile Gln Val Asp His Asn Ala Val Pro Thr Pro Pro
         35                  40                  45

Ile Pro Val Leu Ile Val Ala Pro Lys Asp Ala Gly Thr Tyr Pro Val
 50                  55                  60

Ala Met Leu Leu His Gly Phe Phe Leu Gln Asn His Tyr Tyr Lys Gln
 65                  70                  75                  80

Leu Leu Arg His Val Ala Ser His Gly Phe Ile Met Val Ala Pro Gln
                 85                  90                  95

Phe His Leu Ser Met Ile Pro Thr Gly Asp Thr Lys Asp Ile Glu Ala
            100                 105                 110

Ala Ala Lys Val Ser Asp Trp Leu Pro Glu Gly Leu Pro Ser Val Leu
        115                 120                 125

Pro Lys Gly Val Glu Pro Glu Leu Ser Lys Leu Ala Leu Ala Gly His
    130                 135                 140

Ser Arg Gly Gly His Thr Ala Phe Ser Leu Ala Leu Gly His Ala Lys
145                 150                 155                 160

Ser Asn Leu Ser Phe Ser Ala Leu Ile Gly Ile Asp Pro Val Ala Gly
                165                 170                 175

Thr Gly Lys Ser Ser Gln Leu Ala Pro Lys Ile Leu Thr Tyr Glu Pro
            180                 185                 190

Ser Ser Phe Asn Met Ser Ala Ala Met Pro Val Leu Val Ile Gly Thr
        195                 200                 205

Gly Leu Gly Glu Glu Lys Lys Asn Ile Phe Thr Pro Pro Cys Ala Pro
    210                 215                 220

Lys Asp Val Asn His Arg Glu Phe Tyr Leu Glu Cys Lys Pro Pro Cys
225                 230                 235                 240

Tyr Tyr Phe Val Thr Lys Asp Tyr Gly His Leu Asp Met Leu Asp Asp
                245                 250                 255

Asp Ala Pro Met Val Ile Thr Cys Leu Cys Lys Asp Gly Gly Ser Cys
            260                 265                 270

Lys Asp Lys Met Arg Arg Cys Val Ala Gly Ile Met Val Ala Phe Leu
        275                 280                 285

Asn Ser Ala Leu Gly Gly Lys Asp Asn Ala Ala His Asp Leu Glu Val
    290                 295                 300

Ile Val Lys Asp Pro Ala Leu Ala Pro Thr Thr Leu Asp Pro Val Glu
305                 310                 315                 320

Cys Arg Leu Glu

<210> SEQ ID NO 24
<211> LENGTH: 306
<212> TYPE: PRT
<213> ORGANISM: Medicago truncatula

<400> SEQUENCE: 24

Met Cys Ser Ser Val Ser Asn Val Phe Glu Thr Gly Asn Tyr Thr Thr
 1               5                  10                  15

Lys Leu Leu Arg Val Asp Ser Cys Ser His Ala Gln Asn Val Pro Pro
                20                  25                  30

Pro Lys Ser Leu Leu Ile Ala Thr Pro Ile Glu Gly Glu Phe Pro
            35                  40                  45

Leu Leu Leu Phe Leu His Gly Tyr Leu Leu Asn Ser Phe Tyr Ser
 50                  55                  60

Gln Leu Ile Gln His Val Ala Ser His Gly Phe Ile Val Ile Ala Pro
```

```
            65                  70                  75                  80
        Gln Leu Tyr Thr Val Ala Gly Pro Asp Ile Thr Glu Glu Ile Tyr Ser
                        85                  90                  95

Val Ala Ala Ile Thr Asn Trp Leu Ser Lys Gly Leu Ser Lys Ile Leu
                       100                 105                 110

Pro Leu Asn Ile Lys Pro Asn Phe His Lys Leu Ala Leu Gly Gly His
                       115                 120                 125

Ser Arg Gly Gly Lys Thr Ser Phe Ala Val Ala Leu Arg Lys Leu Asn
                       130                 135                 140

Met Thr Thr Asp Leu Lys Phe Ser Ala Ile Ile Gly Val Asp Pro Val
        145                 150                 155                 160

Asp Gly Met Asp Lys Gly Lys Gln Thr Ser Pro Ile Phe Thr Tyr
                       165                 170                 175

Val Pro His Ser Phe Asp Tyr Asp Met Ala Thr Leu Val Ile Gly Phe
                       180                 185                 190

Gly Leu Gly Asp Val Lys Lys Asn Pro Leu Phe Pro Pro Cys Ala Pro
                       195                 200                 205

Lys Gly Val Asn His Glu Asp Phe Phe Ser Glu Cys Glu Lys Pro Ser
                       210                 215                 220

Trp Tyr Phe Val Ala Lys Asp Tyr Gly His Val Asp Met Leu Asp Asp
        225                 230                 235                 240

Asp Thr Lys Gly Val Arg Gly Lys Val Ser Tyr Cys Leu Cys Lys Asn
                       245                 250                 255

Gly Glu Ser Arg Lys Pro Met Arg Met Phe Val Gly Gly Val Met Val
                       260                 265                 270

Ala Phe Leu Lys Ala Tyr Leu His Gly Asp Asn Val Asp Leu Leu Ala
                       275                 280                 285

Ile Arg Asp Lys Asn Leu Ser Val Pro Ile Glu Met Lys Phe Asp Tyr
                       290                 295                 300

Phe Val
        305

<210> SEQ ID NO 25
<211> LENGTH: 306
<212> TYPE: PRT
<213> ORGANISM: Piper betle

<400> SEQUENCE: 25

Met Ala Ala Ser Ser Val Phe Glu Met Gly Lys Leu Glu Val His Val
        1               5                  10                  15

Lys Ser Val Asn Gln Ser Asn Ser Ser Pro Pro Lys Ser Leu Leu
                        20                  25                  30

Ile Ser Tyr Pro Ser Gln Lys Gly Asp Tyr Gly Val Val Leu Phe Leu
                        35                  40                  45

His Gly Phe Leu Ile Ser Asn Ser Phe Tyr Lys Glu Leu Ile Ser His
                        50                  55                  60

Ile Ser Ser His Gly Tyr Ile Val Val Ala Pro Arg Ile Ile Tyr Pro
        65                  70                  75                  80

Cys Leu Gln Asp Glu Ile Asn Ser Ala Ala Gln Val Ala Asn Trp Leu
                        85                  90                  95

Pro Glu Gly Leu Gln Ala Ala Leu Pro Pro Asn Val Gln Pro Asn Thr
                       100                 105                 110

Ser Lys Leu Thr Leu Ala Gly His Ser Arg Gly Gly Lys Ala Ala Phe
                       115                 120                 125
```

```
Cys Met Leu Leu Gly Leu Ala Gly Ser Pro Leu Thr Val Gln Phe Ser
    130                 135                 140

Gly Leu Ile Gly Val Asp Pro Val Ala Gly Phe Gln Ile Pro Gly Ile
145                 150                 155                 160

Asn Tyr Lys Met Glu Ile Pro Pro Lys Ile Ile Thr Asn Asn Ser Lys
            165                 170                 175

Pro Phe Asp Ile Asn Val Pro Thr Leu Ile Ile Gly Thr Glu Leu Gly
        180                 185                 190

Glu Glu Ala Lys Gly Cys Leu Ala Pro Pro Tyr Ala Pro Ala Gly Leu
    195                 200                 205

Asn Tyr Glu Gln Phe Tyr Glu Lys Ser Lys Glu Pro Ser Tyr Gln Phe
210                 215                 220

Val Ala Lys Gly Tyr Gly His Val Asp Met Leu Asp Asp Ile Ser Lys
225                 230                 235                 240

Asn Asp Leu Met Gly Lys Leu Thr Tyr Cys Val Cys Lys Asn Gly Lys
            245                 250                 255

Glu Arg Glu Pro Met Arg Arg Thr Ala Gly Gly Leu Met Val Ala Phe
        260                 265                 270

Leu Lys Ala Phe Ser Asp Gly Gln Arg Asp Asp Leu Asp Ala Ile Leu
    275                 280                 285

Asn Asp Pro Glu Leu Ala Pro Ile Gln Leu Asp Ala Gly Ala Lys Leu
290                 295                 300

Ser Ser
305

<210> SEQ ID NO 26
<211> LENGTH: 327
<212> TYPE: PRT
<213> ORGANISM: Lotus japonicus

<400> SEQUENCE: 26

Met Ser Leu Ser Ile Ser Ser Val Thr His Pro Ser Ser Val Met Gly
1               5                   10                  15

Ser Asp Ala Ser Thr Ala Leu Thr Asn Val Phe Asp Ser Gly Lys Tyr
            20                  25                  30

Thr Thr Lys Phe Gln Arg Ile Glu Ser Asn Ser Cys Asn Gly Thr His
        35                  40                  45

Pro Asp Pro Pro Pro Lys Ser Leu Leu Ile Ala Thr Pro Leu Glu
    50                  55                  60

Gly Gly Glu Phe Pro Val Leu Leu Phe Leu His Gly Tyr Leu Leu Tyr
65                  70                  75                  80

Asn Ser Phe Tyr Ser Gln Leu Ile Gln His Ile Ala Ser His Gly Phe
                85                  90                  95

Ile Val Ile Ala Pro Gln Leu Tyr Ala Val Ala Gly Pro Asp Val Ser
            100                 105                 110

Gly Glu Ile His Ser Thr Ala Ala Ile Lys Asn Trp Leu Ser Glu Gly
        115                 120                 125

Leu Ser Lys Phe Leu Pro Pro Asn Val Thr Pro Asn Ser Ser Lys Leu
    130                 135                 140

Ala Leu Ala Gly His Ser Arg Gly Gly Lys Thr Ala Phe Ala Val Ala
145                 150                 155                 160

Leu Arg Lys Leu Asn Ile Thr Thr Asp Leu Lys Phe Ser Ala Leu Val
                165                 170                 175

Gly Val Asp Pro Val Asp Gly Leu Asp Arg Gly Lys Gln Thr Pro Pro
            180                 185                 190
```

-continued

```
Pro Val Leu Thr Tyr Val Pro His Ser Phe Asp Phe Asp Met Pro Ala
            195                 200                 205

Met Val Ile Gly Ser Gly Leu Gly Asp Val Lys Arg Asn Pro Leu Phe
    210                 215                 220

Pro Pro Cys Ala Pro Lys Thr Val Asn His Glu Asp Phe Phe Asn Glu
225                 230                 235                 240

Cys Asn Lys Pro Ala Trp Tyr Phe Val Ala Lys Asp Tyr Gly His Val
                245                 250                 255

Asp Met Leu Asp Asp Asp Thr Asn Gly Ile Ile Gly Lys Ala Thr Tyr
                260                 265                 270

Cys Leu Cys Lys Asn Gly Glu Ser Arg Lys Pro Met Arg Thr Phe Val
            275                 280                 285

Gly Gly Leu Val Val Ala Phe Leu Lys Ala Tyr Leu Gln Gly Asp Asn
    290                 295                 300

Arg Asp Ser Leu Ala Ile Lys Asp Lys His Leu Ser Ala Pro Val Glu
305                 310                 315                 320

Leu Lys Phe Asp Tyr Phe Val
                325

<210> SEQ ID NO 27
<211> LENGTH: 337
<212> TYPE: PRT
<213> ORGANISM: Oryza sativa Indica

<400> SEQUENCE: 27

Met Ile Ala Phe Ala Ala Gln Ile Leu Ala Phe Cys Leu Leu Leu Leu
1               5                   10                  15

Leu Leu Leu Leu Gln Leu Gln Thr Thr Met Ala Gly Asp Ser Ser
            20                  25                  30

Phe Ser Gly Val Phe Asp His Gly Ser His Gly Val Thr Leu Val Lys
        35                  40                  45

Val Asp Glu Ala Pro Arg Lys Cys Ser Ser Ala Ala Ala Lys Lys
    50                  55                  60

Thr Asp Asp Thr Ala Pro Ala Gly Gly Ala Pro Pro Lys Pro Leu
65                  70                  75                  80

Leu Val Ala Ala Pro Cys Asp Ala Gly Val Tyr Pro Val Val Phe
                85                  90                  95

Leu His Gly Tyr Leu Ala Tyr Asn Ser Phe Tyr Ser Gln Leu Phe Glu
            100                 105                 110

His Val Ala Ser His Gly Phe Val Val Gly Pro Gln Val Asn Gln
            115                 120                 125

Ser Ile Leu Ile Tyr Tyr Phe Ser Tyr Ile Arg Cys Leu Asp Arg Ile
    130                 135                 140

Pro Pro Thr Arg Ser Thr Arg Arg Ala Ala Val Ile Asn Trp Leu Ala
145                 150                 155                 160

Ala Gly Gly Leu Thr Ser Lys Leu Pro Pro Asn Val Arg Ala Asp Ala
                165                 170                 175

Thr Lys Ile Ser Ile Ser Gly His Ser Arg Gly Gly Lys Val Ala Phe
            180                 185                 190

Ala Leu Ala Leu Gly His Ala Asn Val Ser Leu Arg Gly Gly Ala Gly
            195                 200                 205

Gly Ala Thr Ile Ala Ala Leu Val Ala Val Asp Pro Val Asp Gly Phe
    210                 215                 220

Ala Thr Gly Lys Gln Thr Pro Pro Ile Leu Thr Tyr Gly Gly Ala
```

```
225                 230                 235                 240
Asn Ser Leu Arg Val Pro Ala Pro Val Met Val Ile Gly Thr Gly Leu
                245                 250                 255
Gly Gly Leu Ala Arg Ala Ala Pro Leu Leu Pro Ala Cys Ala Pro Pro
                260                 265                 270
Gly Val Ser His Gly Glu Phe Tyr Gly Glu Cys Ala Ala Pro Ala Cys
                275                 280                 285
His Leu Val Ala Arg Asp Tyr Gly His Thr Asp Met Val Val Asp Val
                290                 295                 300
Thr Pro Gly Ser Trp Ala Ser Leu Arg Val Pro Cys Ala Gly Ala Ser
305                 310                 315                 320
Ala Pro Gly Arg Pro Cys Val Gly Ser Ser Ala Pro Trp Ser Arg
                325                 330                 335
Ser

<210> SEQ ID NO 28
<211> LENGTH: 367
<212> TYPE: PRT
<213> ORGANISM: Oryza sativa Japonica

<400> SEQUENCE: 28

Met Ile Ala Phe Ala Ala Gln Ile Leu Ala Phe Cys Leu Leu Leu Leu
1               5                   10                  15
Leu Leu Leu Leu Gln Leu Gln Thr Thr Met Ala Gly Asp Ser Ser
                20                  25                  30
Phe Ser Gly Val Phe Asp His Gly Ser His Gly Val Thr Leu Val Lys
                35                  40                  45
Val Asp Glu Ala Pro Arg Lys Cys Ser Ser Ala Ala Ala Lys Lys
                50                  55                  60
Thr Asp Asp Asp Thr Ala Pro Ala Gly Gly Ala Pro Pro Lys Pro Leu
65                  70                  75                  80
Leu Val Ala Ala Pro Cys Asp Ala Gly Val Tyr Pro Val Val Val Phe
                85                  90                  95
Leu His Gly Tyr Leu Ala Tyr Asn Ser Phe Tyr Ser Gln Leu Phe Glu
                100                 105                 110
His Val Ala Ser His Gly Phe Val Val Val Gly Pro Gln Leu Tyr Thr
                115                 120                 125
Met Ser Gly Pro Asp Thr Thr Asp Glu Ile Asn Ser Ala Ala Ala Val
                130                 135                 140
Ile Asn Trp Leu Ala Ala Gly Gly Leu Thr Ser Lys Leu Pro Pro Asn
145                 150                 155                 160
Val Arg Ala Asp Ala Thr Lys Ile Ser Ile Ser Gly His Ser Arg Gly
                165                 170                 175
Gly Lys Val Ala Phe Ala Leu Ala Leu Gly His Ala Asn Val Ser Leu
                180                 185                 190
Arg Gly Gly Ala Gly Gly Ala Thr Ile Ala Ala Leu Val Ala Val Asp
                195                 200                 205
Pro Val Asp Gly Phe Ala Ala Gly Lys Gln Thr Pro Pro Ile Leu
                210                 215                 220
Thr Tyr Gly Gly Ala Asn Ser Leu Arg Val Pro Ala Pro Val Met Val
225                 230                 235                 240
Ile Gly Thr Gly Leu Gly Gly Leu Ala Arg Ala Ala Pro Leu Leu Pro
                245                 250                 255
Ala Cys Ala Pro Pro Gly Val Ser His Gly Glu Phe Tyr Gly Glu Cys
```

```
                    260                 265                 270
Ala Ala Pro Ala Cys His Leu Val Ala Arg Asp Tyr Gly His Thr Asp
            275                 280                 285

Met Met Asp Asp Val Thr Pro Gly Ala Arg Gly Leu Ala Thr Arg Ala
        290                 295                 300

Val Cys Arg Ser Gly Gly Ala Arg Ala Pro Met Arg Arg Phe Phe Gly
305                 310                 315                 320

Gly Ala Met Val Ala Phe Val Lys Arg Trp Val Glu Gly Pro Glu
                325                 330                 335

Leu Leu Asp Cys Val Arg Ala Arg Pro Glu Thr Ala Pro Val Val Leu
                340                 345                 350

Ser Ala Val Glu Phe Arg Asp Glu Ala Ile Ala Asn His Ser Tyr
            355                 360                 365

<210> SEQ ID NO 29
<211> LENGTH: 356
<212> TYPE: PRT
<213> ORGANISM: Oryza sativa Japonica

<400> SEQUENCE: 29

Met Ile Ala Phe Ala Ala Gln Ile Leu Ala Phe Cys Leu Leu Leu Leu
1               5                   10                  15

Leu Leu Leu Leu Leu Gln Leu Gln Thr Thr Met Ala Gly Asp Ser Ser
                20                  25                  30

Phe Ser Gly Val Phe Asp His Gly Ser His Gly Val Thr Leu Val Lys
            35                  40                  45

Val Asp Glu Ala Pro Arg Lys Cys Ser Ser Ala Ala Ala Lys Lys
50                  55                  60

Thr Asp Asp Asp Thr Ala Pro Ala Gly Gly Ala Pro Pro Lys Pro Leu
65                  70                  75                  80

Leu Val Ala Ala Pro Cys Asp Ala Gly Val Tyr Pro Val Val Phe
            85                  90                  95

Leu His Gly Tyr Leu Ala Tyr Asn Ser Phe Tyr Ser Gln Leu Phe Glu
                100                 105                 110

His Val Ala Ser His Gly Phe Val Val Val Gly Pro Gln Leu Phe Leu
            115                 120                 125

Gly Cys Glu Leu Ile Leu Ser Asn Asn Phe Asp Ala Lys Met Leu Tyr
        130                 135                 140

Thr Met Ser Gly Pro Asp Thr Thr Asp Glu Ile Asn Ser Ala Ala Ala
145                 150                 155                 160

Val Ile Asn Trp Leu Ala Ala Gly Gly Leu Thr Ser Lys Leu Pro Pro
                165                 170                 175

Asn Val Arg Ala Asp Ala Thr Lys Ile Ser Ile Ser Gly His Ser Arg
            180                 185                 190

Gly Gly Lys Val Ala Phe Ala Leu Ala Leu Gly His Ala Asn Gln Thr
        195                 200                 205

Pro Arg Pro Ile Leu Thr Tyr Gly Gly Ala Asn Ser Leu Arg Leu Pro
    210                 215                 220

Ala Pro Val Met Val Ile Gly Thr Gly Leu Gly Gly Leu Ala Arg Ala
225                 230                 235                 240

Ala Pro Leu Leu Pro Ala Cys Ala Pro Pro Gly Val Ser His Gly Glu
                245                 250                 255

Phe Tyr Gly Glu Cys Ala Ala Pro Ala Cys His Leu Val Ala Arg Asp
            260                 265                 270
```

```
Tyr Gly His Thr Asp Met Met Asp Val Thr Pro Gly Ala Arg Gly
            275                 280                 285

Leu Ala Thr Arg Ala Val Cys Arg Ser Gly Gly Ala Arg Ala Pro Met
290                 295                 300

Arg Arg Phe Phe Gly Gly Ala Met Val Ala Phe Val Lys Arg Trp Val
305                 310                 315                 320

Glu Gly Glu Pro Glu Leu Leu Asp Cys Val Arg Ala Arg Pro Glu Thr
            325                 330                 335

Ala Pro Val Val Leu Ser Ala Val Glu Phe Arg Asp Glu Ala Ile Ala
            340                 345                 350

Asn His Ser Tyr
            355

<210> SEQ ID NO 30
<211> LENGTH: 329
<212> TYPE: PRT
<213> ORGANISM: Picea sitchensis

<400> SEQUENCE: 30

Met Gly Gln Gln Gly Glu Glu Pro Trp Glu Asp Val Phe Lys Pro Gly
1               5                   10                  15

Arg Phe Pro Val Arg Ile Leu Lys Ile Pro Gln Arg Thr Thr His Gly
                20                  25                  30

Ser Thr Thr Ala Ala Ala Pro Lys Pro Leu Leu Leu Ala Leu Pro Ala
            35                  40                  45

Gln Pro Gly Glu Tyr Pro Val Leu Leu Phe Phe His Gly Tyr Leu Leu
        50                  55                  60

Leu Asn Ser Phe Tyr Thr Gln Leu Leu Gln His Ile Ala Ser His Gly
65                  70                  75                  80

Tyr Ile Ala Ile Ala Pro Gln Met Tyr Cys Val Thr Gly Ala Asp Ala
                85                  90                  95

Thr Pro Glu Ile Ala Asp Ala Ala Ala Ile Cys Asn Trp Leu Leu Gln
            100                 105                 110

Gly Leu Ser Ser Tyr Leu Pro Asp Asp Val Arg Pro Asp Phe Gln Asn
        115                 120                 125

Val Ala Met Ala Gly His Ser Arg Gly Gly Lys Val Ala Phe Gly Leu
130                 135                 140

Ala Leu Asp Arg Thr Ser Gln Thr Thr Glu Leu Lys Phe Ser Ala Leu
145                 150                 155                 160

Val Gly Val Asp Pro Val Asp Gly Met Ala Arg Gly Arg Gln Thr Gln
                165                 170                 175

Pro Arg Ile Leu Thr Tyr Lys Pro His Ser Phe Asp Ser Val Ile Pro
            180                 185                 190

Thr Leu Ile Val Gly Ser Gly Leu Gly Ala Val Lys Arg Asn Pro Leu
        195                 200                 205

Phe Pro Pro Cys Ala Pro Glu Gly Val Ser His Arg Glu Phe Phe Ser
210                 215                 220

Glu Cys Ser Ala Pro Ala Tyr His Phe Val Ala Ser Asp Tyr Gly His
225                 230                 235                 240

Met Asp Phe Leu Asp Asp Glu Thr Gly Val Lys Gly Gln Ser Ser
                245                 250                 255

Tyr Cys Leu Cys Lys Asn Gly Val Ala Arg Glu Pro Met Arg Arg Phe
            260                 265                 270

Cys Gly Gly Ile Ile Val Ala Phe Leu Asn Val Cys Leu Gln Asn Asp
        275                 280                 285
```

```
Ser Gly Ala Phe Asn Asp Leu Leu Val His Pro Ser His Ala Pro Val
        290                 295                 300

Lys Leu Glu Pro Pro Glu Ser Phe Val Ser Glu Val Glu His Gln Ala
305                 310                 315                 320

Val Glu Ser Leu Leu Pro Gln Thr Val
                325

<210> SEQ ID NO 31
<211> LENGTH: 322
<212> TYPE: PRT
<213> ORGANISM: Chlamydomonas sp.

<400> SEQUENCE: 31

Met Pro Ser Thr Gln Phe Leu Gly Ala Ser Thr Leu Leu Phe Gly
1               5                   10                  15

Leu Arg Ala Val Met Ser Ser Asp Asp Tyr Ile Lys Arg Gly Asp Leu
                20                  25                  30

Pro Thr Ser Lys Trp Ser Gly Arg Val Thr Leu Arg Val Asp Ser Ala
            35                  40                  45

Met Ala Val Pro Leu Asp Val Val Ile Thr Tyr Pro Ser Ser Gly Ala
50                  55                  60

Ala Ala Tyr Pro Val Leu Val Met Tyr Asn Gly Phe Gln Ala Lys Ala
65                  70                  75                  80

Pro Trp Tyr Arg Gly Ile Val Asp His Val Ser Ser Trp Gly Tyr Thr
                85                  90                  95

Val Val Gln Tyr Thr Asn Gly Gly Leu Phe Pro Ile Val Val Asp Arg
                100                 105                 110

Val Glu Leu Thr Tyr Leu Glu Pro Leu Leu Thr Trp Leu Glu Thr Gln
            115                 120                 125

Ser Ala Asp Ala Lys Ser Pro Leu Tyr Gly Arg Ala Asp Val Ser Arg
130                 135                 140

Leu Gly Thr Met Gly His Ser Arg Gly Gly Lys Leu Ala Ala Leu Gln
145                 150                 155                 160

Phe Ala Gly Arg Thr Asp Val Ser Gly Cys Val Leu Phe Asp Pro Val
                165                 170                 175

Asp Gly Ser Pro Met Thr Pro Glu Ser Ala Asp Tyr Pro Ser Ala Thr
            180                 185                 190

Lys Ala Leu Ala Ala Ala Gly Arg Ser Ala Gly Leu Val Gly Ala Ala
        195                 200                 205

Ile Thr Gly Ser Cys Asn Pro Val Gly Gln Asn Tyr Pro Lys Phe Trp
210                 215                 220

Gly Ala Leu Ala Pro Gly Ser Trp Gln Met Val Leu Ser Gln Ala Gly
225                 230                 235                 240

His Met Gln Phe Ala Arg Thr Gly Asn Pro Phe Leu Asp Trp Ser Leu
                245                 250                 255

Asp Arg Leu Cys Gly Arg Gly Thr Met Met Ser Ser Asp Val Ile Thr
            260                 265                 270

Tyr Ser Ala Ala Phe Thr Val Ala Trp Phe Glu Gly Ile Phe Arg Pro
        275                 280                 285

Ala Gln Ser Gln Met Gly Ile Ser Asn Phe Lys Thr Trp Ala Asn Thr
290                 295                 300

Gln Val Ala Ala Arg Ser Ile Thr Phe Asp Ile Lys Pro Met Gln Ser
305                 310                 315                 320

Pro Gln
```

```
<210> SEQ ID NO 32
<211> LENGTH: 5
<212> TYPE: PRT
<213> ORGANISM: Artificial Sequence
<220> FEATURE:
<223> OTHER INFORMATION: Conserved sequence motif

<400> SEQUENCE: 32

Gly His Ser Arg Gly
1               5

<210> SEQ ID NO 33
<211> LENGTH: 4
<212> TYPE: PRT
<213> ORGANISM: Artificial Sequence
<220> FEATURE:
<223> OTHER INFORMATION: Amino acid sequence motif
<220> FEATURE:
<221> NAME/KEY: VARIANT
<222> LOCATION: (4)..(4)
<223> OTHER INFORMATION: Xaa may be Leu, Ala, Val, Ile, Phe, Tyr, His,
      Gln, Thr, Asn, Met or Ser

<400> SEQUENCE: 33

Gly Asp Ser Xaa
1

<210> SEQ ID NO 34
<211> LENGTH: 78
<212> TYPE: DNA
<213> ORGANISM: Artificial Sequence
<220> FEATURE:
<223> OTHER INFORMATION: Nucleotide sequence showing the fusion of a
      chlorophyllase gene to a His tag and thrombin site

<400> SEQUENCE: 34
catgggcagc agccatcatc atcatcatca cagcagcggc ctggtgccgc gcggcagcca      60
tatggcagcg gctgcccc                                                   78

<210> SEQ ID NO 35
<211> LENGTH: 26
<212> TYPE: PRT
<213> ORGANISM: Artificial Sequence
<220> FEATURE:
<223> OTHER INFORMATION: Amino acid sequence showing the fusion of a
      chlorophyllase gene to a His tag and thrombin site

<400> SEQUENCE: 35

Met Gly Ser Ser His His His His His His Ser Ser Gly Leu Val Pro
1               5                   10                  15

Arg Gly Ser His Met Ala Ala Ala Ala Pro
            20                  25

<210> SEQ ID NO 36
<211> LENGTH: 155
<212> TYPE: DNA
<213> ORGANISM: Artificial Sequence
<220> FEATURE:
<223> OTHER INFORMATION: Nucleotide sequence showing the fusion of a
      chlorophyllase gene to an AprEsignal sequence and an AGK sequence

<400> SEQUENCE: 36
atttttttaa aaggagaggg taaagagtga gaagcaaaaa attgtggatc agtttgctgt      60
ttgctttagc gttaatcttt acgatggcgt tcggcagcac atccagcgcg caggctgctg    120
```

```
gaaaaatggc agcggctgcc ccggccgaaa caatg                              155
```

<210> SEQ ID NO 37
<211> LENGTH: 43
<212> TYPE: PRT
<213> ORGANISM: Artificial Sequence
<220> FEATURE:
<223> OTHER INFORMATION: Amino acid sequence showing the fusion of a
      chlorophyllase gene to an AprEsignal sequence and an AGK sequence

<400> SEQUENCE: 37

Met Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Met Ala Ala Ala Ala Pro Ala Glu Thr Met
        35                  40

<210> SEQ ID NO 38
<211> LENGTH: 77
<212> TYPE: DNA
<213> ORGANISM: Artificial Sequence
<220> FEATURE:
<223> OTHER INFORMATION: Nucleotide sequence showing the fusion of a
      chlorophyllase gene directly to an AprE promoter

<400> SEQUENCE: 38

```
taagtaagtc tactctgaat tttttaaaa ggagagggta actagtggca gcggctgccc     60
cggccgaaac aatgaat                                                   77
```

<210> SEQ ID NO 39
<211> LENGTH: 11
<212> TYPE: PRT
<213> ORGANISM: Artificial Sequence
<220> FEATURE:
<223> OTHER INFORMATION: Amino acid sequence showing the fusion of a
      chlorophyllase gene directly to an AprE promoter

<400> SEQUENCE: 39

Met Ala Ala Ala Ala Pro Ala Glu Thr Met Asn
1               5                   10

<210> SEQ ID NO 40
<211> LENGTH: 156
<212> TYPE: DNA
<213> ORGANISM: Artificial Sequence
<220> FEATURE:
<223> OTHER INFORMATION: Nucleotide sequence showing the fusion of a
      chlorophyllase gene to the Cel A signal sequence

<400> SEQUENCE: 40

```
aaccatgggc tttgggagcg ctcccatcgc gttgtgtccg cttcgcacga ggaggaacgc    60
tttgaaacgc cttttggccc tgctcgcgac cggcgtgtcg atcgtcggcc tgactgcgct   120
agccggcccc ccggcacagg ccatggccgc cgccgc                             156
```

<210> SEQ ID NO 41
<211> LENGTH: 51
<212> TYPE: PRT
<213> ORGANISM: Artificial Sequence
<220> FEATURE:
<223> OTHER INFORMATION: Amino acid sequence showing the fusion of a
      chlorophyllase gene to the Cel A signal sequence

<400> SEQUENCE: 41

-continued

```
Met Gly Phe Gly Ser Ala Pro Ile Ala Leu Cys Pro Leu Arg Thr Arg
1               5               10                  15

Arg Asn Ala Leu Lys Arg Leu Leu Ala Leu Leu Ala Thr Gly Val Ser
            20              25                  30

Ile Val Gly Leu Thr Ala Leu Ala Gly Pro Pro Ala Gln Ala Met Ala
            35              40                  45

Ala Ala Ala
    50
```